US010501712B2

(12) United States Patent
Tanner et al.

(10) Patent No.: US 10,501,712 B2
(45) Date of Patent: Dec. 10, 2019

(54) BARLEY WITH LOW LEVELS OF HORDEINS

(71) Applicants: Gregory John Tanner, Elwood (AU); Crispin Alexander Howitt, Howitt (AU)

(72) Inventors: Gregory John Tanner, Elwood (AU); Crispin Alexander Howitt, Howitt (AU)

(73) Assignees: Commonwealth Scientific and Industrial Research Organisation, Acton (AU); Walter and Eliza Hall Institute of Medical Research, Parkville (AU); Grains Research and Development Corporation, Barton (AU); Melbourne Health, Parkville (AU)

(*) Notice: Subject to any disclaimer, the term of this patent is extended or adjusted under 35 U.S.C. 154(b) by 0 days.

(21) Appl. No.: 14/843,437

(22) Filed: Sep. 2, 2015

(65) Prior Publication Data
US 2016/0130539 A1 May 12, 2016

Related U.S. Application Data

(60) Division of application No. 14/166,733, filed on Jan. 28, 2014, now Pat. No. 9,133,427, which is a continuation of application No. 12/733,139, filed as application No. PCT/AU2008/001172 on Aug. 13, 2008, now Pat. No. 8,642,846.

(60) Provisional application No. 60/964,672, filed on Aug. 13, 2007.

(51) Int. Cl.
| | | |
|---|---|---|
| *C12C 1/18* | (2006.01) | |
| *C12H 6/02* | (2019.01) | |
| *A01H 5/10* | (2018.01) | |
| *C12C 12/00* | (2006.01) | |
| *C12G 3/04* | (2019.01) | |
| *C12C 1/125* | (2006.01) | |
| *A23L 5/20* | (2016.01) | |
| *A23L 7/10* | (2016.01) | |
| *A23L 7/109* | (2016.01) | |
| *A23L 7/20* | (2016.01) | |
| *A23L 7/25* | (2016.01) | |

(52) U.S. Cl.
CPC ............ *C12C 1/18* (2013.01); *A01H 5/10* (2013.01); *A23L 5/20* (2016.08); *A23L 7/10* (2016.08); *A23L 7/109* (2016.08); *A23L 7/20* (2016.08); *A23L 7/25* (2016.08); *C12C 1/125* (2013.01); *C12C 12/00* (2013.01); *C12G 3/04* (2013.01); *C12H 6/02* (2019.02); *A23V 2002/00* (2013.01); *Y02P 60/877* (2015.11)

(58) Field of Classification Search
None
See application file for complete search history.

(56) References Cited

U.S. PATENT DOCUMENTS

| | | |
|---|---|---|
| 4,945,050 A | 7/1990 | Sanford et al. |
| 5,004,863 A | 4/1991 | Umbeck et al. |
| 5,104,310 A | 4/1992 | Saltin et al. |
| 5,141,131 A | 8/1992 | Miller et al. |
| 5,159,135 A | 10/1992 | Umbeck et al. |
| 5,177,010 A | 1/1993 | Goldman et al. |
| 5,362,865 A | 11/1994 | Austin et al. |
| 5,384,253 A | 1/1995 | Krzyzek et al. |
| 5,416,011 A | 5/1995 | Hinchee et al. |
| 5,451,513 A | 9/1995 | Maliga et al. |
| 5,463,174 A | 10/1995 | Maloney et al. |
| 5,472,869 A | 12/1995 | Krzyzek et al. |
| 5,518,908 A | 5/1996 | Corbin et al. |
| 5,545,818 A | 8/1996 | McBride et al. |
| 5,569,834 A | 10/1996 | Hinchee et al. |
| 5,589,617 A | 12/1996 | Nehra et al. |
| 5,859,347 A | 1/1999 | Brown et al. |
| 5,877,402 A | 3/1999 | Maliga et al. |
| 5,932,479 A | 8/1999 | Daniell et al. |
| 6,100,447 A | 8/2000 | Wu et al. |
| 6,541,257 B2 | 4/2003 | Lemaux et al. |
| 7,074,986 B1 | 7/2006 | Hirota et al. |
| 7,652,202 B2 | 1/2010 | Clarke |
| 8,642,846 B2 | 2/2014 | Tanner et al. |
| 9,133,427 B2 | 9/2015 | Tanner et al. |
| 2011/0135784 A1 | 6/2011 | Tanner et al. |
| 2012/0034339 A1 | 2/2012 | Giuliani et al. |
| 2016/0128345 A1 | 5/2016 | Tanner et al. |
| 2016/0130539 A1 | 5/2016 | Tanner et al. |

FOREIGN PATENT DOCUMENTS

| | | |
|---|---|---|
| AU | 667939 | 4/1996 |
| CA | 2092588 | 9/1994 |
| EP | 0465572 | 6/1995 |
| EP | 1 210 869 | 6/2002 |
| WO | WO 84/02913 | 8/1984 |
| WO | WO 87/06614 | 11/1987 |
| WO | WO 92/09696 | 6/1992 |
| WO | WO 93/21335 | 10/1993 |
| WO | WO 94/019930 | 9/1994 |
| WO | WO 97/20936 | 6/1997 |

(Continued)

OTHER PUBLICATIONS

Dostalek et al. Food additives and contaminants (2006): 23(11), pp. 1074-1078.*

(Continued)

*Primary Examiner* — Medina A Ibrahim
(74) *Attorney, Agent, or Firm* — John P. White; Gary J. Gershik; Cooper & Dunham LLP

(57) ABSTRACT

The present invention relates to methods of producing a food or malt-base beverage suitable for consumption by a subject with Coeliac's disease. In particular, the present invention relates to methods of producing a food or malt-based beverage with low levels of hordeins. Also provided are barley plants which produce grain that can be used in the methods of the invention.

14 Claims, 14 Drawing Sheets

Figure 1:
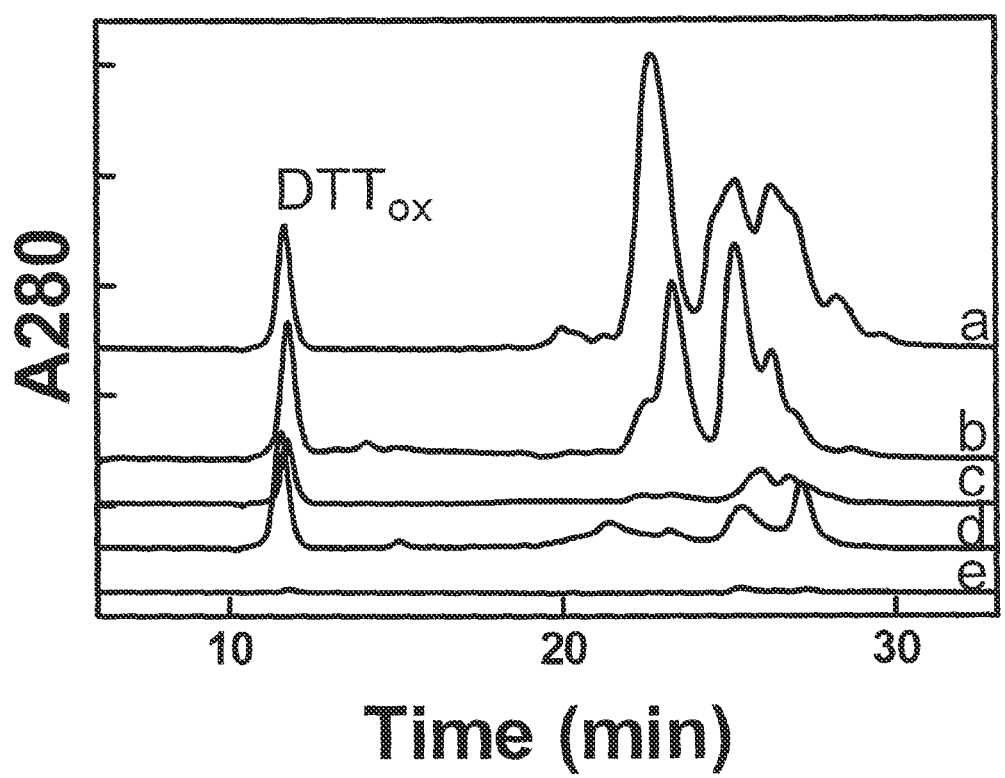

Specification includes a Sequence Listing.

(56) References Cited

FOREIGN PATENT DOCUMENTS

| WO | WO 97/048814 | 12/1997 |
|---|---|---|
| WO | WO 99/05265 | 2/1999 |
| WO | WO 99/14314 | 3/1999 |
| WO | WO 99/32619 | 6/1999 |
| WO | WO 99/49029 | 9/1999 |
| WO | WO 99/53050 | 10/1999 |
| WO | WO 2000/058453 | 10/2000 |
| WO | WO 01/34815 | 5/2001 |
| WO | WO 2005/021765 A2 | 3/2005 |
| WO | WO 2005/027953 | 3/2005 |
| WO | WO 2006/051093 | 5/2006 |
| WO | WO 2009/021285 | 2/2009 |
| WO | WO 2014/197943 | 12/2014 |

OTHER PUBLICATIONS

Apr. 1, 2016 Notification on the result of preliminary examination, issued in connection with Vietnamese Patent Application No. 1-2016-00155.

Aug. 15, 2016 First Office Action, issued in connection with Japanese Patent Application No. 2015-162679, including English language translation.

Nov. 18, 2016 First Office Action, issued in relation to Indian Patent Application No. 689/KOLNP/2010.

Jan. 17, 2017 First Examination Report, issued in connection with New Zealand Patent Application No. 631602.

Jan. 25, 2017 Annex C—Notification of Stay Proceedings, issued in connection with European Patent Application No. 08782920.6.

Aug. 8, 2016 First Office Action, issued in connection with Japanese Patent Application No. 2015-162679, including English language translation.

Howard et al. (1996) The Relationship Between D Hordein and Malting Quality in Barley. Journal of Cereal Science, 24:47-53.

Jan. 30, 2014 Response, filed in connection with Japanese Patent Application No. 2010-520-382.

Mar. 25, 2014 First Office Action, issued in connection with Mexican Patent Application No. MX/a/2010/01734.

Jun. 4, 2014 Response, filed in connection with Mexican Patent Application No. MX/a/2010/01734.

English Language Translation of Aug. 6, 2014 Office Action, issued in connection with Japanese Patent Application No. 2010-520382.

Sep. 18, 2014 Office Action, issued in connection with Canadian Patent Application No. 2,696,250.

Dec. 11, 2014 Response, filed in connection with Japanese Patent Application No. 2010-520382, including English Language amended claims.

Mar. 18, 2015 Response, filed in connection with Canadian Patent Application No. 2,696,250.

Sep. 11, 2014 Search Report, issued in connection with PCT International Patent Application No. PCT/AU2014/000619, filed Jun. 13, 2014.

Sep. 11, 2014 Written Opinion, issued in connection with PCT International Patent Application No. PCT/AU2014/000619, filed Jun. 13, 2014.

Apr. 20, 2015 Decision of Rejection, issued in connection with Japanese Patent Application No. 2010-520382.

Apr. 20, 2015 Decision to Dismiss the Amendments, issued in connection with Japanese Patent Application No. 2010-520382.

Laitilan Wirvoitusjuomatehdas: "Laitilan Kukko-Oluet Sopivat Myös Keliaakikoille" (retrieved Sep. 18, 2014) URL: deski.fi/page.php?page_id=9&tiedote_id=1017, published Jan. 22, 2012 as per Wayback Machine, including English Language Translation.

Aug. 10, 2015 First Examination Report, issued in connection with Australian Patent Application No. 2013280204.

Allred et al. (2014) "Evaluation of Qualitative and Quantitative Immunoassays to Detect Barley Contamination in Gluten-Free Beer with Confirmation Using LC/MS/MS" Journal of AOAC International 97(6): 1615.

Tanner et al. (2013) "Quantification of Hordeins by ELISA: The Correct Standard Makes a Magnitude of Difference" PLOS One 8(2): e56456 (1-14).

Lombardia et al. (2007) "A Competitive R5-ELISA for Measurements of Hydrolyzed Barley and Wheat Prolamins: Analysis of Beer" Proceedings of the EBC Congress-CD-ROM Edition; 31; 146; European Brewery Convention.

U.S. Appl. No. 60/964,672, filed Aug. 13, 2007 (Tanner et al.).

Accession No. 1103203A, Forde et al. (1985).
Accession No. 1103203B, Forde et al. (1985).
Accession No. 1103203C, Forde et al. (1985).
Accession No. 1210226A, Fabrijanski et al. (1988).
Accession No. 1307151A, Rasmussen et al. (1986).
Accession No. 1307151B, Rasmussen et al. (1986).
Accession No. 1411172A, Cameron-Mills and Brandt (1988).
Accession No. 1502200A, Fabrijanski et al. (1988).
Accession No. 1604464A, Egorov (1988).
GenBank Accession No. AAA32713, Fabrijanski et al. (1988).
GenBank Accession No. AAA32714, Chesnut et al. (1989).
GenBank Accession No. AAA32715, Chesnut et al. (1989).
GenBank Accession No. AAA32716, Chesnut et al. (1989).
GenBank Accession No. AAA32942, Forde et al. (1985).
GenBank Accession No. AAA32943, Rasmussen and Brandt (1986).
GenBank Accession No. AAA32944, Rasmussen and Brandt (1986).
GenBank Accession No. AAA32955, Cameron-Mill and Brandt (1988).
GenBank Accession No. AAA32967, Rasmussen et al. (1983).
GenBank Accession No. AAA92333, Entwistle (1988).
GenBank Accession No. AAF14232, Vrinten et al. (1999).
GenBank Accession No. AAB28161, Sainova et al. (1993).
GenBank Accession No. AAB71678, Skadsen et al. (1997).
GenBank Accession No. AAB71679, Skadsen et al. (1997).
GenBank Accession No. AAP31050, Gu et al. (2003).
GenBank Accession No. AAP31051, Gu et al. (2003).
GenBank Accession No. AAQ63842, Piston et al. (2003).
GenBank Accession No. AAQ63843, Piston et al. (2003).
GenBank Accession No. AAQ63844, Piston et al. (2003).
GenBank Accession No. AAQ63845, Piston et al. (2003).
GenBank Accession No. AAQ63846, Piston et al. (2003).
GenBank Accession No. AAQ63847, Piston et al. (2003).
GenBank Accession No. AAQ63848, Piston et al. (2003).
GenBank Accession No. AAQ63850, Piston et al. (2003).
GenBank Accession No. AAQ63851, Piston et al. (2003).
GenBank Accession No. AAQ63852, Piston et al. (2003).
GenBank Accession No. AAQ63853, Piston et al. (2003).
GenBank Accession No. AAQ63854, Piston et al. (2003).
GenBank Accession No. AAQ63855, Piston et al. (2003).
GenBank Accession No. AAQ63866, Piston et al. (2003).
GenBank Accession No. AAQ63867, Piston et al. (2003).
GenBank Accession No. AAQ63868, Piston et al. (2003).
GenBank Accession No. AAQ63869, Piston et al. (2003).
GenBank Accession No. AAQ63870, Piston et al. (2003).
GenBank Accession No. AAQ63871, Piston et al. (2003).
GenBank Accession No. AAQ63872, Piston et al. (2003).
GenBank Accession No. AAU06227, Hou et al. (2004).
GenBank Accession No. AAU06228, Hou et al. (2004).
GenBank Accession No. AAU06229, Hou et al. (2004).
GenBank Accession No. AAZ76368, Han et al. (2005).
GenBank Accession No. AAB23365, Rocher et al. (1992).
GenBank Accession No. AAB32025, Egorov et al. (1994).
GenBank Accession No. ABD14148, Potier (1993).
GenBank Accession No. ABA06537, Han et al. (2005).
GenBank Accession No. ABB82613, Han et al. (2005).
GenBank Accession No. ABB82614, Han et al. (2005).
GenBank Accession No. ABH01262, Han et al. (2006).
GenBank Accession No. AF016237, Skadsen et al. (1997).
GenBank Accession No. AF016238, Skadsen et al. (1997).
GenBank Accession No. AH005570, Skadsen et al. (1997).
GenBank Accession No. AJ580585, Snegaroff (2003).
GenBank Accession No. AY268139, Gu et al. (2003).
GenBank Accession No. AY338365, Piston et al. (2003).
GenBank Accession No. AY338366, Piston et al. (2003).
GenBank Accession No. AY338367, Piston et al. (2003).

(56) References Cited

OTHER PUBLICATIONS

GenBank Accession No. AY338368, Piston et al. (2003).
GenBank Accession No. AY338369, Piston et al. (2003).
GenBank Accession No. AY338370, Piston et al. (2003).
GenBank Accession No. AY338371, Piston et al. (2003).
GenBank Accession No. AY338372, Piston et al. (2003).
GenBank Accession No. AY338373, Piston et al. (2003).
GenBank Accession No. AY338374, Piston et al. (2003).
GenBank Accession No. AY338375, Piston et al. (2003).
GenBank Accession No. AY338376, Piston et al. (2003).
GenBank Accession No. AY338377, Piston et al. (2003).
GenBank Accession No. AY338378, Piston et al. (2003).
GenBank Accession No. AY338379, Piston et al. (2003).
GenBank Accession No. AY338380, Piston et al. (2003).
GenBank Accession No. AY338381, Piston et al. (2003).
GenBank Accession No. AY338382, Piston et al.. (2003).
GenBank Accession No. AY338383, Piston et al. (2003).
GenBank Accession No. AY338384, Piston et al. (2003).
GenBank Accession No. AY338385, Piston et al. (2003).
GenBank Accession No. AY695367, Hou et al. (2004).
GenBank Accession No. AY695368, Hou et al. (2004).
GenBank Accession No. AY695369, Hou et al. (2004).
GenBank Accession No. AY700807, Piston et al. (2004).
GenBank Accession No. AY998005, Piston et al. (2005).
GenBank Accession No. AY998008, Piston et al. (2005).
GenBank Accession No. AY998009, Piston et al. (2005).
GenBank Accession No. AY998010, Piston et al. (2005).
GenBank Accession No. BAA11642, Hirota (1996).
GenBank Accession No. CAA25509, Rasmussen et al. (1983).
GenBank Accession No. CAA25912, Forde et al. (1985).
GenBank Accession No. CAA25913, Forde et al. (1985).
GenBank Accession No. CAA25914, Forde et al. (1985).
GenBank Accession No. CAA26889, Forde et al. (1985).
GenBank Accession No. CAA31861, Cameron-Mill and Brandt.
GenBank Accession No. CAA37729, Vincente (1990).
GenBank Accession No. CAA42642, Entwistle (1991).
GenBank Accession No. CAA48209, Halford (1992).
GenBank Accession No. CAA51204, Rechinger et al. (1993).
GenBank Accession No. CAA59104, Sorensen (1995).
GenBank Accession No. CAA60681, Brandt et al. (1985).
GenBank Accession No. CAE45747, Snegaroff (2003).
GenBank Accession No. CAE85306, Kock and Bauer (2003).
GenBank Accession No. CAE85351, Bauer (2003).
GenBank Accession No. D82941, Glass et al. (2000).
GenBank Accession No. DQ148297, Han et al. (2005).
GenBank Accession No. DQ178602, Han et al. (2005).
GenBank Accession No. DQ189997, Han et al. (2005).
GenBank Accession No. DQ267476, Han et al. (2005).
GenBank Accession No. DQ267477, Han et al. (2005).
GenBank Accession No. DQ267478, Han et al. (2005).
GenBank Accession No. DQ267479, Han et al. (2005).
GenBank Accession No. DQ267480, Han et al. (2005).
GenBank Accession No. DQ267481, Han et al. (2005).
GenBank Accession No. DQ826387, Han et al. (2006).
GenBank Accession No. J01237, Forde et al. (1981).
GenBank Accession No. K03147, Forde et al. (1985).
GenBank Accession No. M23836, Rasmussen et al. (1983).
GenBank Accession No. M23869, Rasmussen et al. (1983).
GenBank Accession No. M35610, Rasmussen et al. (1986).
GenBank Accession No. M35611, Rasmussen and Brandt (1986).
GenBank Accession No. M36378, Cameron-Mill and Brandt (1988).
GenBank Accession No. M36941, Entristle (1988).
Accession No. P06470, Forde et al. (1985).
Accession No. P06471, Forde et al. (1985).
Accession No. P06472, Forde et al. (1985).
Accession No. P17990, Cameron-Mills and Brandt (1988).
Accession No. P17991, Rasmussen et al. (1986).
Accession No. P17992, Rasmussen et al. (1986).
Accession No. P29835, Shorrosh et al. (1992).
Accession No. P80198, Rechinger et al. (1993).
Accession No. P27919, Fabijanski et al. (1988).
Accession No. P80356, Chesnut et al. (1989).
Accession No. P06293, Brandt et al. (1990).
Accession No. Q09095, Pernollet et al. (1987).
Accession No. Q09097, Pernollet et al. (1987).
Accession No. Q09114, Bietz et al. (1982).
GenBank Accession No. 566938, Sainova et al. (1993).
Accession No. S06211, Pernollet et al. (1987).
Accession No. S07621, Pernollet et al. (1987).
Accession No. S07622, Pernollet et al. (1987).
GenBank Accession No. X01024, Rasmussen et al. (1983).
GenBank Accession No. X01777, Forde et al. (1985).
GenBank Accession No. X01778, Forde et al. (1985).
GenBank Accession No. X01779, Forde et al. (1985).
GenBank Accession No. X03103, Forde et al. (1985).
GenBank Accession No. X13508, Cameron-Mill and Brandt (1988).
GenBank Accession No. X53690, Vincente (1990).
GenBank Accession No. X53691, Vincente (1990).
GenBank Accession No. X60037, Entistle et al. (1991).
GenBank Accession No. X68072, Halford (1992).
GenBank Accession No. X72628, Rechinger et al. (1993).
GenBank Accession No. X84368, Sorensen (1995).
GenBank Accession No. X87232, Brandt et al. (1985).
Supplementary European Search Report and Search Opinion dated Dec. 9, 2010 in connection with European Patent Application No. 08782920.6.
Laitilan Wirvoitusjuomatehdas: "Laitilan Kukko-oluet sopivat myös keliakiaakikoille", Sep. 6, 2005, retrieved from: www.deski.fi/page.php?page_id=9&tiedote+id=1017, including English Language Translation.
Doll et al. (1980) "A nearly non.functional mutant allele of the storage protein locus Hor2 in barley" Hereditas 93: 217-222.
Shewry et al. (1979) "Effect of High-Lysine Mutations on the Protein Fractions of Barley Grain" Biochemical Genetics, vol. 18 1, No. 1-2, pp. 133-152.
Tallberg (1981) "Protein and lysine content in high-lysine double-recessives of barley. I. Combinations between mutant 1508 and a Hiproly back-cross" Hereditas 94: 253-260.
Tallberg (1982) "Characterization of high-lysine barley genotypes" Hereditas 96: 229-245.
Response to Search Opinion filed Jul. 6, 2011 in connection with European Patent Application No. 08782920.6.
European Examination Report dated Dec. 15, 2011 in connection with European Patent Application No. 08782920.6.
Response filed to the Examination Report filed on Jun. 25, 2012 in connection with European Patent Application No. 08782920.6.
New Zealand Examination Report dated Nov. 24, 2010 in connection with New Zealand Patent Application No. 583466.
Response filed to New Zealand Examination Report filed on May 16, 2012 in connection with New Zealand Patent Application No. 583466.
Second New Zealand Examination Report dated Jun. 1, 2012 in connection with New Zealand Patent Application No. 583466.
Response filed to New Zealand Examination Report filed on Aug. 13, 2012 in connection with New Zealand Patent Application No. 583466.
Australian Examination Report dated Jun. 7, 2010 in connection with Australian Patent Application No. 2008286698.
English Language Translation of Chinese Office Action dated Jan. 30, 2012 in connection with Chinese Patent Application No. 200880111180.3.
Response filed to Chinese Office Action filed on Jun. 14, 2012 in connection with Chinese Patent Application No. 200880111180.3, with English Language Filed Claims.
Second Chinese Office Action dated Dec. 11, 2012 in connection with Chinese Patent Application No. 200880111180.3, including English Language Translation.
Russian Office Action dated Jun. 6, 2011 in connection with Russian Patent Application No. 2010109421, including English Language Translation.
Response filed to Russian Office Action filed in connection with Russian Patent Application No. 2010109421, with English Language Claims.

(56) References Cited

OTHER PUBLICATIONS

Second Russian Office Action dated May 21, 2012 in connection with Russian Patent Application No. 2010109421, including English Language Translation.
Response filed to Second Russian Office Action filed in connection with Russian Patent Application No. 2010109421, with English Language Claims.
Third Russian Office Action dated Aug. 22, 2012 in connection with Russian Patent Application No. 2010109421.
Ukrainian Office Action dated Jun. 13, 2012 in connection with Ukrainian Patent Application No. 2010 02764.
Response filed to Ukrainian Office Action filed on Aug. 30, 2012 in connection with Ukrainian Patent Application No. 2010 02764.
Abdullah et al. (1986) "Efficient Plant Regeneration from Fice Protoplasts Through Somatic Embryogenesis" Biotechnology 4:1087.
Almeida and Allshire (2005) "RNA silencing and genome regulation" TRENDS Cell Biol 15: 251-258.
Anderson et al. (2000) "In vivo antigen challenge in coeliac disease identifies a single transglutaminase-modified peptide as the dominant A-gliadin T-cell epitope" Nature Medicine 6: 337-342.
Anderson et al. (2005) "T cells in peripheral blood after gluten challenge in coeliac disease" Gut 54:1217-1223.
Aventz-Hansen (2000) "The Intestinal T Cell Response to a-Gliadin in Adult Coeliac Disease Is Focused on a Single Deamidated Glutamine Targeted by Tissue Transglutaminase" Journal of Experimental Medicine 191: 603-612.
Biagi et al. (2004) "A Milligram of Gluten a Day Keeps the Mucosal Recovery Away: A Case Report" Nutrition Reviews 62:360-363.
Bourque (1995) "Antisense strategies for genetic manipulations in plants" Plant Sci. 105: 125-149.
Bradford (1976) "A Rapid and Sensitive Method for the Quantitation of Microgram Quantities of Protein Utilizing the Principle of Protein-Dye Binding" Analytical Chemistry 72: 248-254.
Brandt et al. (1990) "A plant serpin gene Structure, organization and expression of the gene encoding barley protein $Z_4$" Eur J Biochem 194:499-505.
Campbell et al. (2001) "Identification of a juvenile hormone esterase gene by matching its peptide mass fingerprint with a sequence from the *Drosophila* genome project" Insect Biochemistry and Molecular Biology 31: 513-520.
Capecchi (1980) "High Efficiency Transformation by Direct Microinjection of DNA into Cultured Mammalian Cells" Cell 22:479-488.
Catassi et al. (2007) "A prospective, double-blind, placebo-controlled trial to establish a safe gluten threshold for patients with coeliac disease" Am. J. Clin. Nutr. 85:160-166.
Cheng et al. (1996) "Production of fertile transgenic peanut (*Arachis hypogaea* L.) plants using Agrobacterium tumefaciens" Plant Cell Rep. 15:653-657.
Clapp (1993) "The 16-Kilodalton N-Terminal Fragment of Human Prolactin Is a Potent Inhibitor of Angiogenesis" Clin. Perinatol. 20:155-168.
Collin et al. (2004) "The safe threshold for gluten contamination in gluten-free products. Can trace amounts be accepted in the treatment of coeliac disease?" Aliment Pharmacol Ther 19:1277-1283.
Comai et al. (2004) "Efficient discovery of DNA polymorphisms in natural populations by Ecotilling" Plant J 37: 778-786.
Dailey et al (1988) "Hordein Gene Expression in a Low Protein Barley Cultivar" Plant Physiol 88:450-453.
Davies et al. (1993) "Spatial and Temporal Patterns of B Hordein Synthesis in Developing Barley (*Hordeum vulgare* L.) Caryopses" Cell Biology International Reports 17:195-202.
De Angelis et al., (2007) "Probiotic Preparation Has the Capacity to Hydrolyze Proteins Responsible for Wheat Allergy" Journal of Food Protection, vol. 70, No. 1, pp. 135-144.
Doll (1980) "A nearly non-functional mutant allele of the storage protein locus Hor2 in barley" Heriditas 93:217-222.
Doll (1983) Barley seed proteins and possibilities for their improvement. In "Seed Proteins: Biochemistry, Genetics, Nutritional Value", Gottschalk W, Muller HP (eds). Martinus Nijhoff, The Hague:207-223.

Doll and Oram (1989) "Deviating Mendelian segregation of barley gene lys 3a" Hereditas 110:97-99.
Doll et al (1973) "Hans Doll: Inheritance of the high-lysine character of a barley mutant" Barley Genetics Newsletter 3:12-13.
Dostalek et al. (2006) "Immunochemical determination of gluten in malts and beers" Food Additives and Contaminants 23:1074-1078.
Douliez et al. (2000) "Structure, Biological and Technological Functions of Lipid Transfer Proteins and Indolines, the Major Lipid Binding Proteins from Cereal Kernels" J Cereal Sci 32:1-20.
Ellis et al. (1990) "Detection and estimation of the barley prolamin content of beer and malt to assess their suitability for patients with coeliac disease" Clin Chim Acta 189: 123-130.
Evans et al (2002) "Don't Be Fobbed Off: The Substance of Beer Foam—A Review" J. Am. Soc. Brew. Chem. 61:55-62.
Fasano et al. (2003) "Prevalence of Coeliac Disease in At-Risk and Not-At-Risk Groups in the United States" Archives of Internal Medicine 163: 286-292.
Field et al. (1982) "The Purification and Characterization of Homologous High Molecular Weight Storage Proteins from Grain of Wheat, Rye and Barley" Theoretical and Applied Genetics 62:329-336.
Folich et al. (1957) "A Simple Method for the Isolation and Purification of Total Lipides from Animal Tissues" J Biol Chem. 226:497-509.
Garcia-Casado et al. (2001) "Isolation and characterization of barley lipid transfer protein and protein Z as beer allergens" J. Allergy Clin. Immunol. 108:647-9.
Gellrich et al. (2003) "Biochemical Characterization and Quantification of the Storage Protein (Secalin) Types in Rye Flour" Cereal Chem. 80(1):102-109.
Graham et al. (1973) "Transformation of Rat Cells by DNA of Human Adenovirus" Virology 54:536-539.
Grant et al. (1995) "Transformation of peas (*Pisum sativum* L.) using immature cotyledons" Plant Cell Rep. 15:254-258.
Hadjivassiliou et al. (2004) "The immunology of gluten sensitivity: beyond the gut" Trends Immunol 25:578-82.
Haseloff and Gerlach (1988) "Simple RNA enzymes with new and highly specific endoribonuclease activities" Nature 334:585-591.
Hejgaard et al. (1985) "Sequence homology between barley endosperm protein Z and protease inhibitors of the $a_1$-antitrypsin family" FEBS 180:89-94.
Hejaard and Boisen (1980) "High-lysine proteins in Hiproly barley breeding: Identification, nutritional significance and new screening methods" Hereditas 93: 311-320.
Henikoff et al. (2004) "Tilling. Traditional Mutagenesis Meets Functional Genomics" Plant Physiol 135: 630-636.
Hogberg et al. (2004) "Oats to children withi newly diagnosed coeliac disease: a randomized double blind study" Gut 53: 649-654.
Ingerversen et al. (1973) "Induced Seed Protein Mutant of Barley" Experientia 29:1151-1152.
Jaradat (1991) "Grain protein variability among populations of wild barley (*Hordeum spontaneum* C. Koch.) from Jordan" Theor Appl Genet 83:164-168.
Kanerva et al. (2005) "Determination of Prolamins in Beers by ELISA and SDS-PAGE" J Instit Brewing 111: 61-64.
Kapp and Bamforth (2002) "The foaming properties of proteins isolated from barley" J. Sic. Food Agric. 82:1276-1281.
Karlsson (1977) "Linkage studies in a gene for high lysine content in Riso barley mutant 1508." Barley Genetics Newsletter, vol. 7, II. Research Notes.
Kasarda et al. (1984) "Nucleic acid (cDNA) and amino acid sequences of a-type gliadins from wheat (*Triticum aestivum*)" PNAS 81:4712-4716.
Kim et al. (2004) "Structural basis for HLA-DQ2-mediated presentation of gluten epitopes in celiac disease" Proc Natl Acad Sci USA 101:4175-9.
Klemsdal (1987) "The barley high lysine genes of mutants 1508 and 527 alter hordein polypeptide composition quantitatively, but not qualitatively" Hereditas 107: 107-114.
Koziel et al. (1996) "Optimizing expression of transgenes with an emphasis on post-transcriptional events" Plant Mol. Biol. 32:393-405.
Kreis and Doll (1980) "Starch and prolamin level in single and double high-lysine barley mutants" Physiol. Plant 48:139-143.

(56) References Cited

OTHER PUBLICATIONS

Kreis and Shewry (1989) "Unusual Features of Cereal Seed Protein Structure and Evolution" BioEssays 10:201-207.
Kreis et al. (1983) "Molecular Analysis of a Mutation conferring the High-Lysine Phenotype on the Grain of Barley (*Hordeum vulgare*)" Cell 34:161-177.
Kreis et al. (1984) "Molecular Analysis of the Effects of the lys 3a Gene on the Expression of Hor Loci in Developing Endosperms of Barley (*Hordeum vulgare* L.)" Biochem. Genetics 22: 231-255.
Lewis (2005) "Celiac Disease, Beer, and Brewing" TIBBA TQ 42:45-48.
Lu et al. (1993) "High Efficiency Retroviral Mediated Gene Transduction into Single Isolated Immature and Replatable $CD34^{3+}$ Hematopoietic Stem/Progenitor Cells from Human Umbilical Cord Blood" J. Exp. Med. 178:2089-2096.
Lundin et al. (2003) "Oats induced villous atrophy in coeliac disease" Gut 52: 1649-1652.
Marti et al. (2005) "Prolyl Endopeptidase-Mediated Destruction of T Cell Epitopes in Whole Gluten: Chemical and Immunological Characterization" J Pharmacol Exp Therapeut 312:19-26.
Mena et al. (1998) "An endosperm-specific DOF protein from barley, highly conserved in wheat, binds to and activates transcription from the prolamin-box of native B-hordien promoter in barley endosperm" Plant J. 16:53-62.
Millar and Waterhouse (2005) "Plant and animal microRNAs: similarities and differences" Funct Integr Genomics 5:129-135.
Mullins et al. (1999) "Isolation of mutants exhibiting altered resistance to Sclerotinia sclerotiorum from small M2 populations of an oilseed rape (*Brassica napus*) variety" Eur J Plant Pathol 105:465-475.
Munck et al. (1970) "Gene for Improved Nutritional Value in Barley Seed Protein" Science 168:985-987.
Olsen (1977) "Diallel analysis of high lysine barley, *Hordeurn vulgare* L." Hereditas 87: 11-20.
Onishi et al. (1999) "Monoclonal Antibody Probe for Assessing Beer Foam Stabilizing Proteins" J. Agric. Food Chem. 47:3044-3049.
Pasquinelli et al. (2005) "MicroRNAs: a developing story" Curr Opin Genet Develop 15: 200-205.
Peraaho et al. (2004a) "Oats Can Diversify a Gluten-Free Diet in Celiac Disease and Dermatitis Herpetiformis" Journal of the American Dietetic Association 104: 1148-1150.
Peraaho et al. (2004b) "Effect of an Oats-Containing Gluten-free Diet on Symptoms and Quality of Life in Coeliac Disease. A Randomized Study" Scandinavian Journal of Gastroenterology 39: 27-31.
Perriman et al. (1992) "Extended target-site specificity for a hammerhead ribozyme" Gene 113: 157-163.
Perrocheau et al (2005) "Probing heat-stable water-soluble proteins from barley to malt and beer" Proteomics 5:2849-2858.
Peters et al. (2003) "Causes of Death in Patients With Celiac Disease in a Population-Based Swedish Cohort" Arch Intern Med 163:1566-1572.
Pynnonen et al. (2004) "Mental Disorders in Adolescents With Celiac Disease" Psychosomatics 45: 325-335.
Senior (1998) "Uses of Plant Gene Silencing" Biotech. Genet. Engin. Revs. 15: 79-119.
Shan et al. (2002) "Structural Basis for Gluten Intolerance in Celiac Sprue" Science 297: 2275-2279.
Shewry and Halford (2002) "Cereal seed storage proteins: structures, properties and role in grain utilization" Journal of Experimental Botany 53:947-958.
Shewry et al (1979) "Protein Metabolism in Developing Endosperms of High-Lysine and Normal Barley" Cereal Chem. 56:110-117.
Shewry et al (1987) "Characterization and Genetic Control of the Prolamins of Haynaldia villosa: Relationship to Cultivated Species of the *Triticeae* (Rye, Wheat, and Barley)" Biochem. Genetics 25:309-325.

Shewry et al. (1978) "An Evaluation of Techniques for the Extraction of Hordein and Glutelin from Barley Seed and a Comparison of the Protein Composition of Bomi and Riso 1508" Journal of Experimental Botany 29:677-692.
Shewry et al. (1980) "Effect of High-Lysine Mutations on the Protein Fractions of Barley Grain" Biochemical Genetics 18:33-151.
Shippy et al. (1999) "The Hairpin Ribozyme" Mol. Biotech. 12:117-129.
Skerritt (1988) "Hydrolysis of Barley Endosperm Storage Proteisn During Malting. I. Analysis Using Monoclonal Antibodies" J. Cereal Science 7:251-263.
Slade and Knauf (2005) "TILLING moves beyond functional genomics into crop improvement" Transgenic Res 14: 109-115.
Smith et al. (2000) "Total silencing by intronspliced hairpin RNAs" Nature 407: 319-320.
Sollid (2002) "Coeliac Disease: Dissecting a Complex Inflammotry Disorder" Nature Reviews Immunology 2: 647-655.
Sorell et al. (1998) "An innovative sandwich ELISA system based on an antibody cocktail for gluten analysis" FEBS Letts 439:46-50.
Sorensen (1992) "Methylation of B-hordein genes in barley endosperm is inversely correalted with gene activity and affected by the regulatory gene Lys3" PNAS 89:4119-4123.
Sorensen et al. (1996) "Hordein promoter methylation and transcriptional activity in wild-type and mutant barley endosperm" Mol Gen Genet 250:750-760.
Stepniak et al. (2006) "Highly efficient gluten degradation with a newly identified prolyl endoprotease: implications for celiac disease" Am J Physiol-Gastrointest Liver Physiol 291:621-629.
Tallberg (1977) "The amino-acid composition in endosperm and embryo of a barley variety and its high lysine mutant" Hereditas 87: 43-46.
Thompson (2001) "Wheat starch, gliadin, and the gluten-free diet" J. Amer Diet Assoc 101: 1456-1459.
Tingay et al. (1997) "Agrobacterium tumefaciens-mediated barley transformation" Plant J 11:1369-1376.
Toriyama et al. (1986) "Haploid and diploid plant regeneration from protoplasts of anther callus in rice" Theor. Appl. Genet. 205:34.
Treem (2004) "Emerging concepts in celiac disease" Current Opinion in Pediatrics 16: 552-559.
Ullrich and Eslick (1977) "Inheritance of the shrunken endosperm character, sex3c, of Bomi Riso mutant 1508 and its association with lysine content." Barley Genetics Newsletter 7:66-73.
Ullrich and Eslick (1978) "Inheritance of the Associated Kernel Characters, High Lysine and Shrunken Endosperm, of the Barley Mutant Bomi, Riso 1508" Barley Genetics Newsletter 8:114-125.
Vader et al. (2003) "Characterization of Cereal Toxicity for Celiac Disease Patients Based on Protein Homology in Grains" Gastroenterology 125: 1105-1113.
Verkarre et al. (2004) "Gluten-Free Diet, Chromosomal Abnormalities, and Cancer Risk in Coeliac Disease" J Pediatric Gastroenterology and Nutrition 38: 140-142.
Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.
Waterhouse et al. (1998) "Virus resistance and gene silencing in plants can be induced by simultaneous expression of sense and antisense RNA" Proc. Natl. Acad. Sci. USA 95: 13959-13964.
Wieser et al. (1994) Quantitative Determination of Gliadin Subgroups from Different Wheat Cultivars"" Journal of Cereal Science 19, 149-155.
USDA Deposit information for RISO Mutant 56, accession No. PI384986.
USDA Deposit information for RISO Mutant 1508, accession No. PI384988.
Green et al., (1997) "Grain Development Mutants of Barley" Plant Physiol. 114:203-212.
Kucharska et al., (1998) "Estimation of induced mutation rates for four esterase genes in barley (*Hordeum vulgare* L.)" J. Appl. Genet. 39(2):141-145.

(56) References Cited

OTHER PUBLICATIONS

Rasmussen et al., (1998) "Identification of two low-phytate barley (*Hordeum vulgare* L.) grain mutants by TLC and genetic analysis" Hereditas 129:107-112.
International Search Report issued by the International Searching Authority (ISA/AU) on May 8, 2009 in connection with International Application No. PCT/AU2008/001172.
European Patent Application No. EP 1,210,869 A1, published Jun. 5, 2002 (Sapporo Breweries Ltd.).
Jun. 6, 2013 Summons to Attend Oral Proceedings, issued in connection with European Patent Application No. 08782920.6.
Apr. 30, 2013, Examination Report, issued in connection with Australian Patent Application No. 2008286698.
Aastrup S. (1983) "Selection and Characterization of Low Beta Glucan Mutants from Barley" Carlsberg Research Communications, vol. 48, No. 4, pp. 307-316.
Mar. 13, 2013 Response filed in connection with Chinese Patent Application No. 20080111180.3.
Feb. 25, 2013 Response filed in connection with Australian Patent Application No. 2008286698.
Third Russian Office Action dated Aug. 22, 2012 in connection with Russian Patent Application No. 2010109421, including English Language Translation.
Ukrainian Office Action dated Jun. 13, 2012 in connection with Ukrainian Patent Application No. 2010 02764, including English Language Translation.
Jul. 5, 2013 Response, filed in connection with Australian Patent Application No. 2008286698.
Apr. 22, 2013 Office Action, issued in connection with Russian Patent Application No. 2010109421, including English Language translation.
Oct. 24, 2013 Result of Consultation in connection with European Patent Application No. EP 08 782 920.6.
Jul. 30, 2012 Office Action, issued in connection with U.S. Appl. No. 12/733,139.
Aug. 30, 2013 Response, filed in connection with U.S. Appl. No. 12/733,139.
Sep. 4, 2012 Office Communication, issued in connection with U.S. Appl. No. 12/733,139.
Sep. 5, 2012 Response, filed in connection with U.S. Appl. No. 12/733,139.
Nov. 5, 2012 Office Action, issued in connection with U.S. Appl. No. 12/733,139.
Feb. 5, 2013 Response, filed in connection with U.S. Appl. No. 12/733,139.
Apr. 9, 2013 Final Office Action, issued in connection with U.S. Appl. No. 12/733,139.
Jul. 5, 2013 Response, filed in connection with U.S. Appl. No. 12/733,139.
Sep. 20, 2013 Notice of Allowance and Summary of Examiner Interview, issued in connection with U.S. Appl. No. 12/733,139.
Feb. 16, 2010 International Preliminary Report on Patentability, issued in connection with PCT International Patent Application No. PCT/AU2008/001172.
Jan. 5, 2016 Response, filed in connection with European Patent Application No. 08782920.6.
Feb. 5, 2016 Reponse, filed in connection with Canadian Patent Application No. 2,696,250.
Sep. 11, 2014 PCT International Search Report and Written Opinion issued in connection with PCT/AU2014/000619.
May 8, 2015 International Preliminary Report on Patentability issued in connection with PCT/AU2014/000619.
Jan. 23, 2017 Extended European Search Report, issued in connection with corresponding European Patent Application No. 14810699.0.
Mar. 1, 2017 First Office Action, issued in connection with Chinese Patent Application No. 201480041134.6, including English language translation.
Mar. 29, 2017 First Examination Report issued in connection with Australian Patent Application No. 201480852.
Apr. 10, 2017 Office Action, issued in connection with Eurasian Patent Application No. 201690013, including English language translation.
English Language Translation of Jun. 6, 2017 Office Action, issued in connection with Brazilian Patent Application No. PI0815474-0.
Response filed Aug. 17, 2017 to Nov. 18, 2016 First Examination Report issued in connection with Indian Patent Application No. 689/KOLNP/2010.
Anderson O. D. (2013) "The B-hordein prolamin family of barley" NRC Research Press Genome 56: 179-185.
Arendt et al. (2008) "Gluten-free breads" Gluten-Free Cereal Products and Beverages Ed. Arendt and Bello, Elsevier Inc. Chapter 8: pp. 289-321.
Brennan et al. (1998) "The production and characterization of Hor 3 null lines of barley provides new information on the relationship of D hordein to malting performance" Journal of Cereal Science 28(3): 291-299.
Cameron-Mills V and Brandt A (1988) "A γ-hordein gene" Plant Molecular Biology 11:449-461.
Colgrave et al., (2012) "What is in a Beer? Proteomic Characterization and Relative Quantification of Hordein (Gluten) in Beer" J. Proteome Res. 11: 386-396.
Fasoli et al. (2010) "Les Maitres de l'Orge: The Proteome Content of Your Beer Mug" Journal of Proteome Research 9: 5262-5269.
Fowell et al. (2006) "The epidemiology of coeliac disease in East Dorset 1993-2002: An assessment of the 'coeliac iceberg'. And preliminary evidence of case clustering" QJMed—an International Journal of Medicine 99:453-460.
Green and Jabri (2006) "Celiac Disease" Annual Review of Medicine 57:207-221.
Gu et al. (2003) "Structural organization of the barley D-hordein locus in comparison with its orthologous regions of wheat genomes" Genome 46:1084-1097.
Hausch et al. (2002) "Intestinal digestive resistance of immunodominant gliadin peptides" Gastroenterology 122:A180.
Kahlenberg et al. (2006) "Monoclonal antibody R5 for detection of putatively coeliac-toxic gliadin peptides" European Food Research Technology. 222:78-82.
Kristoffersen HE and Flengsrud R (2000) "Separation and characterization of basic barley seed proteins" Electrophoresis 21: 3693-3700.
Lanzini et al. (2009) "Complete recovery of intestinal mucosa occurs very rarely in adult coeliac patient despite adherence to gluten-free diet" Alimentary Pharmacology & Therapeutics 29:1299-1308.
Ohlund et al. (2010). "Dietary shortcoming in children on a gluten-free diet" Journal of Human Nutrition and Dietetics 23:294-300.
Picarello et al. (2011) "Proteomic and peptidomic characterization of beer: Immunological and technological implications" Food Chemistry 124: 1718-1726.
Skovbjerg et al., (2004). "Deamidation and cross-linking of gliadin peptides by transglutaminases and the relation to celiac disease" Biochim. et Biophys. Acta—Mol. Bas.of Dis. 1690:220-230.
Tanner et al. (2010) "Dissecting the T-cell response to hordeins in coeliac disease can develop barley with reduced immunotoxicity" Alimentary Pharmacology & Therapeutics 32(9): 1184-1191.
Tye-Din et al. (2010) "Comprehensive, Quantitative Mapping of T Cell Epitopes in Gluten in Celiac Disease" Science Translational Medicine 2:41-51.
Wieser H (2008) "Detection of gluten" Gluten-Free Cereal Products and Beverages Ed. Arendt and Bello, Elsevier Inc. Chapter 3: pp. 47-80.
Jan. 22, 2018 Decision of Rejection and Decision to Reject the Amendments issued in connection with Japanese Patent Application 2015-162679 including English language translation.
Communication pursuant to Article 94(3) EPC dated Feb. 12, 2018 by the European Patent Office in connection with related European Patent Application No. EP 08 782 920.6.
Response to Communication under Article 94(3) filed Nov. 23, 2018 in connection with European Patent Application No. 08782920.6.

(56) References Cited

OTHER PUBLICATIONS

Intention to stay proceedings due to a referral to the Enlarged Board of Appeal issued Jun. 27, 2019 by the European Patent Office in connection with related European Patent Application No. EP 08 782 920.6.

Mar. 19, 2019 Written Opinion, issued in connection with Brazilian Patent Application No. BR 122018009860-0, including English language translation.

* cited by examiner

SEQUENCE LISTING

```
<160> NUMBER OF SEQ ID NOS: 5

<210> SEQ ID NO 1
<211> LENGTH: 17
<212> TYPE: PRT
<213> ORGANISM: Artificial
<220> FEATURE:
<223> OTHER INFORMATION: Antigenic peptide

<400> SEQUENCE: 1

Gln Pro Glu Gln Pro Phe Pro Gln Pro Glu Gln Pro Phe Pro Trp Gln
1               5                   10                  15

Pro

<210> SEQ ID NO 2
<211> LENGTH: 20
<212> TYPE: DNA
<213> ORGANISM: Artificial
<220> FEATURE:
<223> OTHER INFORMATION: Oligonucleotide primer

<400> SEQUENCE: 2
caacaatgaa gaccttcctc                                              20

<210> SEQ ID NO 3
<211> LENGTH: 20
<212> TYPE: DNA
<213> ORGANISM: Artificial
<220> FEATURE:
<223> OTHER INFORMATION: Oligonucleotide primer

<400> SEQUENCE: 3
tcgcaggatc ctgtacaacg                                              20

<210> SEQ ID NO 4
<211> LENGTH: 22
<212> TYPE: DNA
<213> ORGANISM: Artificial
<220> FEATURE:
<223> OTHER INFORMATION: Oligonucleotide primer

<400> SEQUENCE: 4
cgagaaggta ccattactcc ag                                           22

<210> SEQ ID NO 5
<211> LENGTH: 21
<212> TYPE: DNA
<213> ORGANISM: Artificial
```

```
<220> FEATURE:
<223> OTHER INFORMATION: Oligonucleotide primer

<400> SEQUENCE: 5
agtaacaatg aaggtccatc g                                              21
```

BARLEY WITH LOW LEVELS OF HORDEINS

This application is a divisional of U.S. Ser. No. 14/166,733, filed Jan. 28, 2014, now allowed, which is a continuation of U.S. Ser. No. 12/733,139, filed May 10, 2010, now U.S. Pat. No. 8,642,846, issued Feb. 4, 2014, which is a § 371 national stage of PCT International Application No. PCT/AU2008/001172, filed Aug. 13, 2008, which claims priority of U.S. Provisional Application No. 60/964,672, filed Aug. 13, 2007, the contents of each of which are hereby incorporated by reference into this application.

FIELD OF THE INVENTION

The present invention relates to methods of producing a food or malt-based beverage suitable for consumption by a subject with Coeliac's disease. In particular, the present invention relates to methods of producing a food or malt-based beverage with low levels of hordeins. Also provided are barley plants which produce grain that can be used in the methods of the invention.

BACKGROUND OF THE INVENTION

Coeliac (celiac) disease (CD, also called celiac sprue) is a T-cell mediated autoimmune disease of the small intestine which is triggered in susceptible individuals by ingestion of particular storage proteins, collectively known as prolamins, from wheat (gluten consisting of glutenins and gliadins), barley (hordeins) or rye (secalins). Oat prolamins (avenins) appear to be tolerated by the majority of coeliacs (Hogberg et al., 2004; Peraaho et al., 2004a) but may induce positive reactions in a minority of coeliacs (Lundin et al. 2003; Peraaho et al. 2004b). CD occurs in approximately 0.25-1% of the population in at least Australia, North and South America, Europe, Africa and India (Hovell et al. 2001; Fasano et al. 2003; Treem 2004) but the disease is probably underdiagnosed. Increased awareness of the symptoms and consequences of untreated CD has lead to rates of diagnosis in Australia increasing at 15% per year. About 1 in 4 Caucasians and West Asians carry the HLA-DQ8 or -DQ2 alleles which are a necessary but not sufficient determinant of CD (Treem 2004). However, only about 1 in 20 people with these alleles develop CD. At present the only treatment is total avoidance of wheat, barley and rye, as recurrences may be triggered by consumption of as little as 10 milligrams of gluten per day (Biagi et al., 2004).

If undiagnosed or untreated, CD has serious health consequences that may be life threatening, particularly in infants. CD causes deformation of absorptive villae of the small intestine and may lead to destruction of the villi. As a result, nutrients are poorly absorbed and this may be associated with weight loss, fatigue, mineral deficiencies, dermatitis and loss of night vision as well as intense intestinal distress which usually includes bloating, diarrhea and cramps. Subjects with untreated CD have increased risks of cancer such as a 10-fold increased risk of carcinoma of the small intestine, a 3-6 fold increase in the risk of non-Hodgkin lymphoma and 28-fold increased risk of intestinal T-cell lymphoma. CD also presents a 3-fold increase in the risk of Type I diabetes (Peters et al. 2003; Peters et al. 2003; Verkarre et al. 2004). A five fold increase in the incidence of mental depression has been reported in coeliac patients (Pynnonen et al. 2004).

The molecular basis of coeliac disease is now reasonably well understood (Said 2002; Hadjivassiliou et al. 2004) as being a reaction to a specific sequence of amino acids in prolamins. Poorly digested prolamin peptides rich in proline and glutamine conform to the substrate motif targeted by human tissue trans-glutaminase (tTG) in the intestinal mucosa allowing key glutamine residues to be deamidated. The resultant negatively charged glutamic acid allows the deamidated prolamin to bind to a specific class of HLA molecules (DQ2 or DQ8) (Kim et al. 2004). Specific T-cell clones, so called DQ2(8)/CD4$^+$ restricted T-cells, targeted to the intestinal endothelium are stimulated to proliferate, releasing lymphokines which drive villous atrophy or antibody production (Hadjivassiliou et al. 2004). These T-cell clones reach a maximum concentration in the peripheral blood of coeliacs around six days after a dietary challenge (Anderson et al. 2000). The coeliac toxicity of purified proteins may therefore be sensitively and specifically determined by measuring their capacity to stimulate T-cells to produce IFN-γ, a cytokine fundamental to the pathogenesis of the enteropathy seen in coeliac disease. It therefore appears that the disease is caused by host's immune system reacting to prolamins as if they are an invading pathogen, mounting a vigorous immune response, rather than as an allergy.

Wheat gluten is composed of many hundreds of different but related proteins including the monomeric gliadins and the polymeric glutenins. Gliadins account for about half of the gluten fraction and α-gliadins comprise over 50% of the gliadins (Wieser et al., 1994; Gellrich et al., 2003). To date, the majority of coeliac toxicity data has focused on α-gliadin, the first prolamin to be cloned and fully sequenced (Kasarda et al. 1984). The coeliac toxicity of wheat α-gliadin is largely determined by a single glutamine residue within a key 17 amino acid epitope (Arentz-Hansen et al. 2000; Anderson et al. 2000; Shan et al. 2002). Naturally occurring and synthetic peptides carrying point mutations in this region have been identified which are not toxic (Vader et al. 2003). Therefore, it appears likely that other non-toxic but functional prolamin molecules may be identified. At present, useful prediction of coeliac toxicity is limited to the small fraction of prolamins which have been characterized in terms of amino acid sequence or the nucleotide sequence of the genes encoding them.

Barley is a diploid cereal that is widely grown in cooler climates for food and beverage production. Barley seed proteins are classified into albumin, globulin, prolamin (hordein) and glutelin according to their solubility in water, salt solution, aqueous alcohol and basic or acid solutions, respectively. Approximately half of the seed storage proteins in barley are found in the prolamin fraction. These prolamins are primarily reserve proteins that function as sources of carbon, nitrogen or sulphur for growth and development following germination. Hordein constitutes about 40% of the seed protein, although this is dependent on the nitrogen supply of the plant during growth. The loci encoding the barley prolamins have been characterized, mostly because of their contribution to barley malting quality and foam formation and haze in beer production. There are four classes of prolamins in barley, the B, C, D and γ-hordeins encoded by the Hor2, Hor1, Hor3, and Hor5 loci, respectively, on chromosome 1H (Shewry et al. 1999). These loci encode proteins which vary from a single prolamin (e.g. D hordein) to protein families containing 20-30 members (e.g. B and C hordeins). The B and C hordeins are relatively more abundant, comprising about 70% and 24% of the total hordeins, respectively. The D and γ-hordeins represent minor components at about 2-4% each. The molecular weight of hordeins varies from about 35 kDa to 100 kDa. There are no barley prolamins which have close homology to wheat α-gliadins, however it is widely accepted that hordeins are toxic to coeliacs (Williamson & Marsh 2000). The extent to which the individual hordeins of barley are CD-inducing has not been reported.

Beer is a widely consumed product made front malted barley, therefore beer is widely assumed to be not suitable for coeliacs and generally excluded from their diet. Kanerva et al. (2005) were able to identify prolamins at low levels in all but one of a number of beers. Physicians and nutritionists generally urge their CD patients to assiduously avoid any wheat, barley or rye containing products, including beer. In the US, the FDA definition of "gluten free" requires the product to be made from gluten-free raw materials only, i.e. containing no wheat, barley or rye whatsoever. The Codex Alimentarius permits the "gluten-free" label on foods containing no more than 200 ppm of gluten (0.2 g per kilogram or liter) and this is also the European standard for "gluten-free". Most coeliacs can tolerate up to about 10 mg of gluten per day without major effect (Thompson, 2001).

Prolamins toxic to coeliac patients may be specifically detected with immunoassays such as ELISA (Ellis et al., 1990; Sorell et al., 1998). These assays depend on the specific interaction between the protein and antibody. Sodium dodecyl sulfate-polyacrylamide gel electrophoresis (SDS-PAGE) and HPLC have also been used (Kanerva et al., 2005; Marchylo et al., 1986; Sheehan and Skerritt, 1997).

There is therefore a need for barley with substantially lower levels of CD-inducing hordeins which could be used in food and drink products for CD-susceptible subjects.

SUMMARY OF THE INVENTION

There are four classes of prolamins in barley, the B, C, D and γ-hordeins encoded by the Hor2, Hor1, Hor3, and Hor5 loci, respectively. The present inventors have found that at least the B, C and D classes induce undesirable inflammatory responses in subjects with coeliac's disease.

Whilst various barley mutants have previously been identified with produce certain classes of hordeins at reduced levels, it had also been observed that this was at least compensated by the increased production of other classes of hordeins. This suggests that the barley seed has compensatory mechanisms to ensure certain levels of hordeins required for the seed to be viable. Surprisingly, the present inventors have determined that most, if not all, of barley hordein production can be abolished and viable seeds obtained which are able to germinate and produce barley plants in the field, despite the loss of the major storage form of nitrogen in the seed. These seeds are particularly useful for the production of foods and drinks for consumption by subjects with coeliac's disease.

Thus, in one aspect the present invention provides a method of producing a food or malt-based beverage, the method comprising mixing barley grain, or malt, flour or wholemeal produced from said grain, with at least one other food or beverage ingredient, wherein the grain, malt, flour or wholemeal comprises about 25% or less of the level of hordeins when compared to grain from a corresponding wild-type barley plant or malt, flour or wholemeal produced in the same manner from grain from a corresponding wild-type barley plant, thereby producing the food or malt-based beverage.

Preferably, the grain, malt, flour or wholemeal comprises about 15% or less, about 10% or less, about 7.5% or less, about 5% or less or more preferably about 2.5% or less of the level of hordeins when compared to grain of the corresponding wild-type barley plant, or wild-type malt, flour or wholemeal produced in the same manner.

Examples of a wild-type barley plant include, but are not limited to, Bomi, Sloop, Carlsberg II, K8 or L1.

In another embodiment, the grain comprises about 25% or less, about 20% or less, about 15% or less, about 10% or less, about 7.5% or less, about 5% or less or more preferably about 2.5% or less of the level of B, C and/or D hordeins or any combinations thereof when compared to grain of the corresponding wild-type barley plant. The malt, flour or wholemeal may comprise the same extent of reduction in the level of B, C and/or D hordeins or any combinations thereof.

In another embodiment, the flour which comprises less than about 0.4%, less than about 0.3%, less than about 0.2% and more preferably less than about 0.1% hordeins. Hordein levels in flour produced from said grain can be determined by any technique known in the art such as alcohol fractionation.

In an embodiment, the grain has an average weight (100 grain weight) of at least about 2.4 g. Preferably, the grain has an average weight of about 2.4 g to about 6 g, more preferably an average weight of about 3.5 g to about 6 g.

In another embodiment, the starch content of the grain is at least about 50% (w/w). More preferably, the starch content of the grain is about 50% to about 70% (w/w). The starch content can be determined using any technique known in the art. For example, a method as provided in Example 4 can be used.

In a further embodiment, the coeliac toxicity of flour produced from the grain is less than about 50%, less than about 25%, more preferably about 10% or less, of flour produced from grain of a corresponding wild-type barley plant. The coeliac toxicity may be determined using any technique known in the art. For example, a method as provided in Example 1 can be used.

In yet another embodiment, malt produced from the grain comprises less than about 200 ppm hordeins, less than about 125 ppm hordeins, more preferably less than about 75 ppm hordeins. The hordein content can be also determined using any technique known in the art. For example, a method as provided in Example 7 can be used.

In another embodiment, at least about 50% of the genome of the barley grain is identical to the genome of a barley cultivar Sloop.

Preferably, the grain is from a plant which is homozygous for at least one, at least two, at least three or more loci for a genetic variation(s) which results in reduced levels of at least one, at least two or all three hordein classes of the B, C and D classes when compared to a corresponding wild-type barley plant. More preferably, these genetic variations are alleles which delete most or all of the B-hordein encoding genes at the Hor2 locus and/or a mutant allele at the Lys3 locus of barley.

In one embodiment, the grain is from a non-transgenic plant. For example, the grain can be from a cross between Riso 56 and Riso 1508 or progeny thereof comprising the hor2 and lys3 mutations, respectively, present in these parental lines. Preferably, such progeny plants comprise a substantially different genetic background to either Riso 56 or Riso 1508, for example comprising less than about 25% of the genetic background of these parental lines.

In another embodiment, the grain is from a transgenic plant.

One embodiment of a transgenic plant is a plant that comprises a transgene which encodes a polynucleotide which down-regulates the production of at least one hordein in the grain. Preferably, the polynucleotide of this embodiment is an antisense polynucleotide, a sense polynucleotide, a catalytic polynucleotide, an artificial microRNA or a duplex RNA molecule which down-regulates expression of one or preferably more genes encoding hordeins.

Another embodiment of a transgenic plant is a plant that comprises a transgene encoding a prolamin which is less toxic, or preferably non-toxic, to a subject with coeliac's disease. An example of a prolamin which is non-toxic to a subject with coeliac's disease includes, but is not limited to, oat avenins and maize zeins.

In an embodiment, the method comprises producing flour or wholemeal from the grain.

In a particularly preferred embodiment, the method further comprises producing malt from the grain. In an embodiment, the method further comprises fractionating dried germinated grain into two or more of an endosperm fraction, an endothelial layer fraction, a husk fraction, an acrospire fraction, and a malt rootlets fraction; and combining and blending predetermined amounts of two or more of the fractions.

With regard to the production of malt and beer, an important component of the barley seed is starch. However, starch levels in barley mutants with decreased levels of hordeins has previously been shown to have reduced levels of starch which would be expected to make the seed unsuitable for producing malt and beer. The inventors were particularly surprised to find that barley seeds where most, if not all, of barley hordein production had been abolished could be used to produce malt and beer with suitable characteristics for commercial production. Thus, in a particularly preferred embodiment, the malt-based beverage is beer or whiskey, and the method comprises germinating the grain.

In an embodiment, the malt-based beverage is beer which comprises at least about 2%, more preferably at least about 4%, alcohol. Preferably, the alcohol is ethanol.

In yet a further embodiment, the malt-based beverage is beer which comprises less than about 1 ppm hordeins.

In a further embodiment, at least about 50% of the grain germinates within 3 days following imbibition under typical conditions as used in malting.

Examples of food products which can be produced using the methods of the invention include, but are not limited to, flour, starch, leavened or unleavened breads, pasta, noodles, animal fodder, breakfast cereals, snack foods, cakes, malt, pastries or foods containing flour-based sauces.

Preferably, the food or malt-based beverage is for human consumption. In a further preferred embodiment, following consumption of the food or drink at least one symptom of coeliac's disease is not developed by a subject with said disease.

In another aspect, the present invention provides a method of producing a food or malt-based beverage, the method comprising mixing malt comprising one or more barley grain proteins and less than about 200 ppm hordeins and/or flour comprising one or more barley grain proteins and less than about 0.4% hordeins, at least one other food or beverage ingredient thereby producing the food or malt-based beverage.

In an embodiment, the method comprises obtaining the malt and/or flour.

In yet another aspect, the present invention provides a method of producing a food or malt-based beverage, the method comprising mixing barley grain, or malt, flour or wholemeal produced from said grain, with at least one other food or beverage ingredient, thereby producing the food or malt-based beverage, wherein flour produced from the grain comprises less than about 0.4% hordeins, and/or malt produced from the grain comprises less than about 200 ppm hordeins.

In an embodiment, the method comprises obtaining the malt and/or flour.

In another aspect, the present invention provides a barley plant which produces grain comprising about 25% or less of the level of hordeins when compared to grain from a corresponding wild-type barley plant.

Preferably, the grain comprises about 15% or less, about 10% or less, about 7.5% or less, about 5% or less or more preferably about 2.5% or less of the level of hordeins when compared to grain of the corresponding wild-type barley plant.

Examples of a wild-type barley plant include, but are not limited to, Bomi, Sloop, Carlsberg II, K8 or L1.

In another embodiment, the grain comprises about 25% or less, about 20% or less, about 15% or less, about 10% or less, about 7.5% or less, about 5% or less or more preferably about 2.5% or less of the level of B, C and/or D hordeins or any combinations thereof when compared to grain of the corresponding wild-type barley plant.

In another embodiment, flour produced from the grain comprises less than about 0.4%, less than about 0.3%, less than about 0.2% and more preferably less than about 0.1% hordeins.

In an embodiment, the grain has an average weight (100 grain weight) of at least about 2.4 g. Preferably, the grain has an average weight of about 2.4 g to about 6 g, more preferably an average weight of about 3.5 g to about 6 g.

In another embodiment, the starch content of the grain is at least about 50% (w/w). More preferably, the starch content of the grain is about 50% to about 70% (w/w).

In a further embodiment, the coeliac toxicity of flour produced from the grain is less than about 50%, less than about 25%, more preferably about 10% or less, of flour produced from grain of a corresponding wild-type barley plant.

In yet another embodiment, malt produced from the grain comprises less than about 200 ppm hordeins, less than about 125 ppm hordeins, more preferably less than about 75 ppm hordeins.

In another embodiment, at least about 50% of the genome of the barley grain is identical to the genome of a barley cultivar Sloop.

Preferably, the grain is from a plant which is homozygous for at least one, at least two, at least three or more loci for a genetic variation(s) which results in reduced levels of at least one, at least two or all three hordein classes of the B, C and D classes when compared to a corresponding wild-type barley plant.

In one embodiment, the grain is from a non-transgenic plant. For example, the grain can be from a cross between Riso 56 and Riso 1508 or progeny thereof comprising the hor2 and lys3 mutations, respectively, present in these parental lines. Preferably, such grain comprises a substantially different genetic background to either Riso 56 and Riso 1508, for example comprising less than 25% of the genetic background of these parental lines.

In another embodiment, the grain is from a transgenic plant.

One embodiment of a transgenic plant is a plant that comprises a transgene which encodes a polynucleotide which down-regulates the production of at least one hordein in the grain. Preferably, the polynucleotide of this embodiment is an antisense polynucleotide, a sense polynucleotide, a catalytic polynucleotide, an artificial microRNA or a duplex RNA molecule which down-regulates expression of one or preferably more genes encoding hordeins.

Another embodiment of a transgenic plant is a plant that comprises a transgene encoding a prolamin which is less toxic, preferably non-toxic to a subject with coeliac's disease. An example of a prolamin which is non-toxic to a subject with coeliac's disease includes, but is not limited to, oat avenin.

In a further embodiment, at least about 50% of the grain germinates within 3 days following imbibition under typical conditions as used in malting.

In another aspect, the present invention provides a barley plant which produces grain, wherein flour produced from the grain comprises less than about 0.4% hordeins, and/or malt produced from the grain comprises less than about 200 ppm hordeins.

In another aspect, the present invention provides grain of a barley plant of the invention.

In a further aspect, the present invention provides a method of producing barley grain, the method comprising;
 a) growing a barley plant of the invention,
 b) harvesting the grain, and
 c) optionally processing the grain.

Preferably, the plants are grown on a commercial scale in a field. For example, in one embodiment, the method comprises growing at least 1,000, more preferably at least 5,000, plants in a field in an area of at least one hectare.

Also provided is a method of producing flour, wholemeal, starch or other product obtained from grain, the method comprising;
 a) obtaining grain of the invention, and
 b) processing the grain to produce the flour, wholemeal, starch or other product.

In a further aspect, the present invention provides a product produced from a barley plant of the invention or grain of the invention.

In an embodiment, the product is a food or malt-based beverage product.

Preferably, the malt-based beverage product is beer or whiskey.

In another embodiment, the product is a non-food product, preferably comprising starch or consisting of at least about 50% starch. Examples include, but are not limited to, films, coatings, adhesives, paper, building materials and packaging materials, or non-starch products such as ethanol.

In yet another aspect, the present invention provides a food or malt-based beverage produced using a method of the invention.

In an embodiment, the malt-based beverage is beer which comprises at least about 2%, more preferably at least about 4%, alcohol. Preferably, the alcohol is ethanol.

In yet a further embodiment, the malt-based beverage is beer which comprises less than about 1ppm hordeins.

In another aspect, the present invention provides beer comprising one or more barley grain proteins and less than about 1 ppm hordeins. In an embodiment, the beer has less than about 0.05 ppm hordeins.

Preferably, the beer comprises at least about 2%, more preferably at least about 4%, alcohol. Preferably, the alcohol is ethanol.

Examples of barley grain proteins include, but are not limited to, 9 kDa lipid barley protein 1 (LTP1) and protein Z.

In another aspect, the present invention provides flour comprising one or more barley grain proteins and less than about 0.4% hordeins.

In an embodiment, the flour comprises less than about 0.3%, less than about 0.2% and more preferably less than about 0,1% hordeins.

Preferably, the flour comprises less than about 7 mg, more preferably less than about 5 mg, of alcohol soluble protein/gm dry weight flour.

In yet another aspect, the present invention provides malt comprising one or more barley grain proteins and less than about 200ppm hordeins.

In an embodiment, the malt comprises less than about 125 ppm hordeins, more preferably less than about 75 ppm hordeins.

In a further aspect, the present invention provides a method for identifying barley grain which can be used to produce a food and/or malt-based beverage for consumption by a subject with coeliac's disease comprising
 a) obtaining one or more of the following materials;
  i) a sample from a plant capable of producing said grain,
  ii) the grain,
  iii) malt produced from the grain, and/or
  iv) an extract of said grain,
 b) analysing the material from step a) for at least one hordein and/or at least one gene encoding a hordein,
wherein the greater the amount of hordeins produced by the grain the less suitable the grain is for producing a food and/or malt-based beverage for consumption by a subject with coeliac's disease.

In an embodiment, the sample is grain and step b) comprises analysing the material for B and/or C hordeins. This can be performed using any technique known in the art, for example using an immunological method such as ELISA assays. The method described in Example 1 can be used. In an embodiment, step b) comprises orally administering the material from step a) to a subject with coeliac's disease and determining the immunoreactivity of T cells obtained from the subject to one or more barley hordeins.

In another embodiment, the sample material from step a) comprises genomic DNA and step b) comprises detecting the absence of one or more functional hordein genes. Again, this can be performed using any technique known in the art. For example, performing a gene amplification step as outlined in Example 9.

In an embodiment, the method comprises the step of selecting a barley plant, grain or malt according to the invention from a plurality of plants, grains or malts for propagation or use, Such selection is based, directly or indirectly, on the reduced coeliac toxicity of the material.

In a further aspect, the present invention provides a method of preventing or reducing the incidence or severity of coeliac's disease in a subject, the method comprising orally administering to the subject a food or malt-based beverage of the invention, or a grain of the invention. Reduced incidence or severity of disease in this context is understood to be relative to administering an equal amount of food or beverage prepared from wild-type barley. The food or beverage may be used to provide nutrients, or an increased amount of nutrients, to a subject having coeliac disease while lessening the risk of triggering disease symptoms.

In another aspect, the present invention provides for the use of a food or malt-based beverage of the invention, or a grain of the invention, for the manufacture of a medicament for orally administering to a subject nutrients while at the same time preventing or reducing the incidence or severity of coeliac's disease.

As will be apparent, preferred features and characteristics of one aspect of the invention are applicable to any other aspect of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1: Reverse-phase FPLC of total prolamin extracts, showing the A280 nm chromatograms from wheat (a), barley (b), oats (c); maize (d) or a blank gradient (e). Prolamins equivalent to 0.2 g flour were loaded. Oxidised DTT is shown ($DTT_{ox}$); chromatograms have been offset for clarity.

Figure 2:
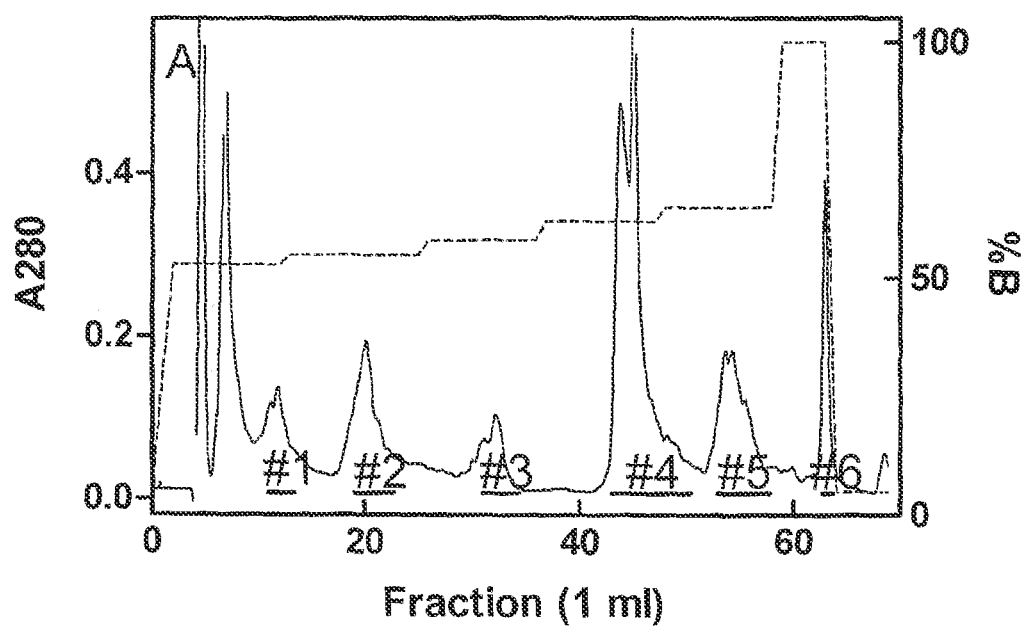

FIG. 2: Reverse-phase FPLC of hordeins. A representative chromatogram showing the A280 nm (solid line) and solvent composition (broken line) during isolation of hordein fraction 1 (#1), 2 (#2), 3 (#3), 4 (#4), 5 (#5), or 6 (#6) from a barley extract. The indicated fractions were pooled as shown (bold line) from sequential injections.

Figure 3:

FIG. 3: Analysis of 20 μg of hordein fractions #1-6 by SDS-PAGE, staining the gel with 0.06% Coomassie Blue G250. The position of molecular weight standards (in kDa, BenchMark, Invitrogen) are indicated in the left hand lane.

Figure 4:
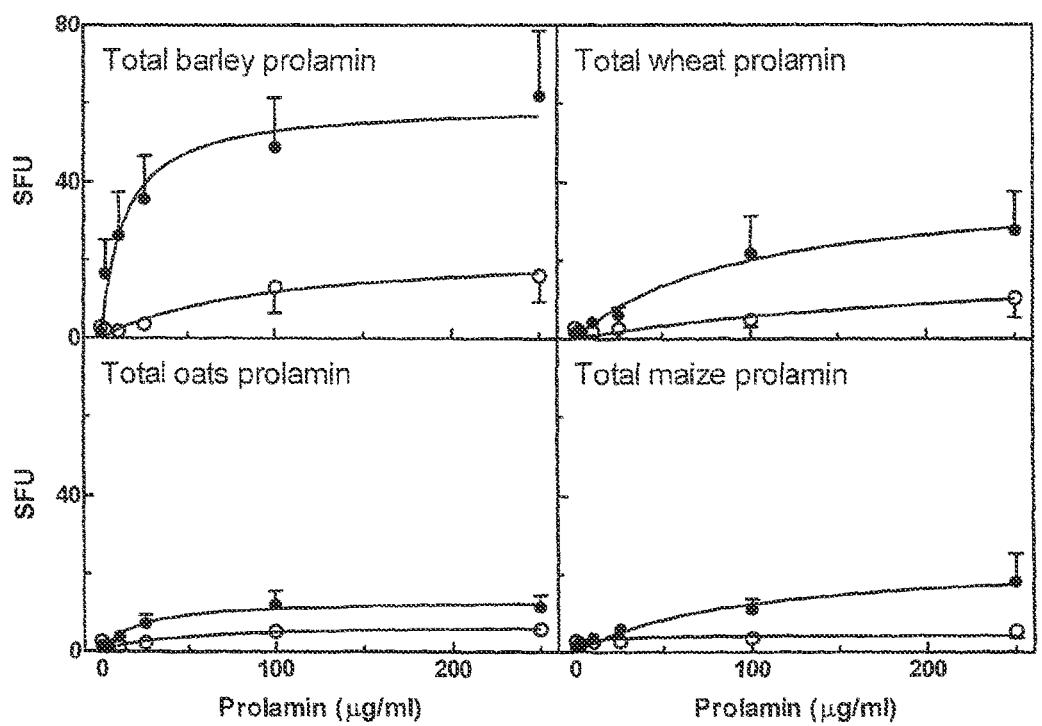

FIG. 4: The stimulation of IFN-γ production in T-cells, isolated from coeliacs six days after a dietary challenge, by total prolamin preparations from barley, wheat, oats or maize in the presence (●, n=21)), or absence (○, n=13) of tTG pre-treatment. IFN-γ positive colonies were counted and presented as mean SFU±S.E. Error bars are not shown when S.E. was smaller than symbols.

Figure 5:
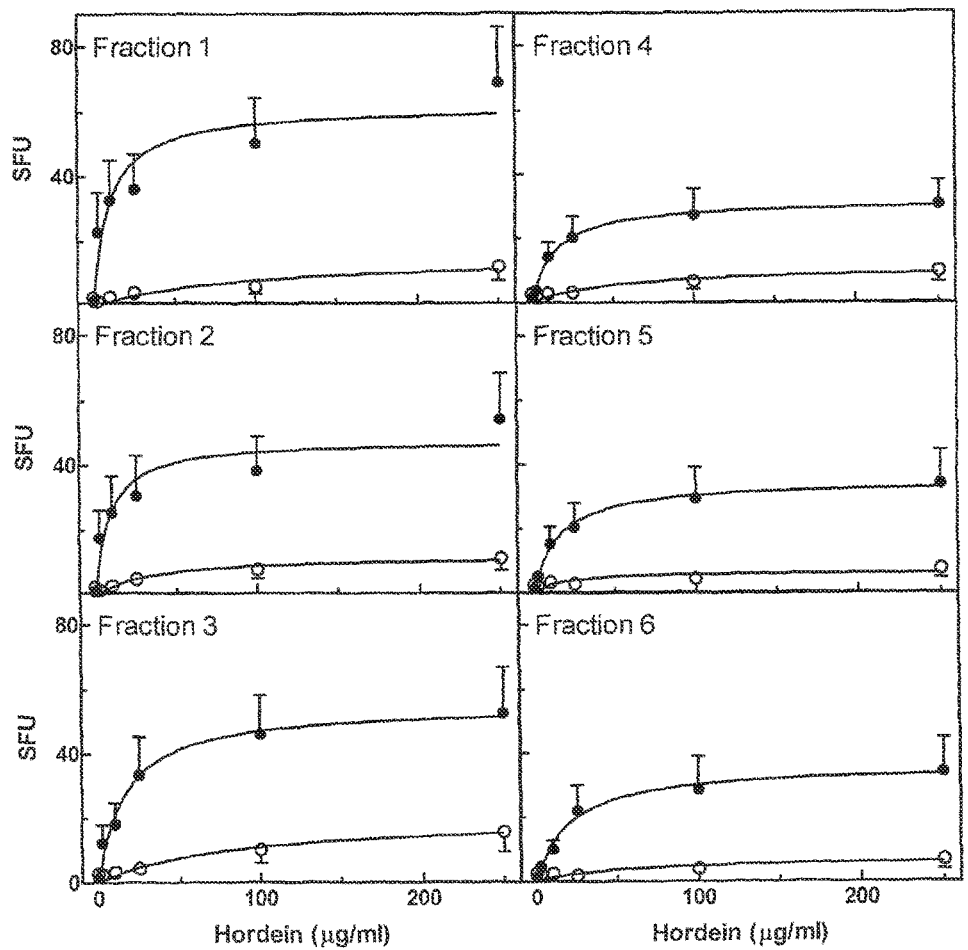

FIG. 5: The stimulation of IFN-γ production in T-cells, isolated from coeliacs six days after a dietary challenge, by hordein fractions #1, 2, 3, 4, 5, and 6, in the presence (●, n=21)), or absence (○, n=13) of tTG pre-treatment. IFN-γ positive colonies were counted and presented as mean SFU±S.E. Error bars are not shown when S.E. was smaller than symbols.

Figure 6:
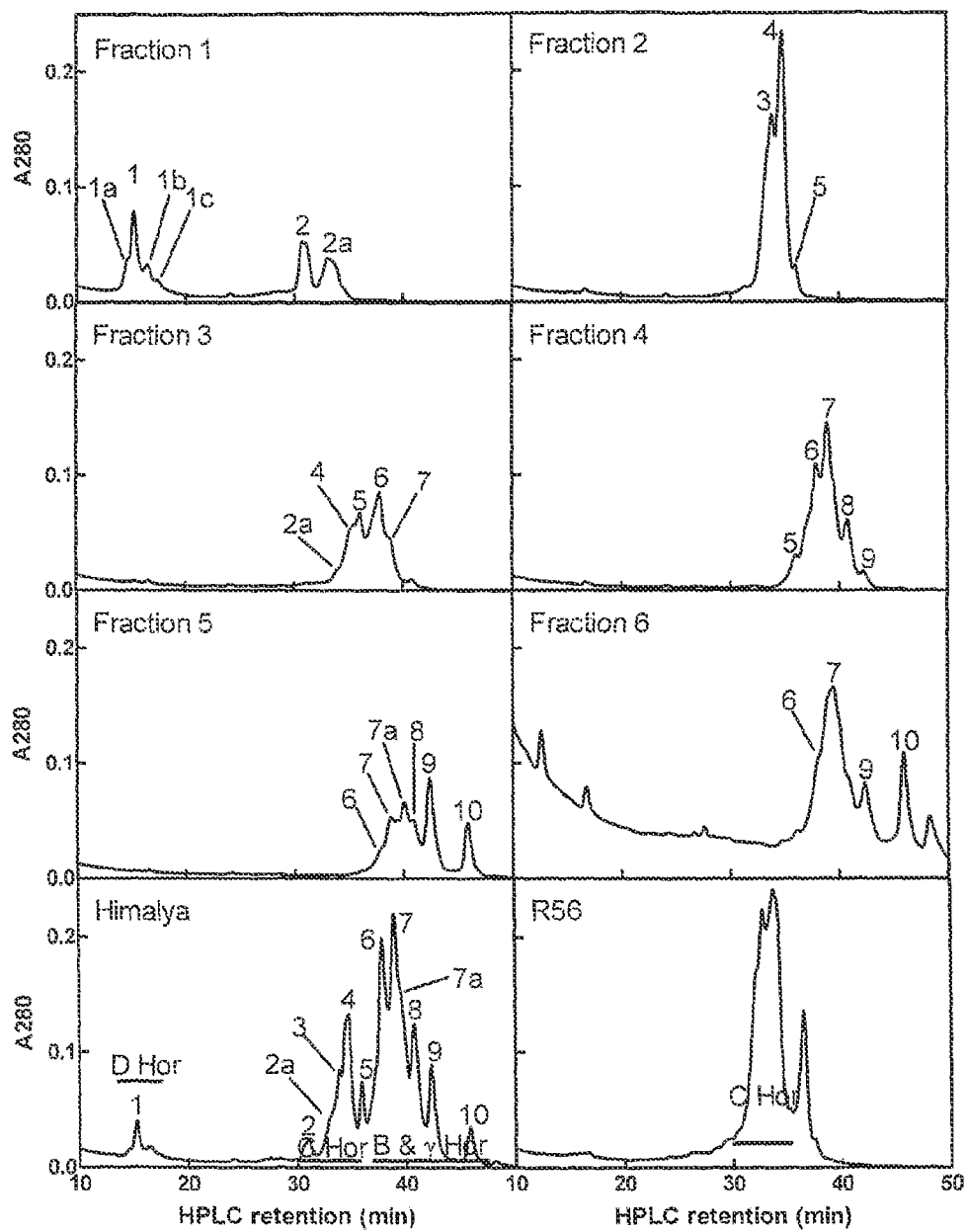

FIG. 6: Analytical reverse-phase HPLC chromatograms of the isolated hordein fractions. Representative chromatograms showing the A280 nm during HPLC of hordein fractions #1, 2, 3, 4, 5, 6 purified from barley. For comparison, chromatograms are shown for wild-type barley (Himalaya) showing the elution (solid line) of D, C, and B hordeins, as well as the mutant 156 which accumulates mainly C hordeins.

Figure 7:
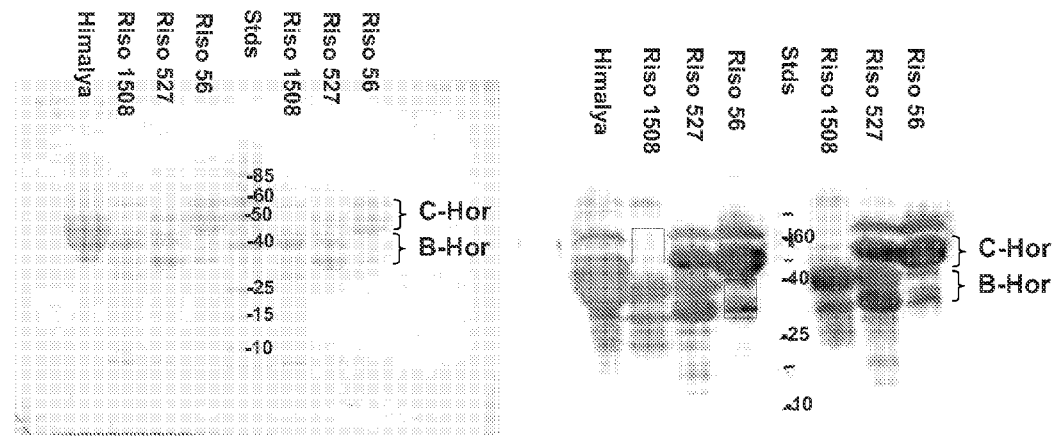

FIG. 7: Characterization of the prolamins in Riso56 and Riso1508 by SDS-PAGE and western blotting. Twenty μg of prolamin, purified as in Example 1, from the indicated barley line was incubated for 30 min at room temperature in a buffer containing 6.6 M urea, 2% (w/v) SDS, 1% (w/v) DTT, 62.5 mM Tris-HCl (pH 6.8), and 0.01% (w/v) bromophenol blue and loaded on duplicate 12% acrylamide gels and electrophoresed at 200 V for 40 min. The gel was rinsed in transfer buffer containing 192 mM Glycine, 25 mM Tris-base, and 20% (v/v) methanol for 10 min and transferred to nitrocellulose (Amersham Hybond C+) at 100 V for 1 hr. The left hand membrane was stained in 0.2% (w/v) Ponceau S in 3% (w/v) trichloroacetic acid, 3% 5-sulphosalicylic acid and destained briefly in water; the right hand membrane was blocked in 5% skim milk in PBST for 1 hr, then incubated with mouse monoclonal antibody 12224 (Skerrit, 1988) in PBST, washed in PBST for 3×10 minutes, incubated in sheep anti-mouse-HRP (Selenius) in PBST, washed in PBST 3×5 min, incubated in Amersham ECL reagent as in the manufacturers instructions, and exposed to Amersham Hyperfilm. MAb 12224 was raised against a total glutenin extract and is detects all hordeins and prolamins (Skerrit, 1988).

Figure 8:
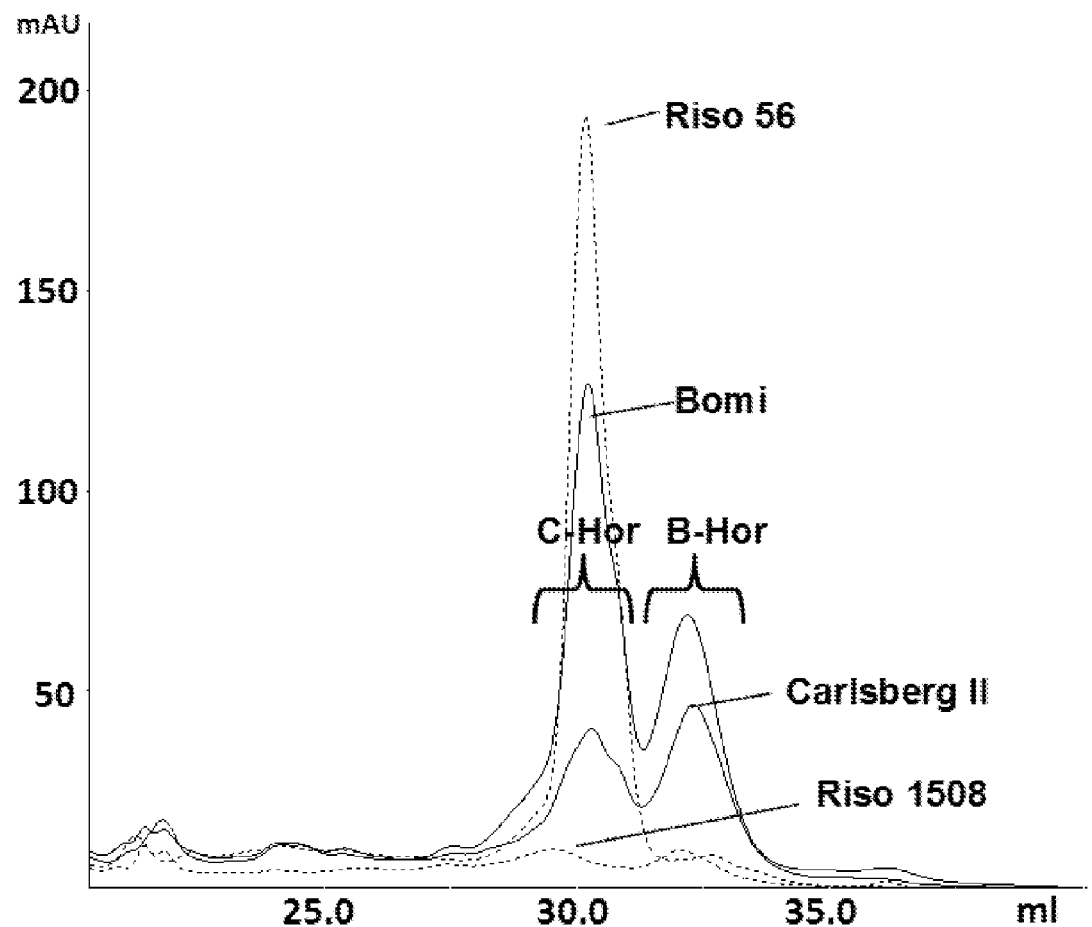

FIG. 8: Reverse phase FPLC of hordein extracts in Riso56 and Riso1508 compared to wild-type Bomi and Carlsberg II. Hordeins were purified from the indicated lines as in Example 1, and an amount equivalent to 0.2 g flour was injected onto an FPLC column using the first FPLC method in Example 1. The elution time of C-hordein (C-Hor) and B-hordein (B-Hor) is indicated.

Figure 9:
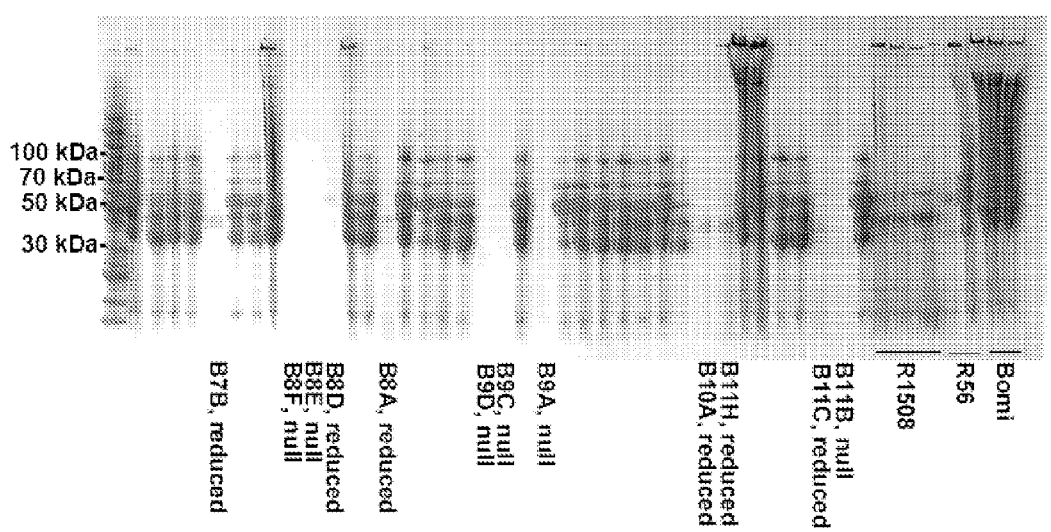

FIG. 9: Representative SDS-PAGE of alcohol soluble proteins loaded on a per seed basis. Prolamin extracts (10 μl) from individual F2 barley seeds from a cross between Riso1508 and Riso56 were extracted as described above. The positions of protein standards of 30, 50, 70 and 100 kDa are indicated on the left hand lane. The protein profiles of the parental lines Riso1508 and Riso56, and wild type (Bomi) are also shown. Six lanes from putative double nulls contain very little protein (null), six other lanes contain much reduced levels of protein (reduced).

Figure 10:
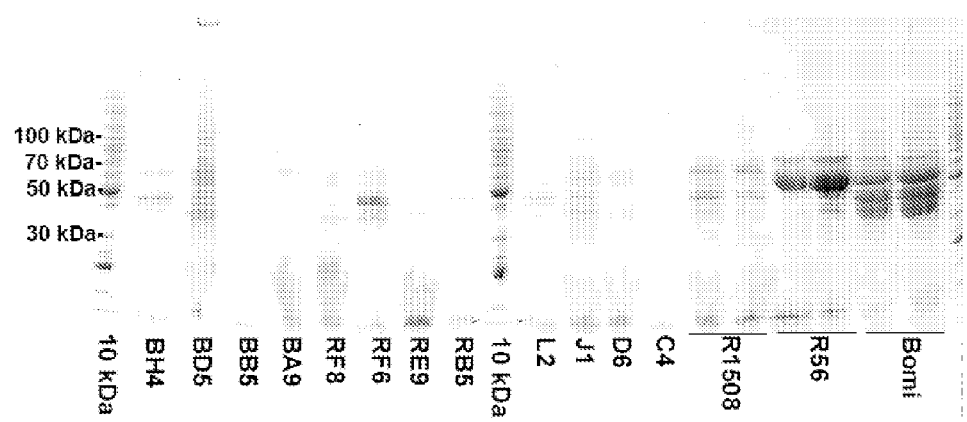

FIG. 10: Representative SDS-PAGE of alcohol-soluble proteins loaded on an equal protein basis. Samples containing 20 μg of alcohol-soluble protein extracted from individual F2 barley seeds were electrophoresed and the gel stained with Coomassie blue. Samples from the parental lines (Riso 1508 and Riso 56) and wild type (Bomi) are also run. The outermost and center lanes (10 kDa) contained protein standards of known molecular weights, the positions for bands of 30, 50, 70 and 100 kDa are indicated.

Figure 11:
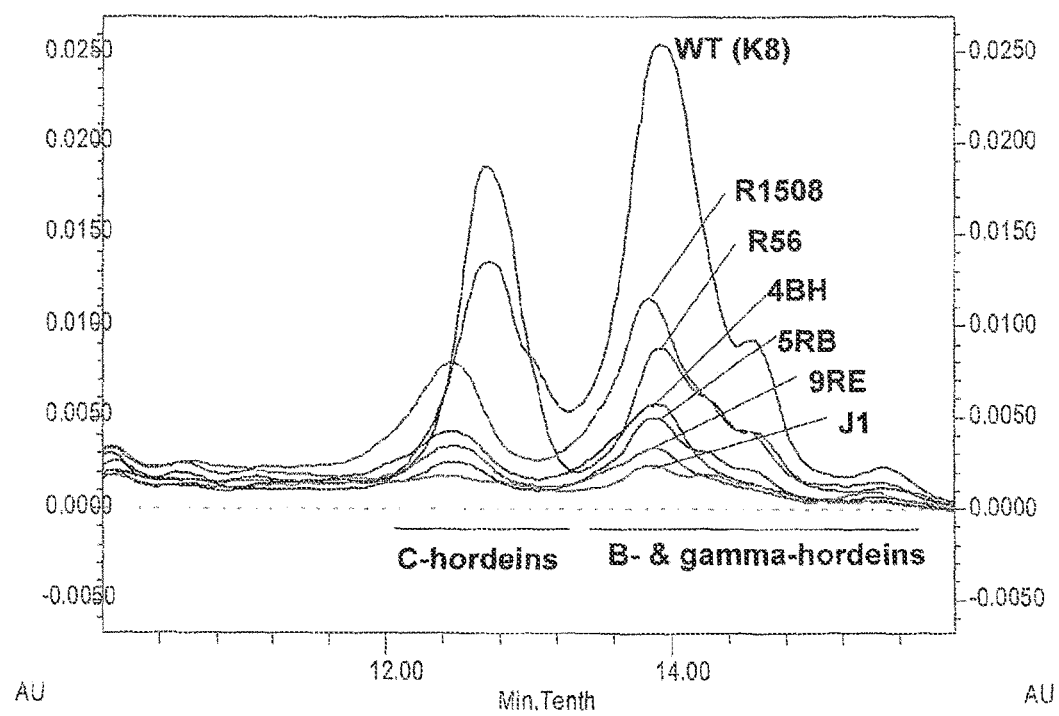

FIG. 11: RP-FPLC chromatograms of alcohol soluble extracts from F3 barley seeds. Alcohol soluble proteins were extracted from individual F3 seeds as described; the supernatants from two seeds were combined from each line and 50 μl injected onto a reverse phase FPLC column and eluted as described in Example 1.

Figure 12:
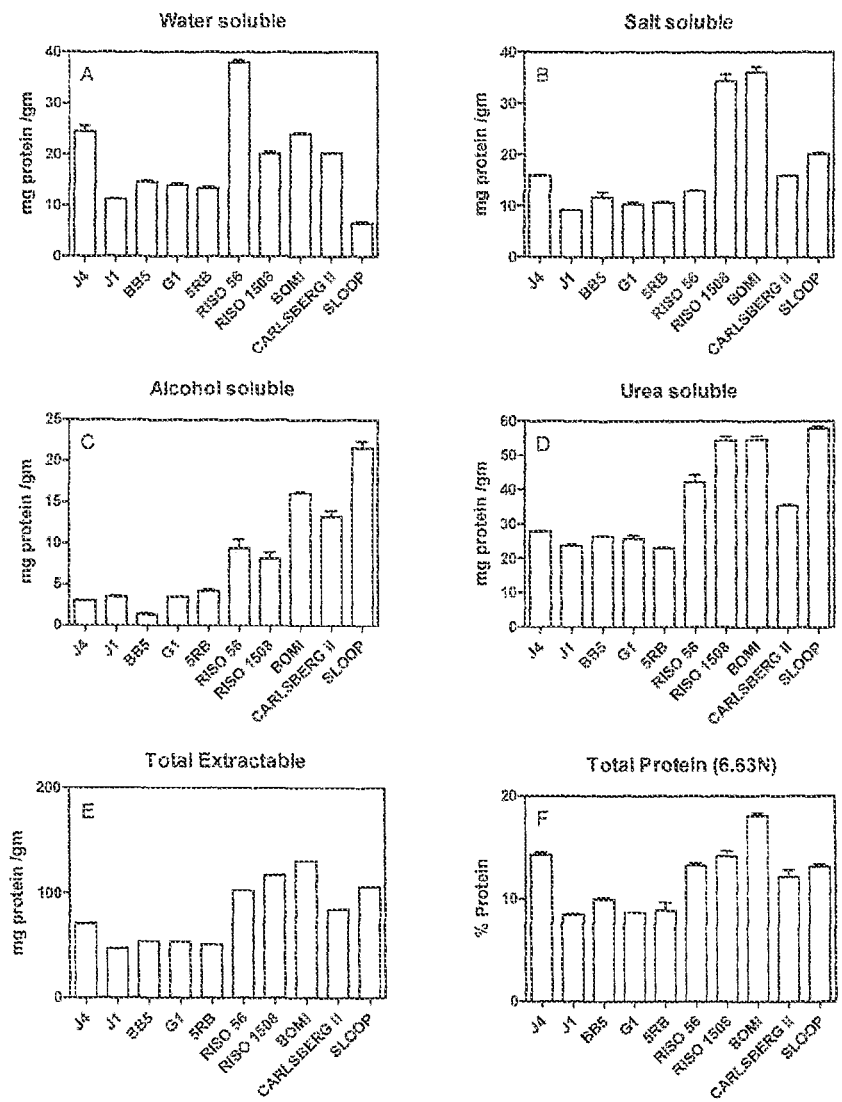

FIG. 12: The content of water soluble (A), salt soluble (B), alcohol soluble (C) and urea soluble (D) protein in duplicate flour samples from wild type barley (Sloop, Carlsberg II, Bomi), the single null parents (Riso 56, Riso 1508) and F4 seeds of the plants of lines J4, J1, BB5, G1, 5RB was determined as in Example 4. The total extractable protein (E) content was determined by summing the content of the individual fractions. The total protein content was also estimated by elemental analysis according to the method of Dumas (F). Protein contents are shown as the mean±SE.

Figure 13:
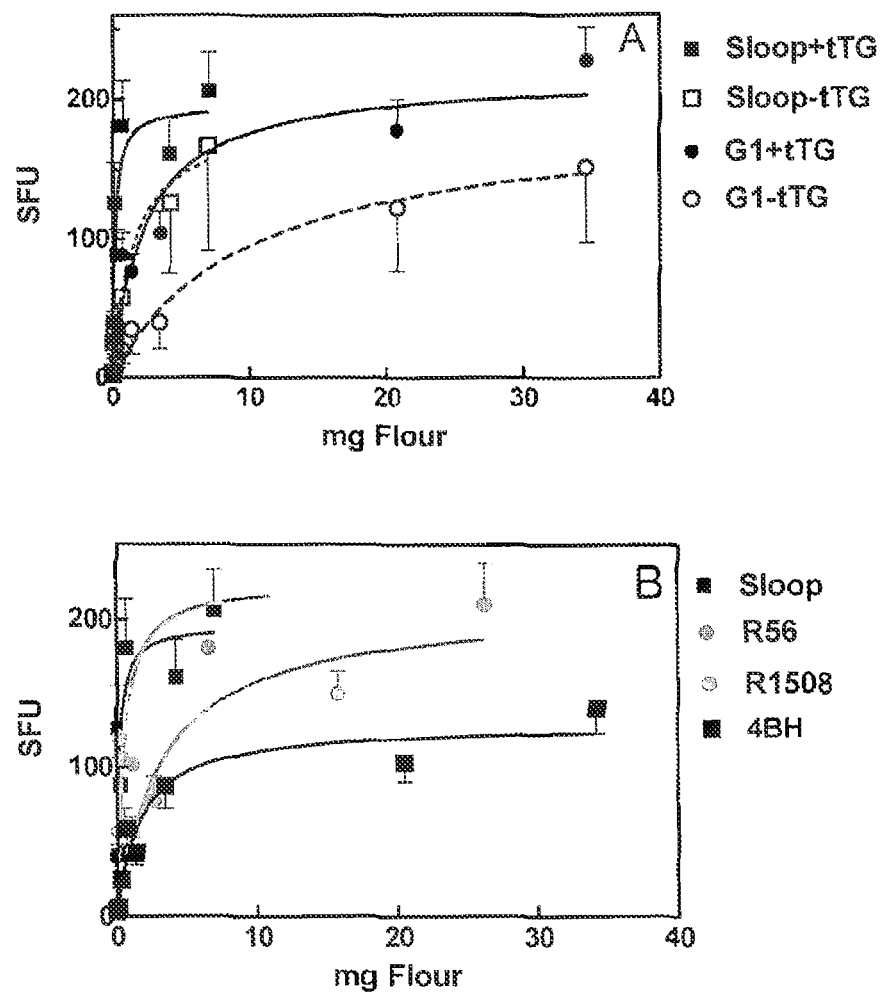

FIG. 13: The coeliac toxicity of hordeins purified from various flour samples was determined with T-cells isolated from coeliacs, 6 days post challenge, as in Example 5, and the mean spot forming units (SFU)±SE plotted vs the fresh weight of flour. For clarity, mean SFU are shown only for hordeins purified from wild type barley (Sloop) or the double null line (G1) in the presence (+tTG) or absence (−tTG) of the enzyme, tissue transglutaminase (A). In all cases treatment with tTG increased the toxicity of hordeins as expected for coeliac disease. SFU are also shown for tTG treated hordeins (B) purified from flour samples of wild-type barley (Sloop), the single null parents (R56, R1508) and F4 seeds (4BH).

Figure 14:
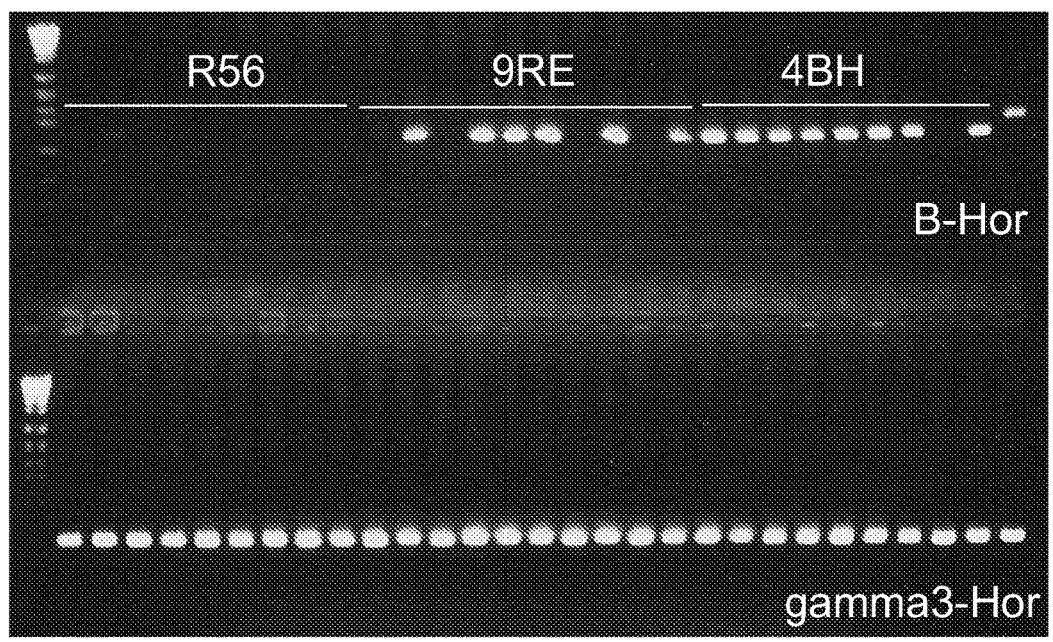

FIG. 14: Gene sequences specific for either the control gene (gamma3-Hor), or the B-hordein gene (B-Hor) were amplified from DNA extracts of individual F4 seedlings of either the lines 9RE, 4BH or the parent line R56 as in Example 9.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in plant breeding, food technology, cell culture, molecular genetics, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and S. D. Hames (editors), DNA Cloning: A Practical Approach, Volumes 1-4, IRL Press (1995 and 1996), and F. M. Ausubel at al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al, (editors) Current Protocols in Immunology, John Wiley & Sons (including all updates until present).

As used herein, the term "barley" refers to any species of the Genus *Hordeum*, including progenitors thereof, as well as progeny thereof produced by crosses with other species. A preferred form of barley is the species *Hordeum vulgare*.

Coeliac disease or celiac disease is an autoimmune disorder of the small intestine that occurs in genetically predisposed individuals in all age groups after early infancy. It affects approximately 1% of Indo-European populations, though it is significantly underdiagnosed. Coeliac disease is caused by a reaction to gliadin, a gluten protein found in wheat (and similar proteins of Triticeae which includes other cultivars such as barley and rye). Upon exposure to gliadin, the enzyme tissue transglutaminase modifies the protein, and the immune system cross-reacts with the bowel tissue, causing an inflammatory reaction. This leads to flattening of the lining of the small intestine, which interferes with the absorption of nutrients. The only effective treatment is a lifelong gluten-free diet. This condition has several other names, including: coeliac disease (with ligature), c(o)eliac sprue, non-tropical sprue, endemic sprue, gluten enteropathy or gluten-sensitive enteropathy, and gluten intolerance. The symptoms of coeliac disease vary widely from person to person. Symptoms of coeliac's disease may include one or more of the following; gas, recurring abdominal bloating and pain, chronic diarrhea, constipation, pale, foul-smelling, or fatty stool, weight loss/weight gain, fatigue, unexplained anemia (a low count of red blood cells causing fatigue), bone or joint pain, osteoporosis, osteopenia, behavioral changes, tingling numbness in the legs (from nerve damage), muscle cramps, seizures, missed menstrual periods (often because of excessive weight loss), infertility, recurrent miscarriage, delayed growth, failure to thrive in infants, pale sores inside the mouth, called aphthous ulcers, tooth discoloration or loss of enamel, and itchy skin rash called dermatitis herpetiformis. Same of the more common symptoms include; tiredness, intermittent diarrhoea, abdominal pain or cramping, indigestion, flatulence, bloating; and weight loss. Ceoliac's disease can be diagnosed, for example, as described in WO 01/025793.

As used herein, the term "non-toxic to a subject with coeliac's disease" refers to the consumption of food or a beverage not resulting in the development of a symptom of coeliac's disease in a subject suffering from said disease. As described herein, the food or beverage made from a corresponding wild-type barley plant does result in disease symptoms.

The terms "seed" and "grain" are used interchangeably herein. "Grain" generally refers to mature, harvested grain but can also refer to grain after processing such as, for example, milling or polishing, where most of the grain stays intact, or after imbibition or germination, according to the context. Mature grain commonly has a moisture content of less than about 18-20%. Wild-type barley grain (whole grain) generally contains 9-12% protein, and about 30-50% of this is prolamin, typically 35%, so wild-type barley grain has about 3-4% prolamin by weight. Prolamine are found almost exclusively in the endosperm, which is about 70% of the wholegrain weight.

As used herein, the term "corresponding wild-type" barley plant refers to a plant which comprises at least 50%, more preferably at least 75%, more preferably at least 95%, more preferably at least 97%, more preferably at least 99%, and even more preferably 99.5% of the genotype of a plant of the invention, but produces grain with unmodified hordein levels. In one embodiment, the "corresponding wild-type" barley plant is a cultivar used in plant breeding experiments to introduce genetic variants that result in reduced hordein production in the grain. In another embodiment, the "corresponding wild-type" barley plant is a parental cultivar into which a transgene has been introduced which reduces hordein production in the grain. In a further embodiment, the "corresponding wild-type" barley plant is a cultivar that is used at the date of filing for the commercial production of barley grain such as, but not limited to, Bomi, Sloop, Carlsberg II, K8, L1, Vlamingh, Stirling, Hamelin, Schooner, Baudin, Gairdner, Buloke, WI3586-1747, WI3416, Flagship, Cowabbie, Franklin, SloopSA, SloopVic, Quasar, VB9104, Grimmett, Cameo*Arupo 31-04, Prior, Schooner, Unicorn, Harrington, Torrens, Galleon, Morex, Dhow, Capstan, Fleet, Keel, Maritime, Yarra, Dash, Doolup, Fitzgerald, Molloy, Mundah, Onslow, Skiff, Unicorn, Yagan, Chebec, Hindmarsh, Chariot, Diamant, Korál, Rubín, Bonus, Zenit, Akcent, Forum, Amulet, Toler, Heris, Maresi, Landora, Caruso, Miralix, Wikingett Brise, Caruso, Potter, Pasadena, Annabell, Maud, Extract, Saloon, Prestige, Astoria, Elo, Cork, Extract, Laura. In an embodiment, the "corresponding wild-type" barley plant produces grain with unmodified hordein levels due to it comprising a full complement of functional hordein genes encoding functional hordein proteins, including the B, C, D and γ-hordeins encoded by the Hor2, Hor1, Hor3, and Hor5 loci.

As used herein, the term "one or more barley grain proteins" refers to naturally occurring proteins produced by barley grain. Examples of such proteins are known to those skilled in the art. Specific examples include, but are not limited to, barley albumins such as the 9 kDa lipid transfer protein 1 (LIP1) (see Douliez et al. (2000) for a review and Swiss-prot Accession No. P07597 as an example) and protein Z (see Brandt et al. (1990) and Genbank Accession No. P06293), including processed (mature) forms thereof, as well as denatured forms and/or fragments thereof produced as a result of the production of malt, flour, wholemeal, food or malt-based beverage of the invention.

As used herein, the term "malt" is used to refer to barley malt, "flour" to refer to barley flour, "wholemeal" to refer to barley wholemeal, and "beer" to refer to barley beer. More specifically, a source of malt, flour, beer, wholemeal, food product etc of the invention is from the processing (for example, milling and/or fermentation) of barley grain. These terms include malt, flour, beer, wholemeal, food product etc produced from a mixture of grains. In a preferred embodiment, at least 50% of the grain used to produce the malt, flour, beer, wholemeal, food product etc is barley grain.

The term "plant" as used herein as a noun refers to a whole plant such as, for example, a plant growing in a field for commercial barley production. A "plant part" refers to plant vegetative structures (for example, leaves, stems), roots, floral organs/structures, seed (including embryo, endosperm, and seed coat), plant tissue (for example, vascular tissue, ground tissue, and the like), cells, starch granules or progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

"Nucleic acid molecule" refers to a polynucleotide such as, for example, DNA, RNA or oligonucleotides. It may be DNA or RNA of genomic or synthetic origin, double-stranded or single-stranded, and combined with carbohydrate, lipids, protein, or other materials to perform a particular activity defined herein.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic faint or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide, The term "gene" includes a synthetic or fusion molecule encoding all or part of the proteins of the invention described herein and a complementary nucleotide sequence to any one of the above.

As used herein, the term "other food or beverage ingredient" refers to any substance suitable for consumption by an animal, preferably any substance suitable for consumption by a human. Examples include, but are not limited to, water, grain from other plant species, sugar, etc.

As used herein, the term "genetic variation which each results in reduced levels of at least one hordein" refers to any polymorphism of a barley plant that reduces hordein production. The genetic variation may be, for example, a deletion of a hordein gene(s) or part thereof, or a mutation which reduce barley gene transcription. Examples of such genetic variations are present in Riso 56, Riso 527 and Riso 1508. Hence, such plants may be used for the methods of the invention. Furthermore, a plant of the invention may be a cross between any of these barley mutants. In a preferred embodiment, a plant of the invention is a cross between Riso 56 and Riso 1508 or progeny thereof comprising the hor2 and lys3 mutations present in these lines. In an embodiment, the plant is not a cross between Riso 527 and Riso 1508.

As used herein, unless stated to the contrary, the phrase "about" refers to any reasonable range in light of the value in question. In a preferred embodiment, the term "about" refers to +/−10%, more preferably +/−5%, of the specified value.

Prolamins and Hordeins

Cereal prolamins (known as gliadins in wheat, hordeins in barley, secalins in rye, avenins in oats, and zeins in maize) are the main endosperm storage proteins in all cereal grains, with the exception of oats and rice (Shewry and Halford, 2002). Hordeins represent 35-50% of the total protein in barley seeds (Jaradat, 1991). They are classified into four groups, A (also known as γ hordein), B, C, and D, in order of decreasing mobility (Field et al., 1982). The B hordeins are the main protein fraction, differing from C hordeins in their sulphur content (Kreis and Shewry, 1989). B hordeins account for 70-80% of the total and C hordeins for 10-20% (Davies et al., 1993). The A hordeins are not generally considered to be a storage fraction whereas D hordeins are homologous to the high-molecular-weight glutenins. Hordeins, along with the rest of the related cereal prolamin, are not expressed in the zygotic embryo itself, unlike other storage proteins such as napins; they are believed to be expressed exclusively in the starchy endosperm during the middle-to-late stages of seed development.

Examples of barley hordein amino acid sequences (provided as Accession No; description in NCBI; gi details) include, but are not necessarily limited to, 1103203A; hordein B; gi|224385|prf||1103203A[224385]; 1103203B; hordein B; gi|224386|prt||1103203B[224386]1103203C; hordein C; gi|224387|prf||1103203C[224387]1210226A; hordein B1; gi|225171|prf||1210226A[225171]1307151A; hordein C; gi|225588|prf||1307151A[225588]130715113; hordein C; gi|225589|prf||1307151B[225589]1604464A;

gamma hordein; gi|226755|prf||1604464A [226755] AAA32942; C-hordein; gi|67016|gb|AAA32942.1| [167016]AAA32943; C-hordein storage protein; gi|167018|gb|AAA32943.1|[167018]AAA32944; C-hordein storage protein; gi|167020|gb|AAA32944.1|[167020] AAA32955; gamma-1 hordein precursor; gi|167042|gb|AAA32955.1|[167042]AAA32967; hordein; gi|530093|gb|AAA32967.1|[530093]AAA92333; C. hordein; gi|893242|gb|AAA92333.1|[893242]AAB28161; C. hordein [*Hordeum vulgare*]; gi|442524|gb|AAB28161.1||bbm|3247521bbs|139926 [442524]AAB71678; seed storage protein [*Hordeum vulgare*]; gi|2454599|gb|AAB71678.1|[2454599]AAB71679; seed storage protein [*Hordeum vulgare*]; gi|2454600|gb|AAB71679.1|[2454600]AAP31050; globulin [*Hordeum vulgare*]; gi|30421166|gb|AAP31050.1| [30421166]AAP31051; D-Hordein [*Hordeum vulgare*]; gi|30421167|gb|AAP31051.1|[30421167]AAQ63842; gamma 3 hordein [*Hordeum chilense*]; gi|34329251|gb|AAQ63842.1|[34329251]AAQ63843; gamma 3 hordein [*Hordeum chilense*]; gi|34329253|0|AAQ63843.1|[34329253]AAQ63844; gamma 3 hordein [*Hordeum chilense*]; gi|34329255|gb|AAQ63844.11[34329255]AAQ63845; gamma 3 hordein [*Hordeum chilense*]; gi|34329257|gb|AAQ63845.1|[34329257]AAQ63846; gamma 3 hordein [*Hordeum chilense*]; gi|34329259|gb|AAQ63846.1|[34329259]AAQ63847; gamma 3 hordein [*Hordeum chilense*]; gi|34329261|gb|AAQ63847.1|[34329261]AAQ63848; gamma 3 hordein [*Hordeum chilense*]; gi|34329263|gb|AAQ63848.1|[34329263] AAQ63849; gamma 3 hordein [*Hordeum chilense*]; gi|34329265|gb|AAQ63849.1|[34329265]AAQ63850; gamma 3 hordein [*Hordeum chilense*]; gi|34329267|gb|AAQ63850.1|[134329267]AAQ63851; gamma 3 horde in [*Hordeum chilense*]; gi|34329269|gb|AAQ63851.1|[34329269]AAQ63852; gamma 3 hordein [*Hordeum chilense*]; gi|34329271|gb|AAQ63852.1|[34329271]AAQ63853; gamma 3 hordein [*Hordeum chilense*]; gi|34329273|gb|AAQ63853.1|[34329273]AAQ63854; gamma 3 hordein [*Hordeum chilense*]; gi|34329275|gb|AAQ63854.1|[34329275]AAQ63855; gamma 3 hordein [*Hordeum chilense*]; gi|34329277|gb|AAQ63855.1|[34329277]AAQ63866; gamma 3 hordein [*Hordeum chilense*]; gi|34329299|gb|AAQ63866.1|[34329299]AAQ63867; gamma 3 hordein [*Hordeum chilense*]; gi|34329301|gb|AAQ63867.1|[34329301]AAQ63868; gamma 3 hordein [*Hordeum chilense*]; gi|34329303|gb|AAQ63868.1|[34329303]AAQ63869; gamma 3 hordein [*Hordeum chilense*]; gi|34329305|gb|AAQ63869.1|[34329305]AAQ63870; gamma 3 hordein [*Hordeum chilense*]; gi|34329307|gb|AAQ63870.1|[34329307]AAQ63871; gamma 3 hordein [*Hordeurn chilense*]; gi|34329309|gb|AAQ63871.1|[34329309]AAQ63872; gamma 3 hordein [*Hordeum chilense*]; gi|34329311|gb|AAQ63872.1|[34329311]AAU06227; B hordein [*Hordeum brevisubulatum* subsp. *turkestanicum*]; gi|51556914|gb|AAU06227.1|[51556914]AAU06228; B hordein [*Hordeum brevisubulatum* subsp. *turkestanicum*]; gi|51556916|gb|AAU06228.1|[51556916]AAU06229; B hordein [*Hordeurn brevisubulatum* subsp. *turkestanicum*]; gi|51556918|gb|AAU06229.1|[51556918]AAZ76368; B hordein [*Hordeum vulgare* subsp. *vulgare*]; gi|73427781|gb|AAZ76368.1|[73427781]ABA06537; B hordein [*Hordeum vulgare* subsp. *vulgare*]; gi|74422695|gb|ABA06537.1|[74422695]ABB82613; 13 hordein [*Hordeum vulgare* subsp. *vulgare*]; gi|82548223|gb|ABB82613.1|[82548223]ABB82614; B hordein [*Hordeum vulgare* subsp. *vulgare*]; gi|82548225|gb|ABB82614.1|[82548225]ABH01262; B hordein [*Hordeum vulgare* subsp. *vulgare*]; gi|110832715|gb|ABH01262.1|[110832715]BAA11642; D hordein [*Hordeum vulgare* subsp. *vulgare*]; gi|11674981dbj|BAA11642.1|[1167498]CAA25509; unnamed protein product [*Hordeum vulgare*]; gi|18907|emb|CAA25509.1|[18907]CAA25912; unnamed protein product [*Hordeum vulgare*]; gi|18914|emb|CAA25912.1|[18914]CAA25913; unnamed protein product [*Hordeum vulgare*]; gi|829269|emb|CAA25913.1|[829269]CAA25914; unnamed protein product[*Hordeum vulgare*]; gi|18949|emb|CAA25914.1|[18949]CAA26889; unnamed protein product [*Hordeum vulgare*]; gi|18910|emb|CAA26889.1|[18910]CAA31861; unnamed protein product [*Hordeum vulgare* subsp. *vulgare*]; gi|18980|emb|CAA31861.1|[18980]CAA37729; B hordein precursor [*Hordeum vulgare* subsp. *vulgare*]; gi|18929|emb|CAA37729.1|[18929]CAA42642; unnamed protein product [*Hordeum vulgare* subsp. *vulgare*]; gi|19001|emb|CAA42642.1|[19001]CAA48209; D hordein [*Hordeum vulgare* subsp. *vulgare*]; gi|89701|emb|CAA48209.1|[18970]CAA5 gamma 3 hordein [*Hordeum vulgare*]; gi|288709|emb|CAA51204.1| [288709]CAA59104; D-hordein [*Hordeum vulgare* subsp. *vulgare*]; gi|671537|emb|CAA59104.1|[671537] CAA60681; B1 hordein [*Hordeum vulgare*]; gi|809031|emb|CAA60681.1|[809031]CAE45747; putative gamma 2 hordein [*Hordeum vulgare*]; gi|34365052|emb|CAE45747.1|[34365052]P06470; B1-hordein precursor; gi|123458|sp|P06470|HOR1_HORVU[123458]P06471; B3-hordein; gi|123459|sp|P06471|HOR3_HORVU [123459]P06472; C-hordein (PCP387); gi|123460|sp|P06472|HOR7_HORVU[123460]P17990; Gamma-hordein-1 precursor; gi|23464|sp|P17990|HOG1_HORVU[123464]P17991; C-hordein (Clone PC HOR1-3); gi|123461|sp|P17991|HOR8_HORVU[123461]P17992; C-hordein (Clone PC-919); gi|123462|sp|P17992|HOR9_HORVU[123462]P29835; 19 kDa globulin precursor (Alpha-globulin); gi|1155055531sp|P298351GL19_ORYSJ[115505553] P80198; Gamma-hordein-3; 17082801sp|P801981HOG3_HORVU[1708280]

Examples of genes and/or cDNAs encoding barley hordeins (provided as Accession No; description in NCBI; gi details) include, but are not necessarily limited to, AF016237; *Hordeum vulgare* seed storage protein (HORDB3a) mRNA, partial cds; gi|2454596|gb|AF016237.1|HVHORD1[2454596] AF016238; *Hordeum vulgare* seed storage protein (HORDB3a) mRNA 3' end sequence, partial cds; gi|2454597|gb|AF016238.1|HVHORD2[2454597] AH005570; *Hordeum vulgare* subsp. *vulgare* seed storage protein gene, partial cds; gi|2454598|gb|AH005570.11SEG_HVORDORD[2454598] AJ580585; *Hordeum vulgare* gamma-2hor gene for putative gamma 2 hordein; gi|34365051|emb|A1580585.1| [34365051]AY268139; *Hordeum vulgare* BAC 18409, complete sequence; gi|30421164|gb|AY268139.1|[30421164]

AY338365; *Hordeum chilense* clone 1 cultivar H1 gamma 3 hordein mRNA, complete cds; gi|34329250|gb|AY338365.1|[34329250]AY338366; *Hordeum chilense* clone 2 cultivar H1 gamma 3 hordein mRNA, complete cds; gi|34329252|gb|AY338366.1|[34329252] AY338367; *Hordeum chilense* clone 3 cultivar H1 gamma 3 hordein mRNA, complete cds; gi|34329254|gb|AY338367.1|[34329254]AY338368; *Hordeum chilense* clone 4 cultivar H1 gamma 3 hordein mRNA, complete cds; gi|34329256|gb|AY338368.1|[343292.56] AY338369; *Hordeum chilense* clone 5 cultivar H1 gamma 3 hordein mRNA, complete cds; gi|34329258|gb|AY338369.1|[34329258]AY338370; *Hordeum chilense* clone 6 cultivar H1 gamma 3 hordein mRNA, complete cds; gi|34329260|gb|AY338370.1|[34329260] AY338371; *Hordeum chilense* clone 7 cultivar H7 gamma 3 hordein mRNA, partial cds; gi|34329262|gb|AY338371.1|[34329262]AY338372; *Hordeum chilense* clone 8 cultivar H7 gamma 3 hordein mRNA, partial cds; gi|34329264|gb|AY338372.1|[34329264]AY338373; *Hordeum chilense* clone 9 cultivar H7 gamma 3 hordein mRNA, partial cds; gi|34329266|gb|AY338373.1|[34329266]AY 338374; *Hordeum chilense* clone 10 cultivar H7 gamma 3 hordein mRNA, partial cds; gi|34329268|gb|AY338374.1| [34329268]AY338375; *Hordeum chilense* clone 11 cultivar H7 gamma 3 hordein mRNA, partial cds; gi|3432920|gb|AY338375.1|[34329270]AY338376; *Hordeum chilense* clone 12 cultivar H7 gamma 3 hordein mRNA, partial cds; gi|34329272|gb|AY338376.1|[34329272]AY338377; *Hordeum chilense* clone 13 cultivar H7 gamma 3 hordein mRNA, partial cds; gi|34329274|gb|AY338377.1|[34329274]AY338378; *Hordeum chilense* clone 14 cultivar H7 gamma 3 hordein mRNA, partial cds; gi|34329276|gb|A Y338378.1| [34329276]AY338379; *Hordeum chilense* clone 1 cultivar 1-147 gamma 3 hordein gene, partial cds; gi|34329298|gb|AY338379.1|[34329298]AY338380; *Hordeum chilense* clone 2 cultivar H47 gamma 3 hordein gene, partial cds; gi|34329300|gb|AY338380.1|[34329300] AY338381; *Hordeum chilense* clone 3 cultivar H210 gamma 3 hordein gene, partial cds; gi|34329302|gb|AY338381.1| [34329302]AY338382; *Hordeum chilense* clone 4 cultivar H210 gamma 3 hordein gene, partial cds; gi|34329304|gb|AY338382.1|[34329304]AY338383; *Hordeum chilense* clone 5 cultivar H210 gamma 3 hordein gene, partial cds; gi|34329306|gb|AY338383.1|[34329306] AY338384; *Hordeum chilense* clone 6 cultivar H210 gamma 3 hordein gene, partial cds; gi|34329308|gb|AY338384.1| [34329308]AY338385; *Hordeum chilense* clone 7 cultivar H252 gamma 3 hordein gene, partial cds; gi|34329310|gb|AY338385.1|[34329310]AY695367; *Hordeum brevisubulatum* subsp. *turkestanicum* B hordein gene, complete cds; gi|51556913|gb|AY695367.1|[51556913] AY695368; *Hordeum brevisubulatum* subsp. *turkestanicum* B hordein gene, complete cds; gi|51556915|gb|AY695368.1|[51556915]AY695369; *Hordeum brevisubulatum* subsp. *turkestanicum* B hordein gene, complete cds; gi|51556917|gb|AY695369.1|[51556917] AY700807; *Hordeum chilense* cultivar H7 clone pC63-2 B3-hordein pseudogene mRNA, complete cds; gi|57118094|gb|AY700807.1|[57118094]AY998005; *Hordeum chilense* clone pC39-1 D-hordein-like mRNA, partial sequence; gi|66354246|gb|AY998005.1|[66354246] AY998008; *Hordeum chilense* clone pC36-2 (4) D-hordein-like mRNA, partial sequence; gi|66354251|gb|AY998008.1| [66354251]AY998009; *Hordeum chilense* D-hordein gene, 5' UTR and partial cds; gi|66354252|gb|AY998009.1| [66354252]AY998010; *Hordeum chilense* B-hordein gene, 5'UTR and parital cds; gi|66354254|gb|AY998010.1| [66354254]D82941; *Hordeum vulgare* Hor3 mRNA for D hordein, complete cds; gi|11674971|dbj|D82941.1|BLYHOR3[1167497] DQ148297; *Hordeum vulgare* subsp. *vulgare* cultivar XQ053 B hordein gene, complete cds; gi|73427780|gb|DQ148297.1|[73427780]DQ178602; *Hordeum vulgare* subsp. vulgare cultivar Aba-siqing B hordein gene, complete cds; gi|74422694|gb|DQ178602.1| [74422694]DQ189997; *Hordeum vulgare* subsp. vulgare clone Hn3 B hordein pseudogene, complete sequence; gi|75991848|gb|DQ189997.1|[75991848]DQ267476; *Hordeum vulgare* subsp. vulgare clone Hn4 B hordein pseudogene, complete sequence; gi|82548218|gb|DQ267476.1| [82548218]DQ267477; *Hordeum vulgare* subsp. vulgare clone Hn5 B hordein pseudogene, complete sequence; gi|82548220|gb|DQ267477.1|[82548220]DQ267478; *Hordeum vulgare* subsp. vulgare clone Hn6 B hordein gene, complete cds; gi|82548222|gb|DQ267478.1|[82548222] DQ267479; *Hordeum vulgare* subsp. *vulgare* clone Hn7 B hordein gene, complete cds; gi|82548224|gb|DQ267479.1| [82548224]DQ267480; *Hordeum vulgare* subsp, vulgare clone Hn8 B hordein pseudogene, complete sequence; gi|82548226|gb|DQ267480.1|[82548226]DQ267481; *Hordeum vulgare* subsp, vulgare clone Hn9 B hordein pseudogene, complete sequence; gi|82548228|gb|DQ267481.1| [82548228]DQ826387; *Hordeum vulgare* subsp. vulgare B hordein gene, complete cds; gi|110832714|gb|DQ826387.1| [110832714]J01237; barley b1 hordein mina. (partial); gi|167002|gb|J01237.1|BLYB1HOR[167002]K03147; Barley (*Hordeum vulgare* L.) C-hordein mRNA, clone pHvEc251; gi|167015|gb|K03147.1|BLYCHORD2[167015] M23836; *Hordeumvulgare* hordein (hor2-1) mRNA, 3' UTR; gi|530091|gb|M23836.1|BLYHOR21A[530091] M23869; *Hordeum vulgare* B1 hordein mRNA, 3' end; gi|530092|gb|M23869.1|BLYHORDB1A [530092] M35610; Barley C-hordein storage protein, 3' end; gi|167017|gb|M35610.1|BLYCHORDA[167017]M35611; Barley C-hordein storage protein, 3' end; gi|167019|gb|M35611.1|BLYCHORDB[167019]M36378; Barley gamma-1 hordein storage protein gene, complete cds; gi|167041|gb|M36378.1|BLYG1HORDA[167041] M36941; *Hordeum vulgare* C-hordein gene, complete cds; gi|167062|gb|M36941.1|BLYHORDCA[167062]S66938; C-hordein [Hordeurn vulgare=barley, M564, Genomic, 2806 nt]; gi|4425231bbm13247471bbs1139925|gb|S66938.1| [442523]X01024; Barley mRNA fragment for B1 hordein; gi|18906|emb|X01024.1|[18906]X01777; Barley mRNA fragment for B3-hordein; X01778; Barley mRNA fragment for B1-hordein; gi|18908|emb|X01778.1|[18908]X01779; Barley mRNA fragment for C-hordein (pcP387); gi|18948|emb|X01779.1|[18948]X03103; Barley gene for B1 hordein; gi|18909|emb|X03103.1|[18909]X13508; Barley gene for storage protein gamma-hordein; gi|18979|emb|X13508.1|[18979]X53690; *Hordeum vulgare* DNA for B-Hordein (per31); gi|18928|emb|X53690.11 [18928]X53691; *H. vulgare* DNA for B hordein (per47); gi|18930|emb|X53691.1|[18930]X60037; *H.vulgare* hor1-17 gene for C-hordein; gi|19000|emb|X60037.11[19000] X68072; *H.vulgare* mRNA for D hordein; gi|18969|emb|X68072.1|[18969]X72628; *H.vulgare* mRNA for gamma 3 hordein, 3' end;gi|2887081emb|X72628.1| [288708]X84368; *H.vulgare* Hor3 gene; gi|671536|emb|X84368.1|[1671536]X87232; *H.vulgare* B1 hordein gene; gi|809030|emb|X87232.1|[809030]

One embodiment of the present invention relates to transgenic barley plants comprising a prolamin which is non-toxic to a subject with coeliac's disease. As shown herein, examples of such a prolamin are an oat avenin and a maize zein.

Examples of oat avenin amino acid sequences (provided as Accession No; description iniNCBI; gi details) include, but are not necessarily limited to, 1411172A; avenin fast component N9; gi|226123|prf||411172A[226123]1502200A; prolamin; gi|226227|prf|1502200A[226227]AAA32713; avenin; gi|166551|gb|AAA32713.1|[166551]AAA32714; avenin; gi|166553|gb|AAA32714.1|[166553]AAA32715; avenin; gi|166555|gb|AAA32715.1|[166555]AAA32716; avenin; gi|166557|g|AAAA32716.1|[166557]AAB23365; gamma 3 avenin, coeliac immunoreactive protein 2, CIP-2, prolamin 2; gi|256082|gb|AAB23365.1||bbm|240522|bbs|113745 [256082]AAB32025; alcohol-soluble avenin-3=23.2 kda protein [*Avena sativa*=oat, Naryrnsky 943, Peptide, 201 aa]; gi|6937941gb|AAB32025.1||bbm|352847|bbs|156888 [693794]ABD14148; avenin [*Avena sativa*]; gi|86610884|gb|ABD14148.1|[86610884]CAE85306; unnamed protein product [*Avena sativa*]; gi|39923008|emb|CAE85306.1|[39923008]CAE85351; unnamed protein product [*Avena saliva*]; gi|39923098|emb|CAE85351.1|[39923098]P27919; Avenin precursor; gi|114720|sp|P27919|AVEN_AVESA[114720] P80356; Avenin-3 precursor (Prolamin); gi|728937|sp|P80356|AVE3_AVESA[728937]Q09095; Avenin-A (Gamma-4 avenin) (Prolamin) (Celiac immunoreactive protein 1) (CIP-1); gi|75107163|sp|Q09095|AVEA_AVESA[75107163] Q09097; Avenin-F (Gamma-3 avenin) (Prolamin) (Celiac immunoreactive protein 2) (CIP-2); gi|75107165|sp|Q09097|AVEF_AVESA[75107165] Q09114; Avenin-E (Alpha-2 avenin) (Avenin N9) (Prolamin) (Celiac immunoreactive protein 3) (CIP-3); gi|75107166|sp|Q09114|AVEE_AVESA[75107166] S06211; avenin alpha-2-small naked oat (fragment); gi|82325|pir||S06211[82325]S07621; avenin gamma-3-small naked oat (fragment); gi|2119756|pir||S07621 [2119756]S07622; avenin gamma-4-small naked oat (fragment); gi|82327|pir||S07622[82327]

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the barley grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain of a barley plant of the invention,
(ii) steeping said grain,
(iii) germinating the steeped grains under predetermined conditions and
(iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of speciality malts, including, but limited to, methods of roasting the malt. One non-limiting example is described in Example 6.

Malt may be prepared using only grain produced from barley plants of the invention or in mixtures comprising other grains.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

In another embodiment, wort compositions can be prepared from the malt. Said wort may be first and/or second and/or further wort. In general a wort composition will have a high content of amino nitrogen and fermentable carbohydrates, mainly maltose. Typically, wort is prepared by incubating malt with water, i.e. by mashing. During mashing, the malt/water composition may be supplemented with additional carbohydrate-rich compositions, for example barley, maize or rice adjuncts. Unmalted cereal adjuncts usually contain no active enzymes, and therefore rely on malt or exogenous enzymes to provide enzymes necessary for sugar conversion.

In general, the first step in the wort production process is the milling of malt in order that water may gain access to grain particles in the mashing phase, which is fundamentally an extension of the malting process with enzymatic depolymerization of substrates. During mashing, milled malt is incubated with a liquid fraction such as water. The temperature is either kept constant (isothermal mashing) or gradually increased. In either case, soluble substances produced in malting and mashing are extracted into said liquid fraction before it is separated by filtration into wort and residual solid particles denoted spent grains. This wort may also be denoted first wort. After filtration, a second wort is obtained. Further worts may be prepared by repeating the procedure. Non-limiting examples of suitable procedures for preparation of wort is described in Hoseney (supra).

The wort composition may also be prepared by incubating barley plants of the invention or parts thereof with one or more suitable enzyme, such as enzyme compositions or enzyme mixture compositions, for example Ultraflo or Cereflo (Novozymes). The wort composition may also be prepared using a mixture of malt and unmalted barley plants or parts thereof, optionally adding one or more suitable enzymes during said preparation. In addition, prolyl-endopeptidase enzymes which specifically destroy the toxic amino linkages involved in coeliac disease could be added during the fermentation of the wort to reduce the toxicity of the residual hordeins (De Angelis et al., 2007; Marti et al., 2005; Stepniak et al., 2006).

Grain Processing

Barley grain of the invention can be processed to produce a food or non-food product using any technique known in the art.

In one embodiment, the product is whole grain flour (an ultrafine-milled whole grain flour, such as an ultrafine-milled whole grain flour; a whole grain flour, or a flour made from about 100% of the grain). The whole grain flour includes a refined flour constituent (refined flour or refined flour) and a coarse fraction (an ultrafine-milled coarse fraction).

Refined flour may be flour which is prepared, for example, by grinding and bolting cleaned barley. The Food and Drug Administration (FDA) requires flour to meet certain particle size standards in order to be included in the category of refined barley flour. The particle size of refined flour is described as flour in which not less than 98% passes through a cloth having openings not larger than those of woven wire cloth designated "212 micrometers (U.S. Wire 70)".

The coarse fraction includes at least one of: bran and germ. For instance, the germ is an embryonic plant found within the barley kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. Preferably, the coarse fraction is homogenously blended with the refined flour constituent. Homogenously blending the coarse fraction and refined flour constituent may help reduce stratification of the particles by size during shipping. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. It is contemplated by the present invention that inactivated may also mean inhibited, denatured, or the like. Stabilization is a process that uses steam, heat, radiation, or other treatments to inactivate the enzymes found in the bran and germ layer. Naturally occurring enzymes in the bran and germ will catalyze changes to compounds in the flour, adversely affecting the cooking characteristics of the flour and the shelf life. Inactivated enzymes do not catalyze changes to compounds found in the flour, therefore, flour that has been stabilized retains its cooking characteristics and has a longer shelf life. For example, the present invention may implement a two-stream milling technique to grind the coarse fraction. Once the coarse fraction is separated and stabilized, the coarse fraction is then ground through a grinder, preferably a gap mill, to form a coarse fraction having a particle size distribution less than or equal to about 500 micrometers. In an exemplary embodiment, the gap mill tip speed normally operates between 115 m/s to 144 m/s, the high tip speed generates heat. The heat generated during the process and the airflow lead to a decrease in the microbial load of the coarse fraction. In further embodiments, prior to grinding in a gap mill, the coarse fraction may have an average aerobic plate count of 95,000 colony forming units/gram (cfu/g) and an average coliform count of 1,200 cfu/g. After passing through the gap mill the coarse fraction may have an average aerobic plate count of 10,000 cfu/g and an average coliform count of 900 cfu/g. Thus, the microbial load may be noticeably decreased in the coarse fraction of the present invention. After sifting, any ground coarse fraction having a particle size greater than 500 micrometers may be returned to the process for further milling.

In additional embodiments, the whole grain flour or the coarse fraction may be a component of a food product. For example, the food product may be a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, to mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product a snack chip, a snack food, a snack mix, a waffle, a pizza crust, animal food or pet food.

In alternative embodiments, the whole grain flour or coarse fraction may be a component of a nutritional supplement. For instance, the nutritional supplement may be a product that is added to the diet containing one or more ingredients, typically including: vitamins, minerals, herbs, amino acids, enzymes, antioxidants, herbs, spices, probiotics, extracts, probiotics and fiber. The whole grain flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. Further, 14 grams is all that is needed to deliver 20% of an individuals daily recommend consumption of fiber. Thus, the coarse fraction is an excellent supplemental source for consumption of an individual's fiber requirement. Therefore, in a present embodiment, the whole grain flour or coarse fraction may be a component of a nutritional supplement. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients.

In additional embodiments, the whole grain flour or coarse fraction may be a fiber supplement or a component thereof. Many current fiber supplements such as psyllium husks, cellulose derivatives, and hydrolyzed guar gum have limited nutritional value beyond their fiber content. Additionally, many fiber supplements have a undesirable texture and poor taste. Fiber supplements made from the whole grain flour or coarse fraction may help deliver fiber as well as protein, and antioxidants. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour, multi-barley flour, or a multi-grain coarse fraction. For example, bran and germ from one type of barley may be ground and blended with ground endosperm or whole grain barley flour of another type of barley. Alternatively bran and germ of one type of grain may be ground and blended with ground endosperm or whole grain flour of another type of grain. In an additional embodiment, bran and germ from a first type of barley or grain may be blended with bran and germ from a second type of barley or grain to produce a multi-grain coarse fraction. It is contemplated that the present invention encompasses mixing any combination of one or more of bran, gel ne endosperm, and whole grain flour of one or more grains. This multi-grain, multi-barley approach may be used to make custom flour and capitalize on the qualities and nutritional contents of multiple types of grains or barleys to make one flour.

The whole grain flour of the present invention may be produced via a variety of milling processes. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. In one embodiment, the grinder may be a gap mill. After grinding, the grain is discharged and conveyed to a sifter. Any sifter known in the art for sifting a ground particle may be used. Material passing through the screen of the sifter is the whole grain flour of the present invention and requires no further processing. Material that remains on the screen is referred to as a second fraction. The second fraction requires additional particle reduction. Thus, this second fraction may be conveyed to a second passage grinder. After grinding, the second fraction may be conveyed to a second sifter. Material passing through the screen of the second sifter is the whole grain flour of the present invention. The material that remains on the screen is referred to as the fourth fraction and requires further processing to reduce the particle size. The fourth fraction on the screen of the second sifter is conveyed back into either the first passage grinder or the second passage grinder for further processing via a feedback loop. In an alternative embodiment of the invention, the process may include a plurality of first pass grinders to provide a higher system capacity.

It is contemplated that the whole grain flour, coarse fraction and/or grain products of the present invention may be produced by any milling process known in the art. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Polynucleotides Which Down-Regulate the Production of a Hordein

In one embodiment, grain of the invention, and/or used in the methods of the invention, is from a transgenic barley plant which comprises a transgene which encodes a polynucleotide which down-regulates the production of at least one hordein in the grain. Examples of such polynucleotides include, but are not limited to, antisense polynucleotide, a sense polynucleotide, a catalytic polynucleotide, an artificial microRNA or a duplex RNA molecule. When present in the grain, each of these polynucleotides result in a reduction in hordein mRNA available for translation.

Antisense Polynucleotides

The term "antisense polynucletoide" shall be taken to mean a DNA or RNA, or combination thereof, molecule that is complementary to at least a portion of a specific mRNA molecule encoding a hordein and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Senior (1998) states that antisense methods are now a very well established technique for manipulating gene expression.

An antisense polynucleotide in a barley plant of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as a barley hordein under normal conditions in a barley cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al., 1992) and the hairpin ribozyme (Snippy et al., 1999).

The ribozymes in barley plants of the invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example an mRNA encoding a barley hordein) under "physiological conditions", namely those conditions within a barley cell.

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Constructs

Nucleic acid constructs useful for producing transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the seed.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of Arabidopsis, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., WO 84/02913. All of these promoters have been used to create various types of plant-expressible recombinant DNA vectors.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to the use of constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the barley cells, or allow the utilization of substrates such as mannose. The selectable marker preferably confers hygromycin resistance to the barley cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes the use of a recombinant vector, which includes at least transgene outlined herein, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Transgenic Plants

Transgenic barley plants, as defined in the context of the present invention include plants (as well as parts and cells of said plants) and their progeny which have been genetically modified using recombinant techniques to cause production of at least one polynucleotide and/or polypeptide in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932479, and WO 99/05265.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

Modem *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are riot limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and WO 99/14314. Preferably, transgenic barley plants are produced by *Agrobacterium turnefaciens* mediated transformation procedures. Vectors carrying the desired nucleic acid construct may be introduced into regenerable barley cells of tissue cultured plants or explants, or suitable plant systems such as protoplasts.

The regenerable barley cells are preferably from the scutellum of immature embryos, mature embryos, callus derived from these, or the meristematic tissue. To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf (2005) and Henikoff et al., (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

EXAMPLES

Example 1

Materials and Methods

Isolation and Purification of Prolamins

To isolate prolamins from cereals, whole-meal flour (10 g) was stirred for 30 min at 25° C. in 200 ml of buffer containing 20 mM triethanolamine-HCl (TEA), 1% (w/v) sodium ascorbate, 1% (w/v) polyethylene glycol (MW 6000; PEG6000) and 200 µl of plant protease inhibitor cocktail (Sigma #P9599), all adjusted to pH 8. The suspension was centrifuged at 7,000 g for 15 min and the pellet washed twice more to remove proteins soluble in aqueous buffer. Prolamins in the washed pellet were dissolved in 40 ml of 50% (v/v) propan-2-ol containing 1% (w/v) dithiothreitol (DTT), 1% (w/v) PEG6000, 1% (w/v) sodium ascorbate by stirring for 30min at 25° C. The suspension was centrifuged and prolamins precipitated from the supernatant with 2 volumes of propan-2-ol and stored at −20° C. When required, an aliquot equivalent to 10 g of flour was sedimented by centrifugation at 160 g at 4° C. for 10 min, the pellet redissolved in 10 ml of buffer (buffer A) which contained 25 mM TEA, 8M freshly deionised urea and 1% DTT, all adjusted to pH 6, or other buffers as described.

A total prolamin fraction was purified from each grain sample by reverse phase-fast protein liquid chromatography (RP-FPLC) as follows: Prolamins (200 µl) were injected into a Resource RPC column (Pharmacia) connected in series with a similar 3 ml column. The column was washed with 2 ml of 95% solvent A/5% solvent B and prolamins eluted with a 30 ml linear gradient from 95% solvent A/5% solvent B to 100% solvent B at 2 ml/min. Solvent A was 0.1% (v/v) trifluoroacetic acid (TFA) in water, solvent B was 0.1% (v/v) TFA in 60% (v/v) aqueous acetonitrile. Eluant corresponding to protein peaks was pooled. Solvent controls were similarly pooled from runs without protein injection.

Barley hordeins were further fractionated by RP-FPLC as follows: Procedures were as above except that the elution gradient was varied so that the concentration of solvent B was 50% at 4 ml, 52% at 17 ml, 56% at 34 ml, 58% at 37 ml, 60% at 41 ml, 62% at 44 ml, 64% at 47 ml, 66% at 50 ml, 100% at 53 ml, 100% at 57 ml. One ml fractions were collected and fractions 11-14 (#1), 19-23 (#2), 31-34 (#3), 43-51 (#4), 53-58 (#5) and 63-64 (46) corresponding to A280 peaks were pooled.

Analytical Methods

Prolamin fractions were dissolved in 6M urea, 2% (w/v) SDS, 1% (w/v) DTT, 0.01% (w/v) bromophenol blue, 0.0625 M Tris-HCL (pH 6.8) at 25° C. and examined by SDS-PAGE as follows. A 5 µl aliquot of the prolamin-SDS solution was loaded onto SDS-PAGE gels, using pre-cast 245×110×0.5 mm, 8-18% polyacrylamide gradient gels (ExcelGel Pharmacia), and run at 600V for 90 min at 15° C. The gels were washed in 40% MeOH in 10% acetic acid for 30 min, then water for 10 min. The prolamins were stained by soaking the gel in 0.06% (w/v) colloidal Coomassie G250 in 8.5% phosphoric acid for 30 min and the gels destained overnight in water. Each gel was calibrated with a 10 kDa standard protein ladder (BenchMark, Invitrogen).

Hordein fractions were also dissolved in 50% (v/v) aqueous isopropyl alcohol, 1% (w/v) DTT, treated with an excess of vinyl-pyridine to reduce di-sulphide bonds and examined by reverse phase-HPLC (RP-HPLC, Larroque et al., 2000) calibrated with prolamins isolated from barley lines Riso56 or Riso1508 where the entire B or C hordein families, respectively, are not accumulated due to mutation (Doll, 1983).

Protein levels in extracts or fractions were determined by the method of Bradford (1976). Typically, the protein content was measured in a 96-well format by adding 10 µl of each DTT/propan-2-ol supernatant to 200 µl of a 1 in 5 dilution of Coomassie protein assay concentrate (BioRAD) in water, calibrated against gamma globulin, and measuring the absorbance at 595 nm.

Ex vivo T-cell Toxicity Assays

Prolamins (50 mg/ml in 2M urea) were diluted with PBS containing 1 mM $CaCl_2$, to give either 62.5, 250, 625, 2500, or 6250 µg prolamin/ml and deamidated by adding 25 µl of each solution to 100 µl of guinea pig liver tTG (transglutaminase (Sigma, T5398), 25 µg/ml tTG in PBS containing 1 mM $CaCl_2$) and incubated for 6 hr at 37° C. Non-deamidated solutions were similarly prepared by incubation in the absence of tTG. Solvent controls were added as for the highest prolamin concentrations. Other controls contained either a known toxic ω-gliadin peptide designated 626fEE at 50 µg/ml, the 626fEE peptide alone or with tetanus toxoid (50 light forming units/ml). The ω-gliadin peptide 626fEE also known as DQ2-ω-1 had the amino acid sequence QPEQPFPQPEQPFPWQP (SEQ ID NO:1) and was synthesised by Mimotopes, Melbourne, Australia. Its identity and purity (91%) were confirmed by mass spectrometry and HPLC. Tetanus toxoid was obtained from the Commonwealth Serum Laboratories, Melbourne. All solutions were then frozen at −20° C.

Twenty one, biopsy-proven HLA-DQ2$^+$ coeliac disease subjects, who had adhered to a strict gluten-free diet for at least three months, were provided 150 g of boiled barley daily for 3 days, consumed as part of their diet which otherwise remained gluten-free. Heparinised venous blood was collected either immediately prior to or six days after commencement of dietary challenge and peripheral blood mononuclear cells (PBMC) isolated by Ficoll-Hypaque density centrifugation (Anderson et al., 2000) from each blood sample. The PBMC cells were resuspended in complete HT-RPMI medium (Invitrogen) containing 10% heat-inactivated, pooled, human AB serum. Deamidated or non-deamidated prolamins and control solutions were thawed and 25 µl added to wells containing 100 µl of PBMC (3-8×10$^5$ PBMC per well). These were cultured at 37° C.

overnight in 96-well plates (MAIP-S-45; Millipore, Bedford, Mass.). Control cultures were made by adding 25 μl of PBS containing 1 mM $CaCl_2$ (buffer alone controls). Final prolamin concentrations were 2.5, 10, 25, 100 or 250 μg/ml and the final urea concentration was 50 mM. The level of IFN-γ produced in each culture, indicative of the toxicity of each prolamin, was assayed visually by spot formation using secondary antibodies according to the suppliers instructions (Mabtech, Stockholm, Sweden) and spot forming units (SFU) counted using an automated ELISPOT reader (AID Autoimmun Diagnostika GmbH; Germany). Results were presented as the mean spot forming units (SFU)±S.E. Typically, intra-assay percent coefficient of variation of $SFU/10^6$ PBMC was 14% based on six duplicate assays of a positive control incubated with $0.5×10^6$ cells in six CD subjects (all with>20 SFU/well).

Statistical Analysis

Analysis of variance (ANOVA) or t-tests using GenStat was used to determine the significance of the differences observed for the mean SFU produced by T-cells isolated from coeliac subjects either before (n=10) or after (n21) a dietary challenge and incubated with hordeins, prolamins or controls.

The response curves for the 21 post-challenge individuals were very different and a large proportion of the variability was due to these differences. In order to take account of the different patient response, a random coefficients model was fitted. This is a mixed model analysis that is performed using Residual Maximum Likelihood (REML) and which allows for random terms involving the subject (patient) and the challenge (the protein concentration) within patient. In order to stabilize the substantial heterogeneity of variance the data were log transformed prior to this analysis. In order to deal with the problem of zero counts one was added to all data prior to taking logs. The fixed terms in the model were the presence or absence of tTG and the hordein fraction that was involved, together with their interaction.

A hyperbolic model was also fitted to the untransformed mean SFU for T-cells from the 21 post challenge patients, exposed to the six tTG hordein fractions or the four tTG treated cereal prolamin preparations.

Barley Transformation

Transformed barley plants may be produced by the method of Tingay et al., (1997). The gene constructs in binary vectors may be introduced into a highly virulent *Agrobacterium* strain (AGL1) by tri-parental conjugation, which is then used to introduce the T-DNA containing the transgene and the selectable marker gene (encoding hygromycin resistance, expressed from the CaMV35S promoter) into regenerable cells of the scutellum of immature barley embryos, as follows.

Developing barley seeds from the variety Golden Promise, 12-15 days after anthesis, are removed from the growing spike of greenhouse grown plants and sterilised for ten minutes in 20% (v/v) bleach followed by rinsing once with 95% ethanol and seven times with sterile water. Embryos (approx 1.5 to 2.5 mm in size) are then removed from the seeds under aseptic conditions and the axis cut from each embryo. The embryos are placed cut side down on a petri dish containing callus induction medium. The Agrobacterium transconjugants are grown in MG/L broth (containing 5 g mannitol, 1 g L-glutamic acid, 0.2 g $KH_2PO_4$, 0.1 g NaCl, 0.1 g $MgSO_4.7H_2O$, 5 g tryptone, 2.5 g yeast extract and 1 μg biotin per litre, pH 7.0) containing spectinomycin (50 mg/L) and rifampicin (20 mg/L) with aeration at 28° C. to a concentration of approximately $2-3×10^8$ cells/ml. Then, approximately 300 μl of the cell suspension is added to the embryos in a petri dish. After 2 min, excess liquid is tipped from the plate and the embryos are flipped so that the cut side (axil side of the scutellum) is upwards. The embryos are then transferred to a fresh plate of callus inducing medium and placed in the dark for 2-3 days at 24° C. The embryos are transferred to callus inducing medium with selection (50 μg/ml hygromycin and 15 μg/ml timentin).

Embryos remain on this media for 2 weeks in the dark at 24° C. Healthy callus is then divided and placed on fresh selection media and incubated for a further two weeks at 24° C. in the dark. Following this, the embryos are incubated at 24° C. in the light for 2 weeks on regeneration medium containing cytokinin and transferred to rooting media containing cytokinin and auxin for three 2 week periods. Juvenile plants are then transferred to soil mixture and kept on a misting bench for two weeks and finally transferred to a glasshouse.

Mutagenesis Methods Including Gamma Irradiation

Mutation of genes in barley leading to reduced expression of D, C, B or γ-hordeins can be achieved through either gamma ray irradiation or chemical mutagenesis, for example with ethyl methane sulfonate (EMS). For gamma ray induced mutation, seeds may be irradiated at a dose of 20-50 kR from a $^{60}Co$ source (Zikiryaeva and Kasimov, 1972). EMS mutagenesis may be performed by treating the seeds with EMS (0.03%, v/v) as per Mullins et al, (1999). In a B+C double null background, mutant grains may be identified on the basis of decreased protein or hordein content or altered grain morphology and confirmed by the methods described above. Mutants in one hordein gene can be crossed with a second mutant to combine the mutations and produce a non-transgenic variety of barley substantially lacking hordeins in the endosperm.

Example 2

Toxicity of Barley Hordeins to Coeliacs

Prolamin Composition of Barley and Other Cereals

Prolamins were isolated as aqueous-alcohol soluble proteins from the coeliac toxic cereals, barley and wheat, the less toxic oats and non-toxic maize and purified by one round of RP-FPLC as described in Example 1. The protein elution profiles of the prolamins as determined by $A_{280\,nm}$ in the RP-FPLC (FIG. 1) showed a series of partially resolved peaks due to individual proteins eluted by the steeply increasing solvent gradient. Fractions containing protein from 10 purifications for each cereal were combined and lyophylised. The typical yield of prolamin from various cereals (2 g) was: maize, 10 mg; oats, 23 mg; barley, 73 mg; and wheat, 114 mg. The total prolamins from each cereal were lyophilized and stored for testing in the ex vivo T-cell assay (below). Solvent controls were also prepared from the RP-FPLC procedure.

The barley prolamins (hordeins) were also fractionated by RP-FPLC as described in Example 1. The elution profile obtained during fractionation in an initial experiment is shown in FIG. 2. Six peaks were obtained and the protein from each recovered. Corresponding pooled fractions from twenty sequential injections were combined and lyophylised. Typical yields from 4 g of whole-meal flour were: fraction 1, 19 mg; fraction 2, 26 mg; fraction 3, 14 mg; fraction 4, 104 mg; fraction 5, 24 mg and fraction 6, 11 mg.

The identity of the hordeins in each fraction was established by SOS-PAGE as described in Example 1 and confirmed by analytical RP-HPLC. The results are shown in FIGS. 3 and 6. HPLC showed that fraction #1 contained about 39% D hordein, which ran at 90 kDa on SOS-PAGE, and about 61% C hordeins which ran at 47 and 45 kDa on SDS-PAGE (FIG. 3, #1). Fraction 42 contained C hordeins as shown by both SOS-PAGE and HPLC. Fraction #3 contained a broad protein band which ran at about 45 kDa on SOS-PAGE but which resolved into 6 peaks on HPLC, corresponding to the elution of both C and B hordeins. The composition was estimated by HPLC as containing about 43% and 57% C and B hordeins, respectively. Fractions #4, 5, 6, contained B hordeins; these fractions may also contain a small amount of gamma-hordein. Two dimensional electrophoresis and tryptic mass fingerprinting of these hordein fractions did not produce sufficient unique peptide fragments to unequivocally identify individual hordeins. This may be due to slight sequence variations between the isolated hordeins and the sequences available in the data bases. The fractionation in this experiment therefore resulted in enrichment for particular hordeins from barley but not complete purification. Further purification can be achieved by further rounds of RP-FPLC or RP-FLPC combined with ion exchange methods.

Samples of each hordein fraction were treated or not treated with tTG, which converts glutamine residues in the proteins to glutamate, and then lyophilized for use in the T-cell assays.

Toxicity Assays

T-cell assays using PBMC isolated from confirmed coeliac-disease subjects were carried out as described in Example 1 to establish the toxicity of the total prolamin preparations and the hordein fractions. PBMC were isolated before and after dietary challenge with barley, and prolamin samples were either treated or not treated with tTG. T-cells isolated from a subset of 10 coeliacs prior to a dietary challenge were unresponsive to prolarnins. Statistical analysis using ANOVA showed there was no significant difference (P=0.77) between the mean number of IFN-γ positive spots for the highest concentrations of all tTG treated prolamin, peptide or hordein fractions (group mean SFU±S.E. 1.52±0.18) and control cultures (mean SFU±S.E. 1.40±0.45). In contrast, the analysis showed that pre-challenge T-cells reacted strongly (P<0.001) to the positive control tetanus toxoid (mean SFU±S.E. 22.3±4.72) compared to prolamins. This shows that the isolated T-cells were functional and capable of reacting to a known toxin and confirms that there were few prolamin reactive T-cells in the populations isolated before the dietary challenge.

In contrast to the lack of response to prolamins before dietary challenge, T-cells isolated after the dietary challenge were highly reactive. T-cells isolated from 21 coeliacs, 6 days post challenge, responded strongly to tTG treated prolarnins when compared to T-cells from a subset (n=13) of this group exposed to non-deamidated prolamins. FIG. 4 shows that of the cereals, total barley prolarnins induced the highest number of SFU followed in decreasing order by prolamins from wheat, oats and then maize (FIG. 4 panels A, B, C, D, respectively). Although maize prolamin did provoke a low dose-dependant T-cell response in these assays, it normally does not provoke a response in dietary challenges and is considered a coeliac-safe cereal. Intestinal digestion may destroy epitopes present in whole maize prolamins which remained intact in our assay and stimulated T-cells in vitro.

Of the hordein fractions, fractions #1, #2 and #3 produced higher numbers of SFU than hordein fractions #4, #5 and #6 (FIG. 5).

As the concentration of prolamin in the assays was increased, the number of IFN-γ spots increased in a hyperbolic mariner in a similar fashion to the Michaelis-Menten enzyme kinetics often seen between an enzyme and its substrate (FIGS. 4 and 5), although it was not clear why this occurred for these cellular assays.

Each 96 well plate contained a number of internal positive and negative controls, There was a small but significant difference (P<0.001) between mean SFU when control cultures and the solvent controls were compared (control cultures SFU 2.75±0.67 and 1.49±0.24; solvent controls SFU 2.64±0.23 and 2.75±0.23 in the absence and presence of tTG respectively). Although statistically significant, these values were very small compared to the post challenge SFU in the positive controls or the prolamin containing assays. This confirmed that solvent impurities did not generate false positives. The positive control peptide 626fEE, gave a consistently high response (mean SFU±S.E. 29.55±4.38 and 3160±2.97 in the absence and presence of tTG respectively). The lack of response of 626fEE to tTG was expected since this peptide was synthesised with a glutamate in the $10^{th}$ residue and does not require tTG treatment for toxicity. Addition of the solvent control did not significantly inhibit the response of the positive 626fEE peptide (P=0.13), confirming that solvent impurities did not generate false negatives. The plate to plate consistency of the tetanus toxoid controls (P=0.193) confirmed that differences in T-cell response to prolarnins was not due to plate to plate variation, but reflected the differing sensitivity of T-cell populations from different subjects.

The variation between different subjects to the same prolamin concentration varied by as much as 200-fold. Therefore, a random coefficients REML model was fitted to the normalized SFU data and it was found that a model allowing for curvature in patient responses due to the different concentrations of the protein gave a significantly better fit (P<0.001) to the data than a model that fitted a single patient response regardless of concentration, with the deviance changing from 1982.28 (1616 df) to 1640.91 (1613 df). The main effects due to tTG (P<0.001) and the prolamin fraction (P<0.001) were highly significant and there was no interaction between them. This confirmed that prolamin responsive T-cells were induced in coeliac subjects six days after the dietary challenge with barley. The fitted means, on a log scale, for the normalized SFU data were 1.613 (no tTG) and 2.026 (plus tTG) with a standard error of difference (SED) of 0.0527, confirming that pretreatment with tTG had a significant effect on the responses. The fitted means for hordein fractions #1-#6 were 1.903, 1.909, 1.956, 1.693, 1.724 and 1.733 respectively with an SED of 0.0826. These results show that the hordein fractions fall into two significantly different toxicity groups with hordein fractions #1, #2 and #3 fowling a more toxic group than hordein fractions #4, #5 and #6.

It was interesting to note that the most toxic hordein fractions eluted first from reverse phase FPLC and HPLC, and were therefore more polar than the later eluting, less toxic fractions.

Conclusions

T-cells isolated from 21 coeliacs, 6 days post challenge, responded strongly to tTG treated prolamins as compared to non-deamidated prolamins as expected for coeliac disease (Hadjivassiliou et al., 2004; Kim et al., 2004). This could be explained by an interaction between the deamidated prolamins and a binding site in a key protein, such as the HLA-DQ2 molecule, which presented stimulatory proteins to receptors on $CD4^+$ T-cells involved in the inflammatory response.

Although there were measurable differences in the toxicity of hordein fractions, all hordeins were significantly more toxic than maize and oat prolarnins, which are regarded as safe for most coeliacs. The statistical analyses showed that the barley prolamins and hordein fraction #1, #2 and #3 (containing D and C hordeins) formed the most toxic group. Hordein fractions #4, #5 and #6, containing mainly B hordeins, and wheat prolamins formed a second, less toxic group. Oats and maize prolamins formed the least toxic group. This indicated that T-cells induced in coeliacs by a barley challenge were less sensitive to wheat and oats. This may be because the dominant epitopes in barley prolamin differ considerably from those in wheat and oats prolamins. Although the fitted data indicated that oat prolamins were significantly less toxic than those from barley, there was a fifty fold variation between different subjects to the same concentration of oat prolamin, with T-cells from five of the 21 subjects having over 20 SFU at the highest prolamin concentration. This was consistent with other reports of individuals with serious coeliac responses to oats (Arentz-Hansen et al., 2004; Lundin et al., 2003).

It was considered likely based on this data that, in a dietary challenge, all of the hordein fractions would provoke a significant intestinal reaction in coeliacs. This suggested that all hordein fractions would need to be deleted or modified to produce barley which was completely non-toxic to coeliacs. It also suggested that hordeins B and C, the major components, should be removed or modified first of all.

Example 3

Production of Barley Grain Reduced for Both B and C Hordeins

A number of barley mutants affected in hordein synthesis or accumulation have been identified previously. These barley mutants were not isolated for the purpose of reducing hordeins in the grain, but were isolated and selected for increased lysine levels in the grain and subsequently formed to be reduced for hordeins.

The mutant Riso 7, first described by Doll et al. (1976), was identified after fast neutron treatment of the parent Bomi. It contained a recessive mutation in a gene that resulted in a 29% decrease in prolamins and a 10% increase in the lysine content of protein relative to Bomi. The reduction in the lysine-poor prolamins was compensated for by an increase in other, relatively lysine-rich storage proteins, resulting in elevated lysine content. The grain yield and starch content were reduced by 6% and 7%, respectively, compared to the parent (Talberg, 1982; Doll, 1983). Riso 56, first described by Doll et al. (1973), was created by gamma-ray mutation of the parent Carlsberg H. Kernel size, grain yield, and prolamin content were decreased by 30%, 47%, and 25%, respectively, relative to the parent while the lysine content of protein in the mutant grain was increased by 13% compared to the parent. The decreased hordein content was associated with increased non-protein nitrogen and water and salt-soluble proteins (Shewry P R et al. 1980). The high lysine content of proteins in Riso 56 was due to a recessive mutation on chromosome 5 (Ullrich and Eslick, 1978) at a genetic locus designated Hor2ca (Doll, 1980). The mutation included deletion of 80-90 kb of DNA from the Hor2 locus which encoded the B hordeins in barley. Expression of B hordein proteins was reduced by 75% in the mutant while expression of the C hordeins was increased by 2-fold (Kreis et al., 1983). The deletion was not related to the translocation between chromosome 2 and 5 that was also present in Riso 56 (Olsen, 1977).

Riso 527, first described by Doll et al. (1973), was also created by gamma-ray mutation but from the parent Bomi. Kernel size, grain yield and grain prolamin content were decreased by 13%, 25%, and 20%, respectively, relative to the parent while the lysine content of protein in the mutant was increased by 12%. The mutation was recessive, in a gene on chromosome 6 designated lys6i (Jensen, 1979). This mutant had decreased levels of D hordeins and increased levels of B1 hordeins (Klemsdal et al., 1987).

Riso 1508 was identified after EMS mutation of the parent Bomi (Doll et al., 1973; Ingerversen et al., 1973; Doll, 1973). Kernel size, grain yield and grain prolamin content were decreased by 8%, 12%, and 70%, respectively, relative to the parent grain while the lysine content of protein in the mutant was increased by 42%. The high lysine content was due to a recessive mutation in a gene located near the centromere region of barley chromosome 7 (Karlsson, 1977). This gene was first designated as shrunken endosperm xenia sex3c (Ullrich and Eslick, 1977) but is now generally known as lys3a (Tallberg, 1977). The relative levels of protein types in the mutant grain was changed, with more water soluble protein (albumin/globulins) increased from 27% to 46% of total seed protein nitrogen and less prolamin, decreased by 70% relative to the parent, from 29% to 9% of total seed protein nitrogen (Ingerversen et al., 1973; Doll, 1973). There was a four-fold increase in both free amino-acids and non-protein N in Riso 1508, compared to the parent when plants were grown under high levels of nitrogen fertilizer (Koeie and Kreis, 1978). Shewry et al. (1978) confirmed that the level of salt-soluble non-protein nitrogen was doubled. The proportion of seed nitrogen as hordein was decreased by 70% and the salt soluble proteins increased by 70% in Rise 1508 compared to Bomi. Detailed molecular analysis showed that the levels of B and C hordeins were reduced by 80% and 93%, respectively, while the D hordeins were increased four-fold. These effects on protein accumulation were due to changes in mRNA abundance or stability (Kreis et al., 1984). This might have been mediated by increased methylation of the promoters of the genes encoding the B and C hordeins in the Riso 1508 mutant (Sorensen et al., 1996). The smaller seed size of Riso 1508 was mainly due to reduced synthesis of starch (Koeie and Breis, 1978; Kreis and Doll, 1980; Doll, 1983). Sugars were increased by two-fold while starch synthesis was decreased by about 20-30% in Riso 1508 compared to the parent. Kreis (1979) reported that β-amylase levels were reduced in Riso 1508 while Hejgaard and Boisen (1980) reported similar levels of β-amylase.

Hiproly was a spontaneous mutant identified from Ethiopian germplasm CI 3947 (Munck et al., 1970) which had increased levels of both total protein and protein lysine, increased by 20-30% relative to wild-type barleys (Doll, 1983). When crossed to wild-type barley, the high protein content was lost while the increased protein lysine content was retained, demonstrating that these traits were inherited independently. The increased lysine content was due to a single recessive mutation in the lys gene on chromosome 7. The mutation increased the level of water and salt soluble proteins and thereby the lysine content. Unlike the Rise high lysine mutants, the hordein levels and seed weight in Hiproly were not decreased in backcrossed progeny. Non-protein nitrogen was also not increased. The content of β-amylase was increased 4-fold (Hejgaard and Boisen, 1980).

Characterisation of the Parental Lines Riso 56 and Riso 1508

The characteristics of prolamins accumulated by the parental lines Riso 56 and Riso 1508 were confirmed by SDS-PAGE and reverse phase HPLC. Salt-soluble proteins extracted from grain were separated by gel electrophoresis and transferred to membranes (Western blotting). The protein patterns on membranes stained for total protein (FIG. 7, left hand side) or treated with a prolamin specific monoclonal antibody (mouse monoclonal antibody MAb12224, raised against a total glutenin extract, and which detects all hordeins and prolamins (Skerritt, 1988) (right hand side) showed that the levels of B hordeins were very low in Riso 56 while the C hordeins were increased relative to the levels in Riso 527. Antibody detection confirmed that the level of B hordeins in the Riso 56 extract were extremely low (dotted box). The three proteins seen in Riso 56 which co-migrated with the B hordeins were most likely γ-hordeins. In Riso 1508, accumulation of the B hordeins was reduced while the C-hordeins were barely detectable (dotted box). This was consistent with the published literature. Levels of D hordein, which was a relatively minor prolamin component, did not appear to be increased at the protein loadings used in this gel.

FIG. 8 shows the relative levels of the different hordeins in purified extracts after reverse-phase FPLC analysis. Hordein extracts equivalent to 0.2 g of flour were analysed by FPLC as described in Example 1. Therefore, the area under the A280 chromatograms was proportional to the relative protein content of each sample. In Riso 56, levels of the C hordeins were increased by 400% and of the B hordeins decreased by 86% compared to the parent Carlsberg 11. In Riso 1508, C and B hordeins were both reduced (91% and 86%, respectively) compared to the parent Bomi. These patterns were similar to the published data.

Identification of Seeds Having Both Hordein Mutations

Plants of the lines Riso 56 and Riso 1508 were crossed by emasculating Rise 1508 and two days later pollinating them with fresh Riso 56 pollen. Ten F1 seeds were germinated and F1 plants grown and allowed to self-fertilize. F2 seeds were harvested at maturity.

To identify double mutants in the population, half of each of 288 F2 seeds were individually crushed and ground to a powder in a plastic microtube with a stainless-steel ball, shaken at 30/sec for 3×1.5 min in a 96 well Vibration Mill (Retsch Gmbh, Rheinische). An aliquot (400 µl) of an aqueous buffer was added to each tube to extract water soluble proteins. The buffer contained 20 mM triethylamine-HCl (TEA), 1% (w/v) sodium ascorbate, 1% (w/v) PEG6000 and 1/1000 dilution of plant protease inhibitor (Sigma P9599). pH 8 at room temperature (RT). The contents of each tube were shaken again and then centrifuged at 160 g for 10min at RT. The water-insoluble flour pellet was washed twice more in the same manner and respective supernatants pooled to give the water soluble fractions. Alcohol soluble prolamins in the pellet were then extracted by adding 400 µl of 50% (v/v) aqueous propan-2-ol containing 1% (w/v) DTT and shaking the tubes as above, followed by incubation for 30 min at RT, a second round of shaking and centrifugation as above. Respective supernatants containing extracted prolamins were pooled and transferred to fresh tubes. The protein content in DTT/propan-2-ol supernatants was measured with Coomassie reagent (BioRAD) and the prolamins in a 200 µl aliquot precipitated with 4000 of propan-2-ol and stored overnight at −20° C.

An aliquot of each prolamin half-seed extract was examined for the loss of 13 and C hordeins by SDS-PAGE as described in Example 1 (FIG. 9). The screening gels were loaded on a per seed basis, with each lane carrying the equivalent of 1/20 of a seed. In particular, extracts were examined for the absence or reduction of the characteristic hordein protein bands at 40 kDa (B hordein specific) and 70 kDa (C hordein specific). Seeds of the parental lines Riso 56 and Riso 1508 were reduced for B and C hordeins, respectively, but still contained low levels of D hordeins at 100 kDa (FIG. 9). The majority of the F2 seed extracts contained a wild-type pattern with D, C and B hordeins present (FIG. 9), confirming that an effective cross between the two parental lines had been made. Sixteen seeds appeared to lack both B and C hordeins and were therefore scored as homozygous for both of the genetic lesions present in the parents. These were identified from 288 half-seeds (frequency 0.055). This was similar to the frequency of 1 in 16 (0.0625) expected for the combination of two simple, recessive mutations.

The total protein levels in the alcohol-soluble extracts of the F2 half seeds were compared to those from wild-type and parental seeds. The data are shown in Table 1. The protein levels in the extracts of the F2 seeds were reduced to less than 20%, in some cases less than 15% of the wild-type. These values may have been inflated by non-protein nitrogen compounds such as free amino-acids present in the extracts.

TABLE 1

Protein levels in alcohol-soluble extracts of F2 barley half seeds.

| Sample | Alcohol soluble protein (µg/seed ± SE) | % Bomi |
|---|---|---|
| Controls | | |
| Bomi | 512 ± 130 | 100% |
| Riso 56 | 364 ± 44 | 71% |
| Riso 1508 | 147 ± 26 | 28% |
| Double nulls | | |
| RE9 | 129.6 | 25% |
| RF8 | 89.6 | 18% |
| RH2 | 85.6 | 17% |
| BA9 | 85.6 | 17% |
| RB10 | 85.6 | 17% |
| RA9 | 82.4 | 16% |
| RG12 | 75.2 | 15% |
| BB11 | 72.8 | 14% |
| BD5 | 72 | 14% |
| BD9 | 73.6 | 14% |
| BE8 | 58.4 | 11% |
| BF8 | 59.2 | 12% |
| BB5 | 57.6 | 11% |
| RB5 | 57.6 | 11% |

The observed differences in prolamin levels between the F2 lines may have been due to the segregation of other genes or mutations from the parents.

Additional protein gels were run by taking a volume of the DTT/propan-2-ol supernatant containing 20 µg protein, drying each under vacuum in a SpeediVac, dissolving the protein in 20 µl of a buffer containing 62.5 mM Tris-HCl (pH 6.8), 12.5% (w/v) glycerol, 2% (w/v) SDS, 1% (w/v) DTT, and 0.112% (w/v) bromophenol blue, and heating in a boiling water bath for 90 sec. Each solution was loaded on a precast SDS-polyacrylamide gel, electrophoresed, stained and examined as described above. A typical gel is shown in FIG. 10. Most of the selected F2 seeds appeared to lack both the B and C hordeins and were presumed to be "double nulls". Even though each lane was loaded with the same amount of protein as measured by the dye-binding protein assay, most of the extracts from the double nulls appeared to contain substantially less protein than the controls, in particular they contained little proteinaceous material larger than 20 kDa. This might be explained by the presence of non-protein nitrogen compounds such as free amino-acids in the extracts which could have inflated the apparent protein levels as estimated by the dye-biding protein assay. This effect was also seen for extracts of Riso 1508 where the total stainable material running as protein bands was diminished compared to Riso 56 or Bomi. Riso 1508 has been shown to accumulate more non-protein N as free amino-acids (Koie and Kreis, 1978).

The cross-section of F2 seeds was also examined. When compared to wild-type, in some cases the endosperm of the apparent double null seeds appeared moderately shrunken, in others more severely shrunken.

The second half of each of the F2 seeds were germinated on moist filter paper, the F2 plantlets transferred to soil in the greenhouse and grown to maturity to provide F3 seed. Various plant growth and yield parameters were measured (Table 2).

The total water soluble and alcohol-soluble proteins from eight F3 seeds from several lines were extracted as described above. The protein content of the alcohol soluble and aqueous soluble fractions was measured as described in Example 1 using known amounts of gamma-globulin as a protein standard. However the total alcohol soluble protein levels in some samples of F3 seeds were essentially the same as Riso 1508. Subsequently it was determined that these seed samples were segregating for the wild-type allele of the Lys3a gene and were not uniformly "double null".

Quantitation of Hordein Levels in F3 Seeds by RP-FPLC

Alcohol soluble extracts from two seeds from each line were combined and 50 μl examined by RP-FPLC as described above. The chromatograms are shown in FIG. 11. The total area under the chromatograms corresponding to hordein was calculated and expressed relative to levels in a wild type line. The data (Table 3) showed that the F3 grain had hordein levels that were less than 30% of the wild-type level, in some cases less than 20%, even as low as 5.3%. The lack of substantial protein bands following SDS-PAGE supports the contention that the total alcohol protein levels were inflated due to elevated non-protein nitrogen levels in the F3 seeds.

TABLE 2

Growth and yield parameters for F2 barley plants, ranked according to 100 seed weight for the F3 seed. Red = reduced for specified hordein.

| Plant | B and C hordein phenotype | Height | No. of Tillers | Harvest index | Seeds/Head | 100 seed Weight (% of K8) |
|---|---|---|---|---|---|---|
| Sloop | WT | 36.34 ± 2.2 | 9.2 ± 0.97 | 0.60 ± 0.02 | 10.3 ± 0.7 | 5.47 ± 0.16 |
| KS | WT | 54.7 ± 1.16 | 34 | 0.63 ± 0.02 | 21.9 ± 1.4 | 4.65 ± 0.11 (100%) |
| L1 | WT | 46.6 ± 0.94 | 40 | 0.66 ± 0.01 | 22.0 ± 1.1 | 4.41 ± 0.05 (94.8%) |
| 9RE | bc reduced | 56.8 ± 2.14 | 11 | 0.56 ± 0.01 | 19.0 ± 1.24 | 4.19 ± 0.13 (90.1%) |
| R1508 | c null, Red. B | 36.41 ± 0.34 | 27.5 ± 3.5 | 0.66 ± 0.01 | 20.0 ± 0.7 | 4.02 ± 0.02 (86.5%) |
| 5RB | bc reduced | 62.0 ± 2.24 | 28 | 0.46 ± 0.02 | 15.8 ± 1.2 | 4.01 ± 0.01 (86.2%) |
| G1 | bc reduced | 61.4 ± 1.19 | 34 | 0.45 ± 0.02 | 16.0 ± 1.0 | 3.83 ± 0.09 (82.4%) |
| SBD | Red. B | 63.9 ± 1.68 | 19 | 0.45 ± 0.01 | 15 ± 0.9 | 3.70 ± 0.09 (79.6%) |
| R56 | b null | 56.2 ± 0.34 | 20.0 ± 2.0 | 0.51 ± 0.01 | 16.8 ± 1.2 | 3.70 ± 0.08 (79.6%) |
| B5 | WT | 47.3 ± 1.36 | 34 | 0.52 ± 0.02 | 14.3 ± 0.6 | 3.52 ± 0.12 (75.7%) |
| J1 | bc reduced | 50.7 ± 1.71 | 32 | 0.57 ± 0.02 | 23.9 ± 4.4 | 3.56 ± 0.03 (76.6%) |
| 4BH | Red. B | 44.9 ± 0.79 | 19 | 0.56 ± 0.01 | 19.7 ± 0.6 | 3.29 ± 0.17 (70.7%) |
| D6 | bc reduced | 42.3 ± 1.23 | 24 | 0.47 ± 0.02 | 9.2 ± 0.8 | 2.90 (62.4%) |
| 6RF | Red. B | 61.4 ± 1.66 | 23 | 0.35 ± 0.05 | 6.6 ± 1.6 | 2.86 (61.5%) |
| B1 | WT | 51.9 ± 2.79 | 12 | 0.37 ± 0.03 | 9.6 ± 1.5 | 2.62 ± 0.11 (56.3%) |
| J4 | bc reduced | 49.8 ± 0.59 | 17 | 0.35 ± 0.03 | 7.4 ± 1.1 | 2.64 ± 0.01 (56.8%) |

Plant height, head and stem weight, number of tillers, seeds per head, and 100 seed weight were measured. Harvest index was calculated from the ratio of the head weight/(stem weight+head weight). The F3 seed were then grown in the field to provide F4 seed of each line.

The F3 seeds showed a considerable variation in all measured parameters when compared to the parents and the control line, Sloop. Many of the apparent double null lines, such as J4 and 6RF, had 100 seed weights reduced by up to about 40% or reduced numbers of seeds per head relative to the wild type sibling K8. This suggested that there were other genes segregating in the population as well as the hordein B or C mutations having an effect on yield. However, several F3 lines had seed weights greater than or equal to the parents and therefore it was likely that the other genes could be segregated away from the B hordein and lys3a mutations.

In cross section, the appearance of F3 seeds varied from shrunken (similar to Riso 1508) to slightly shrunken (similar to Riso 56) when compared to wild type siblings or the control Sloop.

TABLE 3

Relative hordein levels in F3 seeds measured by RP-FPLC.

| Line | Hordein content |
|---|---|
| Wild type (K8) | 100% |
| R56 | 70% |
| R1508 | 50% |
| 4BH | 26% |
| 5RB | 21% |
| 9RE | 16% |
| J1 | 5% |

Example 4

Properties of Field-grown F4 Barley Grain

The characteristics of glasshouse grown and field grown F4 seeds of selected lines (9RE, J1, G1, 4BH), single null parents (Riso 56 and Riso 1508), and wild type barley (Sloop; Bomi; and KS, a reconstituted wild type sibling from the same cross as the double null lines) were compared.

Seed Weight

The 100 seed weight of F4 seeds grown in the glasshouse varied from 60-76% of Sloop (5.47+0.16 g per 100 seed), whereas the 100 seed weight of F4, field grown grain was lower, varying between 58-65% of Sloop (4.75 g+0.04).

Germination of Grain

Germination of seeds from two selected F4 barley lines was compared to wild-type cv. Sloop by imbibing samples of 100 grain each on moist paper for six days. Germination was observed as emergence of the root rip from the seedcoat. The F4 grains appeared to germinate at the same rate as the wild-type grain, with about 60-70% germination after 3 days. Storage of the grain at 37° C. for 4 weeks prior to imbibition slightly increased the % germination of both F4 lines. Treatment at 4° C. for 3 days also achieved the same increase over freshly harvested material.

This demonstrated that the grain of the F4 lines did not suffer any serious retardation of germination, and therefore were predicted to be agronomically useful.

Protein Levels in F4 Grain

The levels of water-, salt-, alcohol-, and urea-soluble proteins in grain of the F4 lines were measured using duplicate 20 mg samples of wholemeal flour from glasshouse grown, F4 seeds of selected lines (9RE, J1, G1, 4BH), single null parents (Riso 56 and Riso 1508), and wild type barley (Sloop; Bomi; and K8).

Water-soluble proteins were extracted from each flour sample using 0.5 ml of water, by mixing for 30 min, centrifuging the mixture at 13,000 rpm for 5 minutes, removing the supernatant, and repeating the extraction on the pellet twice. The supernatants were pooled (water-soluble extract) and the pellet sequentially extracted three times in the same manner using 0.5 ml of 0.5M NaCl (salt-soluble extract), followed by 0.5 ml of 50% (v/v) propan-1-ol containing 1% (w/v) DTT (alcohol-soluble extract (hordeins)), followed by 8M urea containing 1% (w/v) DTT (urea-soluble extract). The protein content of each fraction was measured by using a dye binding assay (BioRad) according to the manufacturer's instructions, calibrated against gamma globulin as a protein standard. The data are shown in FIG. 12. The total extractable protein content (FIG. 12E), was calculated from the sum of the protein contents of all the soluble fractions.

In addition the total nitrogen (Total N; FIG. 12F) was measured using duplicate 2.5 mg samples of the same flour by elemental analysis following combustion at 1800° C. and reduction to $N_2$ at 600° C., and quantification by mass spectroscopy (method of Dumas). The total protein content was calculated using the expression: protein content 6.63× amount of total N. The figures obtained for total protein levels by MS were reasonably similar to the estimated total extractable protein contents, showing that the protein extraction was efficient.

The hordein content (measured as the level of alcohol-soluble protein) of the F4 grain was reduced to 17-39% of the parents (R1508 and R56) and to 7-16% of the wild type cultivar Sloop. This represented about a 10-fold reduction in the level of total hordeins, shown above to be toxic to coeliacs, in these grain samples relative to wild type barley, Sloop.

The other types of proteins, in particular the water- and salt-soluble proteins are thought to have beneficial effects on the brewing properties of barley grain. Since the levels of water- and salt-soluble proteins of the F4 grains were similar to those in the wild-type, Sloop, it was considered that the F4 grains would have sufficient of these proteins for brewing purposes.

Fatty Acid Content and Composition

Since a major nitrogen sink during growth and development of the seeds had been removed by reducing the hordeins, the mutant grain was analysed to determine whether the developing seed might have compensated by increasing the storage of for other components, some of which could be deleterious to use of the grain. The fatty acids in duplicate 50 mg samples of wholemeal flour from F4 grain were extracted, methylated and analysed by quantitative gas chromatography (GC) using the method of Folich et al. (1957).

The total fatty acid concentration in the F4 grain of lines G1, BB5, J1, and J4 varied in the range from about 2.5% to 3% (w/w), and was similar in level to that in the single null and the wild type barley grain. It was concluded that the double null grains did not contain elevated levels of fatty acids.

The fatty acids in the grain lipid comprised mainly linoleic (C18:2), oleic (C18:1) and palmitic acids (C16:0), with lower levels of other fatty acids. There was no significant difference in the concentrations of individual fatty acids that had accumulated in the selected F4 grain compared to the single null parents or the wild type barley. In particular, the concentration of erucic acid (C22:1n-9), which is toxic to humans in high concentration, in the F4 grain was not increased. The mutant grain therefore had non fatty acid content and composition.

Starch Levels

Starch is the main component of cereal grain, typically comprising about 55-65% of the dry weight. Starch levels are particularly important in barley which is used for malting, A starch content which is too low may result in the formation of malt which has insufficient sugar content to enable efficient fermentation to occur during brewing, and therefore starch levels in the barley grain were measured.

Starch of the mutant grain was isolated and assayed essentially as described in the Megazyme Method (AACC76.13) using 20 mg of whole meal flour samples. Total starch levels in the F4 grain were in the range from 57% to 66% (w/w), and were similar to the starch content of the single null parents and the wild type barley which were in the range of 51-64% (w/w).

It was concluded that the F4 barley grains had sufficient starch to enable production of malt from the grain.

β Glucan Levels

The β-glucan content in the mutant grain was assayed as described in Megazyme Method (AACC32,23), using 20 mg samples of wholemeal flour. β-glucan levels in the grain of lines G1, BB5, J1, J4 were in the range from 1.2 to 2.6% (w/w), and were similar to the β-glucan content of the single null parental grain and the wild type barley grain which were in the range from 2.4-3.3% (w/w).

High β-glucan levels are involved in the formation of chilling haze in beer during storage. It was concluded that the β-glucan content of the F4 grains was not elevated when compared to wild-type grains and the levels were unlikely to interfere with the brewing performance of these grains.

Free Amino Acid Levels

Increased accumulation of free amino-acids could possibly be deleterious for use of the grain. For example, free asparagine in sufficient amounts might form the toxic compound acrylamide if heated to high temperatures in the presence of starch.

The content and composition of free amino-acids in the grain was measured using replicate samples of 20 mg wholemeal flour from glasshouse grown, F4 seeds. Samples were dissolved in 0.1N HCl and an aliquot was taken and dried, and amino acids analysed using the Waters AccQTag chemistry by the Australian Proteome Analysis Facility (Sydney).

The most prevalent amino acids in the barley flours were proline, asparagine, glutamic and aspartic acid in decreasing order, in the range of about 1.5 mg/g flour down to 0.5 mg/g flour. The free proline content in the selected F4 grain was in the range 0.6-1.5 mg/g, and was similar to the free proline content of the single null parents and the wild type barley which were in the range 0.2-1.2 mg/g. Levels of all other free amino-acids were correspondingly similar in F4 and control grains. In particular, the free asparagine content in the F4 grain was about 0.5 mg/g for lines G1, BBS and J1 and about 1.0 mg/g in line J4. In the single null parental grains, the free asparagine level was 0.3 or 0.9 mg/g, and in the wild type barley grains, free asparagine was in the range from 0.3-0.6 m/g.

Since the free asparagine content of the F4 grain was similar to levels in the corresponding wild type grain, it was considered that the production of acrylamide from free asparagine during malting or other use of the grain would be no different than for the wild-type grain.

Free lysine is known to be a limiting amino-acid in animal nutrition and therefore levels of this amino acid were of interest for potential use of the grain as animal feed. The free lysine content in the F4 grain of lines G1, BB5 and J1 was about 0.5 mg/g and 1.0 mg/g in grain of the line J4. This represented a 181% -1,020% increase compared to the level in wild-type grain of cultivar Sloop. Thus the F4 lines were a more nutritious source of free lysine than Sloop.

Example 5

Testing of F4 Grains—T-cell Toxicity Testing

To test the coeliac toxicity of the F4 grain, hordeins were isolated and purified from 10 g samples of wholemeal flour from field grown seeds of selected lines 9RE, J1, G1 and 4BH, single null parents (Riso 56 and Riso 1508), and wild type barley (Sloop; Bomi; and K8) as described below. The purified hordeins were adding to T-cells isolated from a population of coeliacs to test for coeliac toxicity. The test involved measuring the number of T-cells which produced gamma-interferon following overnight incubation with the purified protein, using an antibody assay for the level of gamma-interferon. That is, the level of gamma-interferon was an indication of the extent of toxicity of the proteins in the grain. This measure of the coeliac toxicity of the flour was then plotted as a function of the fresh weight of flour obtained from the grain.

Purification of Prolarnins (Hordeins)

Wholemeal flour (10 g) was stirred for 30 min at 25° C. in 200 ml of buffer containing 20 mM triethanolamine-HCl (TEA), 1% (w/v) sodium ascorbate, 1% (w/v) polyethylene glycol (MW 6000; PEG 6000), and 1 µg/ml of protease inhibitors E64 and AEBSF (Sigma); the buffer adjusted to pH 8. The suspension was centrifuged at 5,000 g for 5 min, the supernatant discarded and the pellet washed twice more. Proteins in the washed pellet were dissolved in 80 ml of 50% (v/v) propan-2-ol, containing 1% (w/v) DTT, by stirring for 30 min at 60° C. The suspension was chilled at 4° C. for 10 minutes and centrifuged at 10,000 g for 10 min at 4° C. The proteins including hordeins in the supernatant were precipitated with 2 volumes of propan-2-ol overnight at −20° C., and sedimented at 10,000 g for 10 min at 4° C., and the pellet dissolved in 10 ml of buffer which contained 8M freshly deionised urea, 1% DTT, 20 mM TEA, adjusted to pH 6.

The hordeins were purified by FPLC as follows. The hordein solution (1 ml) was injected into an 8 ml column of Source 15 Reverse Phase Chromatography (RPC, Pharmacia). The column was washed with 4 ml of 5% solvent B, and hordeins eluted with a 2.5 ml linear gradient from 5% solvent B to 35% solvent B at 4 ml/min, followed by a linear gradient from 35% solvent B to 83% solvent B over 36 ml. Solvent A was 0.1% (v/v) trifluoroacetic acid (TFA) in water, solvent B was 0.1% (v/v) TFA in 60% (v/v) aqueous acetonitrile. Fractions eluting between 25 and 43 ml were pooled. Solvent controls were similarly pooled from runs without an injection. Corresponding pools from 10 sequential injections were combined, and lyophylised.

Ex Vivo T-cell Assays

FPLC purified hordeins (50 mg/ml in 2M urea) were diluted with PBS containing 1 mM $CaCl_2$, to give either 25, 62.5, 125, 250, 625, 3,750, or 6250 µg hordein/ml and deamidated by adding 25 µl of each solution to 100 µl of guinea pig liver tTG (Sigma; 25 µg/ml tTG in PBS containing 1 mM $CaCl_2$) and incubated for 6 hr at 37° C. Non-deamidated solutions were similarly prepared by incubation in the absence of tTG. Solvent controls were added as for the highest hordein concentrations. Other control samples contained either the solvent control, the solvent control containing a known toxin, the tetanus toxoid (50 light forming units/ml, obtained from Commonwealth Serum Laboratories, Melbourne); or tetanus toxoid (50 light forming units/ nil) alone. All solutions were then frozen at −20° C.

T-cells were obtained as follows. Six, biopsy-proven, HLA-DQ2$^+$ coeliac subjects, adhering to a strict gluten-free diet for at least three months, consumed 150g of boiled barley daily for 3 days. PBMC were isolated by Ficoll-Hypaque density centrifugation from heparinised venous blood collected either immediately prior to or six days following commencement of dietary challenge, and resuspended in complete HT-RPMI containing 10% heat-inactivated, pooled, human AB serum. Deamidated or non-deamidated hordeins and control solutions were thawed and 25 µl added to wells containing 100 al of PBMC (3-8×105 PBMC per well), cultured at 37° C. overnight in 96-well plates (MAIP-S-45; Millipore, Bedford, Mass.) and compared to control cultures (no addition) to which was added 25 µl of PBS containing 1 mM $CaCl_2$ alone. Final hordein concentrations were 0, 1, 2.5, 5, 10, 25, 150, or 250 µg/ml. The highest final urea concentration was 10 mM. IFN-γ was visualised using secondary antibodies as in manufacturers notes (Mabtech, Stockholm, Sweden) as previously described by Anderson et al. (2005), and spot forming units (SFU) counted using an automated ELISPOT reader (AID Autoimmun Diagnostika GmbH; Germany). Results are presented as the mean spot forming units (SFU)±S.E vs the equivalent weight of flour which would contain the calculated amount of hordein. The hordein content of each flour sample was calculated in Example 5, allowing calculation of the weight of flour.

Data was analysed by GraphPAD Prism and the curves of best fit calculated and shown with means+S.E. The $r^2$ values for the data were greater than 0.83, indicating a good fit between observed data and the curve of best fit (FIG. 13).

Results

T-cells isolated from a single coeliac subject prior to a dietary challenge were less responsive to prolamin added at 25 µg/ml than T-cells isolated from the same individual after a dietary challenge with barley. The mean SFU±S.E. of 29.5±3.0, and 104±15.9 were observed for T-cells isolated before and after a dietary challenge. This indicated that coeliac specific T-cells were induced by the dietary challenge.

Using T-cells isolated six days after the dietary challenge, the positive control, tetanus toxoid, gave a consistent response in the absence and presence of tTG (mean 28.1±5,9 and 20.2±7.4, respectively). Addition of the solvent control did not significantly inhibit the response of the positive tetanus toxoid control (mean SFU±S.E. 20.5±4.1 and 17.6±6.0 in the absence and presence of tTG respectively) confirming that solvent impurities did not generate false negatives or inhibit the positive responses.

T-cells isolated from coeliacs, 6 days post challenge responded more strongly to all tTG treated hordein fractions when compared to T-cells exposed to non-deamidated hordeins as expected for coeliac disease (Hadjivassiliou et al., 2004, Kim at al., 2004) (FIG. 13A; for clarity the response to only two hordein samples, Sloop and G1, are shown). This confirmed that the T-cell response being measured was related to coeliac toxicity.

As the concentration of hordein was increased, the number of SFU also increased in a hyperbolic manner as expected for normal Michaelis-Menten enzyme kinetics between an enzyme and its substrate. Two parameters are generally used to describe such curves: Bmax, the maximum number of SFU expected at the highest concentration; and Kd, the concentration of protein required to induce half maximal SFU. The more toxic the flour sample, then the lower the Kd.

The coefficients Kd and Bmax were calculated from the curves of best fit. The Borax values did not vary significantly between wild-type and mutants, as expected. In contrast, the Kd values for the F4 lines were higher by a factor of 10 compared to the wild type lines (Table 4). That is, approximately 10 times more flour from the mutant lines was required to induce half maximal toxicity response than for the wild-type flour (Table 4). Thus it was concluded that the coeliac toxicity of the F4 grain had been reduced by about 10-fold compared to the wild type lines. This level of reduction compared well with the decreased hordein level found by protein determination in the F4 grain.

TABLE 4

T-cell toxicity of barley flour.

| Line | | Kd (mg of flour for half maximal spots) |
|---|---|---|
| Wild Type: | Sloop | 0.18 ± 0.03 |
| | Bomi | 0.18 ± 0.02 |
| Single null: | Riso56 | 0.47 ± 0.09 |
| | Riso1508 | 3.31 ± 0.47 |
| F4 lines: | G1 | 2.3 ± 0.3 |
| | 5RB | 2.6 ± 0.5 |
| | 4BH | 1.7 ± 0.2 |
| | J1 | 1.4 ± 0.2 |

The toxicity of the F4 grain was lower than that of Riso 56 as expected. However the toxicity of the F4 grain was similar to that of the other parent Riso 1508. Subsequently, on further genetic characterisation of the F4 grain, it was found that this was due to heterozygosity of the mutation of the gene encoding B-hordein protein in the selected F4 lines, which had the effect of elevating the hordein content above that expected.

Example 6

Making of F4 Grain

To determine the suitability f the barley grain for malting, analyses including small-scale malting (micro-malting) tests were carried out.

One factor that influences malting ability is seed size. Samples from the F4 grain were analysed for seed size distribution by counting the proportion of 1,000 seeds which were retained by 2.8, 2.5 or 2.2 mm screens. The F4 grain on average were smaller than wild-type and similar to the parental grains Riso 1508 and Riso 56 with less than 5% of the seed retained by a 2.5 mm sieve (Table 5). This contrasted to the control lines Galleon and Sloop where 90% of seed was greater than 2.5 mm. It was noted that grains of K8 which is a wild-type line derived from the same Riso 1508 X Riso 56 cross were also reduced in size, therefore at least part of the reduction in seed size was related to the genetic background and not directly due to the reduced hordein level. In addition, the smaller seed size could be compensated for by modifications in the method for steeping of the grain.

TABLE 5

Size of seed used for micromalting.

| Line | % seed population retained by 2.5 mm sieve |
|---|---|
| G1 | 1.0 |
| 4BH | 2.6 |
| 5RB | 3.2 |
| J1 | 2.0 |
| 9RE | 6.2 |
| Riso 1508 | 4.0 |
| Riso 56 | 6.9 |
| K8 | 24.8 |
| Bomi | 56.6 |
| Carlsberg II | 57.5 |
| Galleon | 83.9 |
| Sloop | 91.6 |

Seed moisture levels may affect the malting performance. The % moisture and % nitrogen were measured by Near-Infra-Red (NIR) analysis prior to micro-malting. The level of seed moisture of all the F4 grain samples was in the range between 11 and 11.4% and was similar to the control lines except for grain of cv. Galleon (GA1, 8.9%). Seed nitrogen for the double null lines ranged between 2.3% and 2.5% which was higher than the control malting line cv. Galleon, at 1.6%. For malting, seed nitrogen levels is optimally between 1.5 and 2.0%.

Barley samples (170 g) from field grown, F4 grain from the selected lines 5RB, G1, J1, 9RE, 4BH, single null parents (Riso 56 and Riso 1508), and wild type barley K8, cultivars Bomi, Carlsberg II, Sloop and Galleon were steeped at 16° C. by soaking for 6 hrs, followed by resting for 7 hr in air, followed by soaking for 6 hr, and then germinated at 15° C. for 4 day in a JWM micromalting system. The germinated grain was kilned for 21 hr at a minimum temperature of 50° C., and a maximum temperature of 80° C., and the resulting malts were cleaned of their roots by rubbing and sieving.

The malts were analysed for moisture (%), total nitrogen (% dry wt) by whole grain NIR and yield (expressed as weight of cleaned malt as a percentage of initial weight of barley).

In addition, malt samples were ground in a hammer mill and 50g samples dissolved in water heated from 45° C. to 70° C., to give 450 g final weight of solution which was analysed for extract (% of grain weight solubilised), colour, soluble nitrogen (N), Kohlbach index (KI: % soluble protein/total protein), β-glucan, viscosity, AAL (apparent attenuation limit or fermentability, % drop in density during fermentation with brewers yeast), each according to the standard European Brewery Convention protocols, www.ebc-nl.com (Table 6).

The protein content of the malts was generally higher than desirable specification. This was shown by the total malt N, and the soluble N, however the proportion of soluble protein compared to the total (KI) was close to specification. The colour and viscosity of the F4 worts was close to specification and the β-glucan levels in the worts were low. These features were acceptable for malting.

The malting process involved three stages: malting, worting fermentation. The overall efficiency is calculated from three measures of the efficiency of each stage: yield, extract, and AAL respectively. These indicate that at each stage the F4 grain are approximately 10% less efficient than the benchmark grain, cv Galleon. Overall approximately 1,3-fold more grain of the F4 lines would be required to produce beer of a strength equivalent to the commercial standard, compared to Galleon.

All of these indications showed that malt could be made from the F4 grains.

milk powder in PBS buffer containing 0.1% Tween 20, for 1 hr at room temp. Hordeins were detected with a primary antibody (rabbit anti-wheat gliadin, antibody conjugated to horseradish peroxidase, from Sigma), diluted 1 part in 2000 of PBST buffer, for 30 min at room temperature. The membrane was washed with three changes of PEST buffer and developed by incubating in 10 ml of a 1:1 (v/v) mixture of reagents Amersham ECL western blotting reagents A and B (GE HealthCare) and the signal detected by exposing to Amersham Hyperfilm for 30 sec. The film was developed and quantitated using Total Lab TL100 software (Non-linear dynamics, 2006).

The raw malt solutions produced from the selected F4 grain had a mean level of hordein of 58±12.7 ppm.

This level was substantially lower than the limit of 200 ppm set by FSANZ for low gluten food in Australia and considerably lower than the mean. of 687±158 ppm found for malt from the wild type cultivars Galleon, Sloop, K8, Bomi, and Carlsberg H. It was also considerably lower than the hordein content of malt made from the parents Riso 56 and Riso 1508.

Ordinarily, the gluten (hordein) content of mixtures falls dramatically through the malting, worting and fermentation processes, and final stabilised beer may contain 1/1000 the level present in raw malt (Dostalek et al., 2006).

Therefore it was predicted that the hordein level in processed beer made from the F4 malts would be reduced to

TABLE 6

Malt and wort analysis.

| | Malt Analysis | | | Wort Analysis (according to EBC) | | | | | | |
|---|---|---|---|---|---|---|---|---|---|---|
| Line | Moisture % | Total N % dry wt | Yield % | Extract | Colour | Soluble N % dry wt | KI | βGlucan mg/L | Viscosity mPa · sec | AAL % |
| Specification | <5% | 144.1-1.9 | >85 | >80% | 3.0-4.5 | 0.6-0.8 | 38-46 | <180 | >1.6 | >82 |
| 5RB | 4.6 | 3.04 | 75 | 69.3 | 12.4 | 1.57 | 52 | 25 | 1.54 | 75.0 |
| G1 | 4.9 | 3.18 | 77 | 69.2 | 6.1 | 1.64 | 52 | 24 | 1.47 | 71.8 |
| J1 | 4.5 | 3.15 | 75 | 71.2 | 6.1 | 1.47 | 47 | 27 | 1.49 | 74.2 |
| 9RE | 4.0 | 2.88 | 80 | 75.1 | 5.1 | 1.37 | 48 | 41 | 1.47 | 70.0 |
| 4BH | 4.1 | 2.82 | 79 | 71.1 | 5.0 | 1.37 | 49 | 34 | 1.47 | 71.7 |
| Riso 1508 | 3.9 | 2.63 | 84 | 75.2 | 4.5 | 1.25 | 48 | 89 | 1.43 | 70.7 |
| Riso 56 | 4.0 | 3.54 | 83 | 72.1 | 3.8 | 1.11 | 31 | 194 | 1.40 | 75.9 |
| K8 | 4.1 | 2.78 | 86 | 73.7 | 2.9 | 0.79 | 28 | 396 | 1.64 | 67.9 |
| Bomi | 4.2 | 2.97 | 86 | 75.6 | 3.6 | 0.79 | 27 | 509 | 1.53 | 72.5 |
| Carlsberg II | 4.3 | 3.04 | 86 | 72.9 | 2.6 | 0.66 | 22 | 612 | 1.63 | 68.9 |
| Galleon | 3.8 | 1.59 | 88 | 81.5 | 3.3 | 0.58 | 36 | 233 | 1.56 | 79.2 |
| Sloop | 4.0 | 2.73 | 86 | 74.2 | 3.2 | 0.87 | 32 | 229 | 1.56 | 77.6 |

Example 7

ELISA Analysis of Raw Malt Samples

Approximately 40 ml samples of wort from Example 6 were frozen, lyophylised, and dissolved in 20 ml of 6M urea, 1% (w/v) DTT, 20 mM TEA (pH 6) at room temperature. The protein content of each sample was determined using the dye binding method of Bradford. Serial dilutions containing 20 μg of malt protein in 100 μl of 6 M urea, 1% DTT, and 20 mM TEA (pH 6) were applied to a nitrocellulose membrane (Amersham Hybond C+) which had been pre-equilibrated in PBS buffer, in a dot blot apparatus (BioRad) and calibrated with a purified C-hordein standard (2 μg). The solution was drawn through the membrane under reduced pressure, and the membrane rinsed with PBS buffer containing 0.1% Tween 20 (PBST), the apparatus dissembled and the membrane blocked by incubating in 5% (w/v) skim approximately 0.05 ppm, well below the range of 3-40 ppm found for beers made from wild-type barley grain (Dostalek at al., 2006).

There are several recent recommendations in the literature for the limit of gluten in the diet of coeliacs. The most reliable of these is based on a multi-centre, placebo controlled, double blind trial and shows that consumption of less than 10 mg/day is safe for coeliacs; and recommends that consumption should be kept to less than 50 mg/day (Catassi et al., 2007). Another recent study confirms these findings and (Collin et al., 2004) advises that consumption of food with 100 ppm gluten would result in consumption of about 30 mg/day and result in little damage to coeliacs. FSANZ sets the food standards for New Zealand and Australia. The Codex Alimentarius Commission was created in 1963 by FAO and WHO to develop food standards, guidelines and related texts such as codes of practice under the Joint FAO/WHO Food Standards Programme and is the accepted statutory regulation for Europe, and North America. The Codex currently sets a gluten free limit of less than 0.05 g N (as gluten) per 100 gm of food. There is a proposal to revise the Codex standard and proposes a limit of 20 ppm for food made from non gluten containing cereals, and 200 ppm for food made from gluten containing cereals (p32, PROPOSAL P264, REVIEW OF GLUTEN CLAIMS WITH SPECIFIC REFERENCE TO OATS AND MALT, FSANZ web site:

www.foodstandards.gov.au/_srcfiles/P264_Gluten_Claims_FAR.pdf#search=% 22gluten %20free %22).

It was concluded from the above analysis that consumption of beer produced from the F4 barley lines would be well below the safety limit set for gluten free food for coeliacs, in the above studies and including the regulations set by FSANZ and the Codex Alimentarius.

Example 8

Further Characterisation of the F4 Lines

Alcohol soluble proteins were purified from bulk F4 seed harvested for each of the indicated lines, as described above, Purified protein samples (20 µg) from the F4 grain of lines G1, J1, 4BH, 5RB and 9RE were dissolved in 6M urea, 2% (w/v) SDS, 1% (w/v) DU, 0.01% (w/v) bromophenol blue, 0.0625 M Tris-HCL (pH 6.8) at 25° C., examined by SDS-PAGE, stained with 0.006% colloidal Commassie Blue, and compared to hordeins isolated from Riso 56, Riso 1508, and wild type lines (KS). Migration was compared to molecular weight standards to determine molecular mass (Table 7).

Protein sequences were obtained by mass spectroscopy of tryptic digests from protein spots cut from the gels, and processed for protein sequencing by MS-MS fragmentation as previously described (Campbell et al., 2001) with a search against the NCBI non-redundant database.

TABLE 7

Protein identification from SDS-PAGE.

| Spot no. | ID[A] | Matched peptides (% protein) | NCBI Accession | Summed MSMS score | Confidence[E] |
|---|---|---|---|---|---|
| 3 | D-hordein | 15 (20%) | 30421167 | 205 | Certain |
| 4 | B3-hordein[B] | 9 (27%) | 82371 | 122 | Certain |
| 5 | gamma-3-hordein[C] | 3 (11%) | 1708280 | 47 | Reliable |
| 6 | gamma-hordein-1 precursor | 1 (2%) | 123464 | 14 | Indicative of homology only |
| 7 | gamma-hordein-1 precursor | 6 (24%) | 123464 | 94 | Certain |
| 8 | gamma-3-hordein[D] | 14 (30%) | 1708280 | 199 | Certain |

[A]All digests also contain peptides from porcine trypsin, as expected.
[B]Also contained a low level of D-hordein
[C]Also contained low level of B-hordein.
[D]Also contained low level of gamma-hordein-1 precursor
[E]The summed MSMS search score indicates the confidence of the identity assignment. From past experience, a score of over 15 is required for a reliable identification, and a score of over 50 indicates almost certain identification.

Peptides from each sample were bound to an Agilent Zorbax SB-C18 5 µm 150×0.5 mm column with a flow rate of 0.1% (v/v) formic acid/5% (v/v) acetonitrile at 20 µl/min for one min then eluted with gradients of increasing acetonitrile concentration to 0.1% (v/v) formic acid/20% (v/v) acetonitrile over one min. at 5 µl/min, then to 0.1% (v/v) formic acid/50% (v/v) acetonitrile over 28 min, then to 0.1% (v/v) formic acid/95% (v/v) acetonitrile over one min. The column was washed with a gradient from 0.1% (v/v) formic acid/95% (v/v) acetonitrile to 0.1% (v/v) formic acid/100% (v/v) acetonitrile over 5 min at 20 µ/min and re-equilibrated with 0.1% (v/v) formic acid/5% (v/v) acetonitrile for 7 min before peptides from the sample were applied.

Eluate from the column was introduced to an Agilent XCT ion trap mass spectrometer through the instrument's micronebuliser electrospray ion source. As peptides were eluting from the column, the ion trap collected full spectrum positive ion scans (100-2200 m/z) followed by four MS/MS scans of ions observed in the full spectrum according to the instrument's 'SmartFrag' and 'Peptide Scan' settings.

Once two fragmentation spectra were collected for any particular m/z value it was excluded from selection for analysis for a further 30 sec to avoid collecting redundant data.

Mass spectral data sets matched with sequence databases using Agilent's Spectrum Mill software (Rev A.03.02.060). False positive matches were avoided by using the software's 'autovalidation' default settings. This includes a requirement for the peptide matches to be considerably better than the best match against the reversed database and various weightings favouring more probable ionisation and fragmentation patterns ('proton mobility scoring'). Oxidised methionine was allowed as a variable modification.

The results of protein sequencing established that the F4 seed from the selected lines unexpectedly contained a B3-hordein band, in addition to gammal-hordein and D-hordein as expected. The identity of the gamma-1 and-3 hordein bands were established by sequencing proteins from the Riso 56 mutant where these proteins were not masked by co-migrating B-hordein bands. This indicated that the selected F4 lines were not completely lacking the B3 hordein.

Example 9

Identification of Barley Grain Lacking B and C Hordeins

Individual half seeds from a single head of field grown, F4 plants of line G1 were swollen overnight in water containing protease inhibitors E64 and AEBSF (1 µg/ml), individually crushed and ground in a plastic microtube with a stainless-steel ball, shaken at 30/sec for 3×1.5 min. in a 96 well Vibration Mill (Retsch Gmbh, Rheinische) and then centrifuged at 3000 g for 5 min at RT and the supernatant discarded. The water-insoluble flour pellet was washed twice more in the same manner and the supernatants discarded. Alcohol soluble hordeins in the pellet were then extracted by adding 400 µl of 50% (v/v) aqueous propan-2-ol containing 1% (w/v) DTT, followed by shaking and centrifugation as above. Supernatants containing extracted hordeins were transferred to fresh tubes and the protein content in the DTT/propan-2-ol supernatants measured with Coomassie reagent (BioRAD).

An aliquot of each hordein extract corresponding to 20 µg of hordein was lyophylised under vacuum overnight, dissolved in 15 µl of SDS-boiling buffer, heated for 3 min at 90° C., loaded on a precast 12-18% Excell gradient gel (Pharmacia) and examined by SDS-PAGE as described in Example 1. A prominent band at approximately 43 kDa was observed to segregate in individual seeds and was absent in extracts of 5 out of 16 seeds. The position of this band was the same as the B3-hordein band identified previously.

The protein data confirmed that the F4 seed from line G1 was heterozygous and segregating for one or more B-hordein proteins. This situation was also confirmed for other F4 lines.

Genetic Testing

Genetic tests were carried out to confirm the protein data Individual half-seeds from field grown, selected F4 lines were germinated in moist soil, and grown for 2 weeks in the glasshouse at 25° C. days and 20° C. nights. DNA was isolated from 0.5 cm of the leaf blade using a REDExtract-N-Amp Plant PCR Kit (Sigma) according to the instructions. Gene sequences specific for B1-hordeins and gamma-hordeins were amplified by separate PCR reactions by adding 10 l of RMix, 1 µl each of the B1-hordein primers (5'B1hor and 3'B1hor) or 0.5 µl each of the gamma3-hordein primers (5'gamma hor3 and 3'gamma 3-full), 4 µl plant DNA and MilliQ water to 20 µl, at room temperature and then subjected to the following temperature programme in an Eppendorf thermal cycler: 95° C. for 10 mm; followed by 35 cycles of 95° C. for 30 sec, 56° C. for 30 sec, and 72° C. for 1 min. This was followed by 72° C. for 10 min, and cooling to 10° C.

The sequences of the PCR primers were as follows:

```
                              (SEQ ID NO: 2)
5'B1hor:      5'-CAACAATGAAGACCTTCCTC-3'

(SEQ ID NO: 3)
3'B1hor:      5' -TCGCAGGATCCTGTACAACG-3'

(SEQ ID NO: 4)
5' gamma hor3:  5'-CGAGAAGGTACCATTACTCCAG-3'

(SEQ ID NO: 5)
3' gamma 3-full:  5'-AGTAACAATGAAGGTCCATCG-3'.
```

20 µl of each PCR reaction was loaded on a 1 cm, 1% (w/v) agarose gel containing EtBr, electrophoresed at 100 V for 1 hr in TBE buffer and an image obtained of the fluorescence of the DNA products using GelDoc image system (uvitec) (FIG. 14).

An amplified DNA band for the gamma3 hordein control gene was present in all lanes as expected (FIG. 14, lower panel, gamma3-Hor). Amplified B-hordein DNA was absent in all PCR lanes from Riso 56, as expected the gene has been deleted in Riso 56 (FIG. 14, top panel, R56). Amplified DNA bands for B-hordein genes segregated in extracts from seeds of a single head of F4 lines 9RE and 4BH (FIG. 14, top panel 9RE, 413H). This indicated that one or more B-hordein genes were present in some of the F4 seed and that the F3 seed were not homozygous for the deletion of the B-hordein locus in Riso 56. This was also shown for other F4 lines. This method was useful as a DNA-based method to identify and select seeds lacking the B1 hordein.

The results of the genetic testing were used to select for plants that did not contain B-hordein genes. Twelve individual F5 plants, null by PCR for B-hordein genes were selected, and grown to produce a population of F5 seeds known as G1*. Individual G1*, F5 half seeds, were taken from a single head, germinated in moist soil and grown for 2 weeks in the glasshouse at 25° C. days and 20° C. nights before DNA isolation/PCR analysis as above. The corresponding half-seed was used for hordein isolation and analysis by taking an aliquot corresponding to 40 µg of hordein, lyophylised under vacuum overnight, dissolved in 15 µl of SDS-boiling buffer, heated for 3 min at 90° C., loaded on a precast 12% Longlife, 1 mm gel (Longlife Gels) and electrophoresed at 150V for 40 min and stained as in Example 1.

The PCR analysis showed that DNA isolated from the positive control lines. Sloop and Riso 1508 gave a B-hordein band as expected. The size of the band from Sloop was larger than that amplified from Riso 1508, since the B1-hordein genes were slightly different, The control gene, gamma3-hordein, was amplified from all plants. The PCR band was not amplified from extracts of six G1* individuals confirming the absence of the gene from these plants. The hordein pattern in the corresponding half seeds confirmed this; no B-hordein bands were observed in G1*. Therefore it was concluded that G1* lacked detectable B-hordeins and was inferred to be a homozygous null for the locus encoding B-hordein.

The remaining 250 G1* seeds were germinated and the seedlings tested and confirmed as null for the B-hordein gene. Subsequent generations were used for seed increase of this line.

Analysis of Hordein Content

The barley varieties Sloop, R56, R1508 and G1* were grown in adjacent plots in the field, the mature grain harvested and processed to make flour. Hordein levels in the flour samples were analysed as described above. Protein fractions soluble in water, salt solution, alcohol/DTT and urea soluble were obtained as in Example 4 and the protein content in each measured. The protein contents are shown in Table 8, and expressed as mg protein/gm dry weight flour. Each total protein content was determined by summing the protein content of the fractions for that sample. Hordeins were contained in the alcohol soluble fraction along with other alcohol soluble proteins such as serpins, protease inhibitors, LTP1 and Protein Z.

TABLE 8

Protein content in fractions in flour obtained from G1* grain.

| Barley Variety | Water soluble | Salt soluble | Alcohol/DTT (% Sloop) | Urea soluble | Total |
|---|---|---|---|---|---|
| Sloop | 17.2 | 17.6 | 23.1 (100%) | 48.0 | 106 |
| R56 | 16.7 | 19.0 | 13.2 (58%) | 58.6 | 108 |
| R1508 | 22.2 | 15.0 | 8.0 (35%) | 53.5 | 99 |
| G1* | 19.0 | 22.2 | 4.8 (21%) | 58.6 | 105 |

The data showed that the alcohol soluble protein content in G1* grain and consequently the flour was reduced to less than 22% relative to the wild-type cultivar Sloop.

The alcohol soluble protein fractions obtained above were enriched for hordeins by FPLC as in Example 5. The proteins in each FPLC eluate were lyophylised and the yield of FPLC-purified protein per 10 g of flour determined. This showed that the hordein content of G1* was reduced to less than 8 mg/10 g flour compared to 105 mg/10 g flour for Sloop, 38 for R56 and 24 for R1508. This represented a reduction in the hordein content in G1* grain and flour of at least 92% relative to Sloop.

Example 10

Larger Scale Malting and Brewing Using F4 Grain

Larger scale malting experiments were carried out to produce sufficient quantities of malt for brewing tests using the F4 grain. These tests used modified steeping procedures, to take account of the smaller grain size amongst other factors, as follows. Grain samples of 800 g per malting tin were used. Steeping regime was 17° C. for 5 hours, germination temperature was 15° C. for 94 hours. The kiln program was 50-78° C. for 17 hours, 50-74° C. for 17 hours. Malt production did not use gibberellic acid, this was not needed.

Mashing recipe: 4.65 kg low gluten malt, 10 litres water, 10 g calcium chloride, 2 g calcium sulphate, 64-65° C. for 2 hours.

Kettle: add 17 g Target Hop Pellets (10.0% AA) for 60 min, 21 g Hallertau Hop Pellets (4.5% NA) for 10 minutes.

Fermentation was in 19 litre batch volume, at 12° C. fermentation temperature, using 12 g Fermentis W34/70 dry yeast, for 8 days primary fermentation, then 9 days chilled at 0° C. The beer was then filtered through a 1 micron filter, force carbonated in a keg, and filled with a counter-pressure bottle filler. The original specific gravity was 1.044, final gravity of fermented product was 1.013 with an Approximate Bitterness of 30 IBU, and the Approximate Alcohol by volume was 4.0%.

Other parameters measured during the production process were as follows: Malt moisture: 4.2%, Extract 71.5; Colour 3.9; WC 1.0; TN 2.63% dry basis; SN 1.11; KI 51; Viscosity 1.52; AAL 71.8%; beta-glucosidase 130 mg/l; DP 24.

All of these indications showed that beer could be made from the malt from the F4 grains.

Larger scale malting and brewing tests were also performed on G1* barley grain. Eight hundred gm of grain was malted in a Joe White Mailings automated limiter, according to the indicated protocol. Preferred malting conditions for G1* grain was determined to be: 3 hrs steeping at 17° C., 4 days germination at 15° C., followed by drying in a 50-80° C. kiln. The optimal length of time far steeping G1* grain differed slightly compared to other grains; Sloop: 8 hr-9 hr-5 hr steep/rest/step programme at 17° C.; R1508: 7 hr-8 hr-3 hr steep/rest/step programme at 17° C.; R56: 8 hr-10 hr-5 hr sleep/rest/step programme at 17° C. Analysis protocols were as specified by European Brewing Convention (EBC) or Institute of Brewing (IOB). Moisture content of the grain was determined by Near Infrared spectroscopy (NIR). Total nitrogen content was determined by the method of Dumas. Data for the malts are shown in Table 9. One significant difference between the G1* grain and the other varieties tested was that the diastatic power measures for G1* and R1508 were much lower than for Sloop or R56 grain. This was therefore associated with the lys3 mutation in G1* and R1508.

Maltings were repeated and combined for each variety. Approximately 4 kg of malt from each of the lines G1*, R56, R1508 and Sloop (wild-type) was brewed and bottled as follows. The malt samples were bittered with Tettnang hops for 60 min at boiling temperature to achieve 21-22 bitter units (IBU). Fermentation was with US-05 yeast (Fermentis) at 18-20° C. The fermented product was kegged without filtration and force-carbonated before bottling. All of the beers were still cloudy when bottled but were clearer after 2-4 weeks storage. The beers had a noticeable "butterscotch" aroma and flavour due to diacetyl when kegged and bottled but this also faded on storage.

Data for the brewed products are shown in Table 10. The alcohol content for the beer made from the G1* grain was 4.2% by volume. The G1* beer had a slightly reduced, but satisfactory, head of foam after pouring.

TABLE 9

Data for malting characteristics of G1* grain.

| Variety | Peak grain moisture achieved % | Malt Moisture % | Extract EBC fine | Colour EBC | Wort Clarity EBC | Total notrogen (% d wt) | % Soluble nitrogen EBC | Kohlbach Index EBC | Viscosity EBC | % Apparent Attenuation Limit EBC | β-Glucan EBC mg/L | Diaststic power IOB |
|---|---|---|---|---|---|---|---|---|---|---|---|---|
| G1* | 46.5 | 3.9 | 75.3 | 5.8 | 1.5 | 2.10 | 0.96 | 46 | 1.52 | 65.3 | 86 | 9 |
| Sloop | 45.7 | 4.1 | 80.7 | 3.1 | 1 | 1.94 | 0.86 | 44 | 1.55 | 76.9 | 237 | 79 |
| R1508 | 50.7 | 4.1 | 77.6 | 5.4 | 1 | 1.86 | 0.99 | 53 | 1.68 | 72.3 | 124 | 13 |
| R56 | 48.1 | 3.9 | 79.6 | 4.3 | 1 | 1.77 | 0.78 | 44 | 1.53 | 78.5 | 240 | 63 |

TABLE 10

Data for characteristics of beer brewed from G1* grain.

|  | SLOOP | R1508 | R56 | G1* |
|---|---|---|---|---|
| Batch Volume (lt) | 15.0 | 14.1 | 18.6 | 18.0 |
| Malt Weight (kg) | 3.60 | 3.33 | 4.00 | 4.55 |
| Protein Rest (Temp/Time) | 57 C./20 min | 56 C./20 min | 54 C./20 min | 55 C./20 min |
| Amylase Rest (Temp/Time) | 65 C./1 hr | 63-65 C./1 hr | 64-65 C./2 hrs | 64-65 C./2 hrs |
| Original Gravity (SG) | 1.051 | 1.052 | 1.051 | 1.049 |
| Final Gravity (SG) | 1.014 | 1.013 | 1.012 | 1.017 |
| Alcohol content by volume (%) | 4.8% | 5.1% | 5.2% | 4.2% |

These experiments indicated that G1* grain could be successfully malted and brewed.

Hordein levels in the beer made from G1* grain, measured by immunoassay, are expected to be less than 1 ppm, and in some case less than 0.5 ppm. This compares to a range in hordein levels in wheat beer of 10-41 ppm, in stout of 9-15 ppm, in lagers of 3-9 ppm.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 60/964,672, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Almeida and Allshire (2005) TRENDS Cell Biol 15: 251-258.
Anderson et at (2000) Nature Medicine 6: 337-342.
Anderson et al. (2005) Gut 54:1217-1223.
Aventz-Hansen (2000) Journal of Experimental Medicine 191: 603-612.
Biagi et al. (2004) Nutrition Reviews 62:360-363.
Bourque (1995) Plant Sci. 105: 125-149.
Bradford (1976) Analytical Chemistry 72: 248-254.
Brandt et al. (1990) Eur J Biochem 194:499-505.
Campbell et al. (2001) Insect Biochemistry and Molecular Biology 31: 513-520.
Capecchi (1980) Cell 22:479-488.
Catassi et al. (2007) Am. J. Clin. Nutr. 85:160-166.
Cheng et al. (1996) Plant Cell Rep. 15:653-657.
Clapp (1993) Clin. Perinatol. 20:155-168.
Collin et al. (2004) Aliment Pharmacol Ther 19:1277-1283.
Comai et al. (2004) Plant J 37: 778-786.
Curiel et al. (1992) Hum. Gen. Ther. 3:147-154.
Davies et al. (1993) Cell Biology International Reports 17:195-202.
De Anglis et al. (2007) J Food Protection 70:135-144.
Doll (1976) Genetic studies of high lysine barley mutants. In "Barley Genetics III".
Gaul H (ed). Verlag, Munchen:542-546.
Doll (1980) Heriditas 93:217-222.
Doll (1983) Barley seed proteins and possibilities for their improvement. In "Seed Proteins: Biochemistry, Genetics, Nutritional Value", Gottschalk W, Muller H P (eds). Martinus Nijhoff, The Hague:207-223.
Doll et al (1973) Barley Genetics Newsletter 3:12-13.
Douliez et al. (2000) J Cereal Sci 32:1-20.
Dostalek et al. (2006) Food Additives and Contaminants 23:1074-1078.
Eglitis et al. (1988) Biotechniques 6:608-614.
Ellis et al. (1990) Clin Chim Acta 189: 123-130.
Fasano et al. (2003) Archives of Internal Medicine 163: 286-292.
Field et al. (1982) Theoretical and Applied Genetics 62:329-336.
Folich et al. (1957) J Biol Chem. 226:497-509.
Fujimura et al. (1985) Plant Tissue Culture Letters 2:74.
Gellrich et al. (2003) Cereal Chem 80:102-109.
Graham et al. (1973) Virology 54:536-539.
Grant et al. (1995) Plant Cell Rep. 15:254-258.
Hadjivassiliou et al. (2004) Trends Immunol 25:578-82.
Haseloff and Gerlach (1988) Nature 134:585-591.
Hejgaard and Boisen (1980) Hereditas 93:311-320.
Henikoff et al. (2004) Plant Physiol 135: 630-636.
Hogberg et al. (2004) Gut 53: 649-654.
Hovell et al. (2001) Med J Aust 175: 247-250.
Ingerversen et al. (1973) Experientia 29:1151-1152.
Jaradat (1991) Theor Appl Genet 83:164468.
Jensen (1979). Chromosomal location of one dominant and four recessive high-lysine genes in barley mutants. In "Seed Protein Improvement in Cereals and Grain Legumes". IAEA/FAO/GSF, STI/PUB/496, Vienna:86-96.
Kanerva et al. (2005) J Instit Brewing 111: 61-64.
Karlsson (1977) Barley Genetics Newsletter 7:40-43.
Kasarda et al. (1984) PNAS 81:4712-4716.
Kim et al. (2004) Proc Natl Acad Sci USA 101:4175-9.
Klemsdal (1987) Hereditas 107: 107-114.
Koeie and Kreis (1978) Hordein and starch synthesis in developing high-lysine and normal barley seeds at different N-fertiliser levels. In "Carbohydrate and protein synthesis" Miflin B J and Zoeschke M (eds). Commission of the European Communities, 1978; publication EUR 6043 En:137-150.
Koziel et al. (1996) Plant Mol. Biol. 32:393-405.
Kreis (1979) Starch synthesis and prolamin level in single and double high-lysine barley mutants. Thesis Universsite Catholique de Louvain, Belgium 127 pp.
Kreis and Doll (1980) Physiol. Plant 48:139-143.
Kreis et al. (1983) Cell 34:161-477.
Kreis et al. (1984) Biochem. Genetics 22: 231-255.
Kreis and Shewry (1989) BioEssays 10:201-207.
Larroque et al. (2000) In Shewry and Tatham, eds. Seventh Internatl Workshop on Gluten Proteins, Bristol UK. Instit for Arable Crops Res 2000: 136-139.
Lu et al. (1993) J. Exp. Med. 178:2089-2096.
Lundin et al. (2003) Gut 52: 1649-1652.
Marchylo et al. (1986) Cereal Chem 63: 219-231.
Marti et al. (2005) J Pharmacol Exp Therapeut 312:19-26.
Millar and Waterhouse (2005) Funct Integr Genomics 5:129-135.
Mullins et al. (1999) Eur J Plant Pathol 105:465-475.
Munck et al. (1970) Science 168:985-987.
Olsen (1977) Hereditas 87: 11-20.
Pasquinelli et al. (2005) Curr Opin Genet Develop 15: 200-205.
Peraaho et al. (2004a) Journal of the American Dietetic Association 104: 1148-1150.
Peraaho et al. (2004b) Scandinavian Journal of Gastroenterology 39: 27-31.
Perriman et al. (1992) Gene 113: 157-163.
Peters et al. (2003) Arch Intern Ivied 163:1566-1572.
Pynnonen et al. (2004) Psychosomatics 45: 325-335.
Senior (1998) Biotech. Genet. Engin. Revs. 15: 79-119.
Shan et al. (2002) Science 297: 2275-2279.
Sheehan and Skerritt (1997) J Inst Brewing 103: 297-306.
Shewry et al. (1980) Biochemical Genetics 18:33-151.
Shewry et al. (1978) Journal of Experimental Botany 29:677-692.
Shewry et al. (1999) The prolamins of the Triticeae. In Shewry P. R., Casey R., eds Seed Proteins. Klewer, London, pp 35-78.
Shewry and Halford (2002) Journal of Experimental Botany 53:947-958.

Shippy et al. (1999) Mol. Biotech. 12: 117-129.
Slade and Knauf (2005) Transgenic Res 14: 109-115.
Skerritt (1988) J. Cereal Science 7:251-263.
Smith et al. (2000) Nature 407: 319-320.
Sollid (2002) Nature Reviews Immunology 2: 647-655.
Sorell et al. (1998) FEES Letts 439;46-50.
Sorensen et al. (1996). Mol Gen Genet 250:750-760.
Stepniak et al. (2006) Am J Physiol-Gastrointest Liver Physiol 291:621-629.
Tallberg (1977) Hereditas 87: 43-46.
Thompson (2001) J. Amer Diet Assoc 101: 1456-1459.
Tingay et al. (1997) Plant J 11:1369-1376.
Toriyama et al. (1986) Theor. Appl. Genet. 205:34.
Treem (2004) Current Opinion in Pediatrics 16: 552-559.
Ulrich and Eslick (1977) Barley Genetics Newsletter 7:66-73.
Ullrich and Eslick (1978) Barley Genetics Newsletter 8:114-125.
Vader et al. (2003) Gastroenterology 125: 1105-1113.
Verkarre et al. (2004) J Pediatric Gastroenterology and Nutrition 38: 140-142.
Wagner et al. (1992) Proc. Natl. Acad. Sci. USA 89:6099-6103.
Waterhouse et al. (1998) Proc. Natl. Acad. Sci. USA 95: 13959-13964.
Wieser et al. (1994) Journal of Cereal Science 19, 149-155.
Williamson and Marsh (2000) Celiac Disease. In M N Marsh, ed Celiac Disease: Methods and Protocols. Humana Press, Totowa, N.J., pp 1-9.
Zikiryaeva and Kasimov (1972) Uzbekskii Biologicheskii Zhurnal 6:18-20.

---

The invention claimed is:

1. A malt-based beverage, comprising one or more barley grain proteins, produced from malt obtained from barley grain homozygous for at least two genetic variations which result in 25% or less of the level of total hordeins when compared to a corresponding wild-type barley grain, wherein the at least two genetic variations comprise: (a) a deletion of most or all of the B-hordein encoding genes at the Hor2 locus of barley and (b) a mutation in a Lys3 gene whereby the barley grain comprising the mutation comprises 25% or less of the level of C-hordein when compared to the corresponding wild-type barley grain, wherein the malt-based beverage comprises 25% or less of the level of total hordeins relative to a malt-based beverage produced in the same manner from malt obtained from corresponding wild-type barley grain.

2. The malt-based beverage of claim 1, wherein the malt-based beverage is beer.

3. The malt-based beverage of claim 2, wherein the beer comprises at least 2% ethanol.

4. The malt-based beverage of claim 1, wherein the malt-based beverage is whiskey.

5. The malt-based beverage of claim 1, wherein the one or more barley grain proteins comprises barley 9kDa lipid transfer protein 1 (LTP1) or protein Z or both.

6. The malt-based beverage of claim 1, wherein the malt-based beverage is produced from malt comprising less than 200 ppm hordeins.

7. The malt-based beverage of claim 1, wherein the malt-based beverage comprises less than 1 ppm hordeins.

8. The malt-based beverage of claim 1, wherein the malt-based beverage comprises a reduced level of B-hordein, wherein the level of B-hordein is 2.5% or less of the level of B-hordein in a malt-based beverage produced in the same manner from corresponding wild-type barley grain.

9. The malt-based beverage of claim 1, wherein the malt-based beverage comprises a reduced level of C-hordein, wherein the level of C-hordein is 2.5% or less of the level of C-hordein in the malt-based beverage produced in the same manner from corresponding wild-type barley grain.

10. The malt-based beverage of claim 1, wherein the malt-based beverage comprises a reduced level of B-hordein and a reduced level of C-hordein, wherein the level of B-hordein is 2.5% or less of the level of B-hordein in the malt-based beverage produced in the same manner from corresponding wild-type barley grain, and the level of C-hordein is 2.5% or less of the level of C-hordein in the malt-based beverage produced in the same manner from corresponding wild-type barley grain.

11. A malt-based beverage, comprising one or more barley grain proteins, produced from malt obtained from barley grain homozygous for at least two genetic variations which result in 25% or less of the level of total hordeins when compared to a corresponding wild-type barley grain, wherein the at least two genetic variations comprise: (a) a deletion of most or all of the B-hordein encoding genes at the Hor2 locus of barley and (b) a mutation in a Lys3 gene whereby the barley grain comprising the mutation comprises 25% or less of the level of C-hordein when compared to the corresponding wild-type barley grain, wherein the malt-based beverage is beer which comprises less than 1ppm hordeins.

12. The malt-based beverage of claim 11, wherein the level of B-hordein is 2.5% or less of the level of B-hordein in a malt-based beverage produced in the same manner from corresponding wild-type barley grain.

13. The malt-based beverage of claim 11, wherein the level of C-hordein is 2.5% or less of the level of C-hordein in the malt-based beverage produced in the same manner from corresponding wild-type barley grain.

14. The malt-based beverage of claim 11, wherein the level of B-hordein is 2.5% or less of the level of B-hordein in the malt-based beverage produced in the same manner from corresponding wild-type barley grain, and the level of C-hordein is 2.5% or less of the level of C-hordein in the malt-based beverage produced in the same manner from corresponding wild-type barley grain.

* * * * *